US012780835B2

(12) United States Patent
Cheng et al.

(10) Patent No.: US 12,780,835 B2
(45) Date of Patent: Nov. 3, 2026

(54) HETEROARYLQUINAZOLINE COMPOUNDS AS PROTEIN KINASE INHIBITORS

(71) Applicant: CHENGDU CYNOGEN BIO-PHARMACEUTICAL TECHNOLOGY CO., LTD., Chengdu (CN)

(72) Inventors: Hang Cheng, Chengdu (CN); Weiyan Xiong, Chengdu (CN); Wei Niu, Chengdu (CN); Bin Yu, Chengdu (CN); Yu Jiang, Chengdu (CN)

(73) Assignee: CHENGDU CYNOGEN BIO-PHARMACEUTICAL TECHNOLOGY LTD., Chengdu (CN)

( * ) Notice: Subject to any disclaimer, the term of this patent is extended or adjusted under 35 U.S.C. 154(b) by 579 days.

(21) Appl. No.: 18/038,258

(22) PCT Filed: Nov. 26, 2021

(86) PCT No.: PCT/CN2021/133527

§ 371 (c)(1),
(2) Date: May 23, 2023

(87) PCT Pub. No.: WO2022/111634

PCT Pub. Date: Jun. 2, 2022

(65) Prior Publication Data

US 2023/0416271 A1 Dec. 28, 2023

(30) Foreign Application Priority Data

Nov. 26, 2020 (CN) ........................ 202011344710.8

(51) Int. Cl.
*C07D 498/04* (2006.01)
*C07D 487/04* (2006.01)

(52) U.S. Cl.
CPC ......... *C07D 498/04* (2013.01); *C07D 487/04* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 10,392,367 | B2 * | 8/2019 | Vacca .................. C07D 401/14 |
| 2005/0148603 | A1 * | 7/2005 | Jimenez .................. A61P 11/02 544/278 |
| 2006/0264628 | A1 | 11/2006 | McInnes et al. |
| 2010/0280026 | A1 | 11/2010 | Jimenez et al. |
| 2011/0105542 | A1 | 5/2011 | Caldareli et al. |
| 2020/0347067 | A1 | 11/2020 | Ye |
| 2022/0281878 | A1 | 9/2022 | Cheng et al. |
| 2022/0363690 | A1 | 11/2022 | Cheng et al. |

FOREIGN PATENT DOCUMENTS

| | | | | |
|---|---|---|---|---|
| CN | 1849325 A1 | 10/2006 | | |
| CN | 1894258 A | 1/2007 | | |
| CN | 102076689 A1 | 5/2011 | | |
| WO | WO-2004104007 A1 * | 12/2004 | .............. | A61P 43/00 |
| WO | WO-2005037843 A1 * | 4/2005 | .............. | A61P 35/02 |
| WO | 2010078421 | 7/2010 | | |
| WO | 2019213403 A1 | 11/2019 | | |
| WO | 2020223469 A1 | 11/2020 | | |
| WO | 2021023104 A1 | 2/2021 | | |
| WO | 2021043190 A1 | 3/2021 | | |

OTHER PUBLICATIONS

Lukasik et al., Int. J. Mol. Sci. (2021), 22, 2935, 35 pages (Year: 2021).*
Acs STN Registry 2526004-16-8 22.11 E 2020(Nov. 22, 2020).
Asghar, "The history and future of targeting cyclin-dependent kinases in cancer therapy", Nat. Rev. Drug. Discovery 201514(2): 130-146.
Berge S. M. et al. "Pharmaceutical Salts," Journal of Pharmaceutical Science, Jan. 1977; vol. 66: No. 1-19.
D. Fleisher,S. Ramon, H. Barbra "Improved oral drug delivery solubility limitations overcome by the use of prodrugs" Advanced Drug Delivery Reviews (1996) 19(2) 115-130.
G. A. Molander, J. A. McKie. Samarium(II) iodide-induced reductive cyclization of unactivated olefinic ketones. Sequential radical cyclization/intermolecular nucleophilic addition and substitution reactions. J. Org. Chem. 1992, 57, 11, 3132-3139.
Y. Fujiwara, J. A. Dixon, F. O. Hara, Phil S. Baran, et al. "Practical and innate carbon-hydrogen functionalization of heterocycles", Nature Dec. 6, 2012, vol. 492, Nature 95.

(Continued)

*Primary Examiner* — George W Kosturko
*Assistant Examiner* — Jason M. Nolan
(74) *Attorney, Agent, or Firm* — Lowenstein Sandler LLP

(57) ABSTRACT

Provided are heteroarylquinazoline compounds represented by general formula (X), which can be used for treating cell proliferation disorders. The compounds are effective inhibitors of cyclin-dependent kinases (CDKs) and can effectively inhibit CDK2, CDK4, CDK6 and CDK9 kinases.

(X)

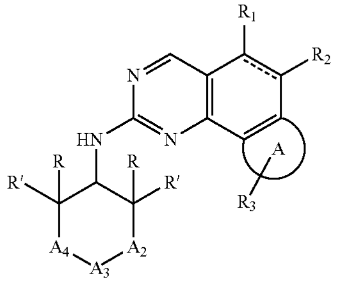

21 Claims, No Drawings

(56) References Cited

OTHER PUBLICATIONS

Lan, Ping et al. "3D-QSAR and Dockingstudies on Pyrazolo[4,3-h]Qinazoline-3-Carboxamides as Cyclic-Dependent Kinase2(CDK2) Inhibitors" Bioorganic & Medicinal Chemistry Letters, vol. 20, No., 22, Sep. 24, 2010, pp. 6794-6772.
Gabriella, T. et al. "Identification of Potent Pyrazolo[4,3-h]Qinazoline-3-Carboxamides as Multi-Cyclin-Dependent Kinase Inhibitors", Journal of Medicinal Chemistry, vol. 53, No. 5, Feb. 8, 2010, pp. 2171-2187.
English Translation of International Search Report and Written Opinion for PCT/CN2021/133527 mailed Mar. 1, 2022, 12 pages.
Office Action with English translation for Chinese Patent Application No. 202180078208.3 dated Jun. 12, 2025, 24 pages.

* cited by examiner

HETEROARYLQUINAZOLINE COMPOUNDS AS PROTEIN KINASE INHIBITORS

CROSS-REFERENCE TO RELATED APPLICATION(S)

The present application is a national stage entry under 35 U.S.C. § 371 of International Application No. PCT/CN2021/133527, filed on Nov. 26, 2021, which claims priority to Chinese Patent Application No. 202011344710.8, filed on Nov. 26, 2020. The contents of these applications are hereby incorporated by reference in their entirety.

FIELD OF THE INVENTION

The present disclosure provides a class of heteroaryl-fused quinazoline compounds as inhibitors of cyclin-dependent kinase (CDK), which have a broad-spectrum, strong inhibitory activity against CDK and have selectivity over CDK2, CDK4, CDK6 and CDK9. The compounds of the present disclosure are effective in treating diseases such as cancer, inflammation, etc.

BACKGROUND OF THE INVENTION

Cyclin-dependent kinase (CDK) and cyclin are important factors in cell cycle regulation. CDK can combine with cyclin to form a heterodimer, in which CDK is the catalytic subunit and cyclin is the regulatory subunit. Various cyclin-CDK complexes thus formed phosphorylate different substrates, and promote and transform different phases of the cell cycle.

In the past decade, CDK inhibitors have become a hot topic in the development of new anti-tumor drugs, and more than 20 CDK inhibitors have entered the clinical stage. Although the preclinical pharmacodynamic results of CDK inhibitors are remarkable, the results of most clinical trials are not satisfactory. Problems include lack of efficacy in solid tumors and greater toxicity. Some CDK inhibitor drugs lack selectivity for CDK subtypes, resulting in greater toxicity.

CDK4 and CDK6 are two closely related kinases that bind to Cyclin D during the tumor cell cycle to promote cell cycle progress from G1 phase to S phase and are required for cell cycle progression. It has been shown that in human tumors (such as breast cancer and myeloma), activation of CDK4 and CDK6 leads to cell cycle changes. Inhibition of CDK4 and CDK6 prevents the inactivation of the tumor suppressor protein Rb and interferes with tumor cell cycle progression.

Overexpression of CDK2 is related to abnormal regulation of cell cycle, and cyclin E/CDK2 complex plays an important role in regulating G1/S conversion, histone biosynthesis and centrosome replication. Progressive phosphorylation of Rb by cyclin D/CDK4/6 and cyclin E/CDK2 releases G1 transcription factor E2F and promotes entry of S phase. Activation of cyclin A/CDK2 during early S phase promotes phosphorylation of endogenous substrates, which allows DNA replication and inactivation of E2F to complete S phase. (Asghar et al., The history and future of targeting cyclin-dependent kinases in cancer therapy, Nat. Rev. Drug. Discov. 2015; 14(2): 130-146).

Cyclin-dependent kinase 9 (CDK9) participates in the formation of positive transcription elongation factor (P-TEFb) and plays a key role in the transcription regulation, especially in the regulation of short-lived anti-apoptotic proteins, which are very important for the survival of many tumor cells, so CDK9 has become an important target for cancer treatment. Dinaciclib (MK-7965) and Seliciclib (CYC202), small molecular inhibitors with CDK9 inhibitory activity, have been approved for clinical trials of breast cancer and hematological tumors and combined chemotherapy for advanced solid tumors.

Although many CDK inhibitor compounds have been published, there is still a need for more CDK inhibitors (especially pan-inhibitor of CDK2 combined with CDK4/6 or CDK9) to treat CDK-related diseases.

SUMMARY OF THE INVENTION

The present disclosure provides a class of heteroaryl-fused quinazoline compounds as inhibitors of cyclin-dependent kinase, which have a strong inhibitory activity. In addition, compared with the existing drugs, the compounds of the present disclosure can further improve the pharmacokinetic properties, including the significant improvement in the metabolic stability and clearance rate over the existing compounds.

In one aspect, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (X):

(X)

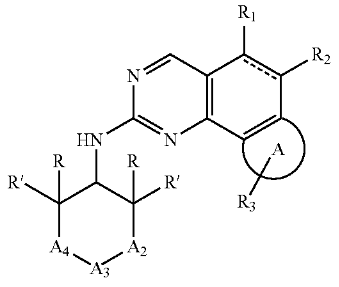

wherein:

⎓ indicates a single bond or a double bond;

ring A is a 5- to 6-membered heteroaryl; alternatively selected from pyrrolyl, furyl, thienyl, imidazolyl, pyrazolyl, oxazolyl, isoxazolyl, thiazolyl, isothiazolyl, triazolyl, oxadiazolyl and thiadiazolyl; alternatively selected from:

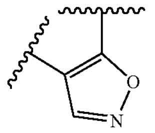 and 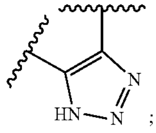 ;

$A_2$ is CRR' or NR";

$A_3$ is CRR' or $NR_4$;

$A_4$ is CRR' or NR";

or $A_3$, $A_4$ and substituents thereon are combined to form $C_{6-10}$ aryl or 5- to 10-membered heteroaryl;

R and R' are independently selected from H, D, —$OR_{O1}$, —$NR_{N1}R_{N2}$, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_1$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, —$OR_a$, —$SR_a$, —$NR_bR_c$, —$C(O)R_a$, —$C(O)OR_a$, —$C(O)NR_bR_c$, —$C_{0-6}$ alkylene-$OR_5$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_{O1}$, $R_{N1}$ and $R_{N2}$ are independently selected from H, $C_{1-6}$ alkyl, $C_{1-6}$ haloalkyl, —$C(O)R_d$, —$S(O)_mR_d$, —$C_{1-6}$ alkylene-$OR_5$, —$C_{1-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

or $R_{N1}$ and $R_{N2}$ are taken together with the nitrogen atom to which they are attached to form 3- to 7-membered heterocyclyl or 5- to 10-membered heteroaryl, which is optionally substituted by 1, 2 or 3 $R_8$ groups;

$R_4$ and R" are independently selected from H, $C_{1-6}$ alkyl, $C_{1-6}$ haloalkyl, $C_{2-6}$ alkenyl, $C_{2-6}$ alkynyl, —$C(O)R_d$, —$S(O)_mR_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl;

$R_8$ is independently selected from H, D, halogen, —CN, -L-$C_{3-7}$ cycloalkyl, -L-3- to 7-membered heterocyclyl, -L-$C_{6-10}$ aryl and -L-5- to 10-membered heteroaryl;

L is selected from a chemical bond, —C(O)—, —C(O)NH—, —$C_{1-6}$ alkylene-, —$C_{2-6}$ alkenylene- and —$C_{2-6}$ alkynylene-; and $R_8$ is further substituted by H, D, halogen, —CN, $C_{1-6}$ alkyl or $C_{1-6}$ haloalkyl.

In another aspect, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I):

(I)

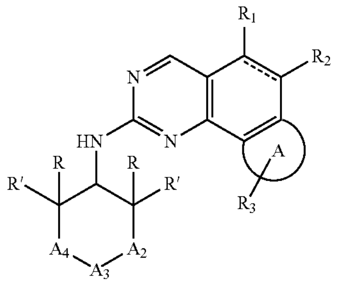

wherein:

⎓ indicates a single bond or a double bond;

ring A is a 5- to 6-membered heteroaryl; alternatively selected from pyrrolyl, furyl, thienyl, imidazolyl, pyrazolyl, oxazolyl, isoxazolyl, thiazolyl, isothiazolyl, triazolyl, oxadiazolyl and thiadiazolyl; alternatively selected from:

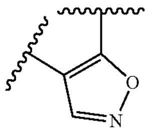

and

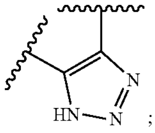

;

$A_2$ is CRR' or NR";

$A_3$ is CRR' or $NR_4$;

$A_4$ is CRR' or NR";

or $A_3$, $A_4$ and substituents thereon are combined to form $C_{10}$ aryl or 5- to 10-membered heteroaryl;

R and R' are independently selected from H, D, —$OR_{O1}$, —$NR_{N1}R_{N2}$, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_1$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_{O1}$, $R_{N1}$ and $R_{N2}$ are independently selected from H, $C_{1-6}$ alkyl, $C_{1-6}$ haloalkyl, —C(O)$R_d$, —S(O)$_m$$R_d$, —$C_{1-6}$ alkylene-$OR_5$, —$C_{1-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

or $R_{N1}$ and $R_{N2}$ are taken together with the nitrogen atom to which they are attached to form 3- to 7-membered heterocyclyl or 5- to 10-membered heteroaryl, which is optionally substituted by 1, 2 or 3 $R_8$ groups;

$R_4$ and R" are independently selected from H, $C_{1-6}$ alkyl, $C_{1-6}$ haloalkyl, $C_{2-6}$ alkenyl, $C_{2-6}$ alkynyl, —C(O)$R_d$, —S(O)$_m$$R_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl;

$R_8$ is independently selected from H, D, halogen, —CN, -L-$C_{3-7}$ cycloalkyl, -L-3- to 7-membered heterocyclyl, -L-$C_{6-10}$ aryl and -L-5- to 10-membered heteroaryl;

L is selected from a chemical bond, —C(O)—, —C(O)NH—, —$C_{1-6}$ alkylene-, —$C_{2-6}$ alkenylene- and —$C_{2-6}$ alkynylene-; and $R_8$ is further substituted by H, D, halogen, —CN, $C_{1-6}$ alkyl or $C_{1-6}$ haloalkyl.

In another aspect, the present disclosure provides a pharmaceutical composition comprising a compound of the present disclosure, and optionally pharmaceutically acceptable excipient(s).

In another aspect, the present disclosure provides a pharmaceutical composition comprising a compound of the present disclosure and pharmaceutically acceptable excipient(s), which further comprises other therapeutic agent(s).

In another aspect, the present disclosure provides a kit comprising a compound of the present disclosure, other therapeutic agent(s) and pharmaceutically acceptable carrier(s), adjuvant(s) or vehicle(s).

In another aspect, the present disclosure provides use of a compound of the present disclosure in the preparation of a medicament for the treatment and/or prevention of a CDK-mediated disease.

In another aspect, the present disclosure provides a method of treating and/or preventing a CDK-mediated disease in a subject, including administering a compound of the present disclosure or a composition of the present disclosure to the subject.

In another aspect, the present disclosure provides a compound or a composition of the present disclosure, for use in treating and/or preventing a CDK-mediated disease.

In a specific embodiment, the diseases described herein include cell proliferative diseases such as solid tumors such as sarcomas and carcinomas (e.g., fibrosarcoma, myxosarcoma, liposarcoma, chondrosarcoma, osteosarcoma, chordoma, angiosarcoma, endothelial sarcoma, lymphangiosarcoma, lymphangioendothelioma, synovialoma, mesothelioma, ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, hidradenoma, sebaceous carcinoma, papillary carcinoma, papillary adenocarcinoma, cystadenocarcinoma, medullary carcinoma, bronchial carcinoma, renal cell carcinoma, liver cancer, cholangiocarcinoma, choriocarcinoma, seminoma, embryonal cancer, embryonal carcinosarcoma, cervical cancer, uterine cancer, testicular cancer, lung cancer, small cell lung cancer, bladder cancer, epithelial cancer, glioma, astrocytoma, medulloblastoma, craniopharyngioma, ependymoma, pineal tumor, hemangioblastoma, acoustic neuroma, oligodendroglioma, schwannoma, meningioma, melanoma, neuroblastoma and retinoblastoma).

Other objects and advantages of the present disclosure will be apparent to those skilled in the art from the subsequent specific embodiments, examples and claims.

Definitions

Chemical Definitions

Definitions of specific functional groups and chemical terms are described in more detail hereafter.

When a range of values is listed, each value and sub-range within the range are intended to be included. For example, "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

It should be understood that when described herein any of the moieties defined forth below may be substituted by a variety of substituents, and that the respective definitions are intended to include such substituted moieties within their scope as set out below. Unless otherwise stated, the term "substituted" is to be defined as set out below.

"$C_{1-6}$ alkyl" refers to a radical of a straight or branched, saturated hydrocarbon group having 1 to 6 carbon atoms. In some embodiments, $C_{1-4}$ alkyl is alternative. Examples of $C_{1-6}$ alkyl include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$) or i-Bu (—$CH_2CH(CH_3)_2$).

"$C_{2-6}$ alkenyl" refers to a radical of a straight or branched hydrocarbon group having 2 to 6 carbon atoms and at least one carbon-carbon double bond. In some embodiments, $C_{2-4}$ alkenyl is alternative. Examples of $C_{2-6}$ alkenyl include vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"$C_{2-6}$ alkynyl" refers to a radical of a straight or branched hydrocarbon group having 2 to 6 carbon atoms, at least one carbon-carbon triple bond and optionally one or more carbon-carbon double bonds. In some embodiments, $C_{2-4}$ alkynyl is alternative. Examples of $C_{2-6}$ alkynyl include, but are not limited to, ethynyl ($C_2$), 1-propynyl ($C_3$), 2-propynyl ($C_3$), 1-butynyl ($C_4$), 2-butynyl ($C_4$), pentynyl (C), hexynyl ($C_6$), etc. The term "$C_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"—$C_{1-6}$ alkylene-, —$C_{2-6}$ alkenylene- or —$C_{2-6}$ alkynylene-" refers to a divalent group of the "$C_{1-6}$ alkyl, $C_{2-6}$ alkenyl or $C_{2-6}$ alkynyl" as defined above.

"$C_{1-6}$ alkylene" refers to a divalent group formed by removing another hydrogen of the $C_{1-6}$ alkyl, and can be a substituted or unsubstituted alkylene. In some embodiments, $C_{1-4}$ alkylene is yet alternative. The unsubstituted alkylene groups include, but are not limited to, methylene ($-CH_2-$), ethylene ($-CH_2CH_2-$), propylene ($-CH_2CH_2CH_2-$), butylene ($-CH_2CH_2CH_2CH_2-$), pentylene ($-CH_2CH_2CH_2CH_2CH_2-$), hexylene ($-CH_2CH_2CH_2CH_2CH_2CH_2-$), etc. Examples of substituted alkylene groups, such as those substituted with one or more alkyl (methyl) groups, include, but are not limited to, substituted methylene ($-CH(CH_3)-$, $-C(CH_3)_2-$), substituted ethylene ($-CH(CH_3)CH_2-$, $-CH_2CH(CH_3)-$, $-C(CH_3)_2CH_2-$, $-CH_2C(CH_3)_2-$), substituted propylene ($-CH(CH_3)CH_2CH_2-$, $-CH_2CH(CH_3)CH_2-$, $-CH_2CH_2CH(CH_3)-$, $-C(CH_3)_2CH_2CH_2-$, $-CH_2C(CH_3)_2CH_2-$, $-CH_2CH_2C(CH_3)_2-$), etc.

"$C_{0-6}$ alkylene" means a chemical bond and "$C_{1-6}$ alkylene" as defined above.

"$C_{2-6}$ alkenylene" refers to a $C_{2-6}$ alkenyl group wherein another hydrogen is removed to provide a divalent radical of alkenylene, and which may be substituted or unsubstituted alkenylene. In some embodiments, $C_{2-4}$ alkenylene is yet alternative. Exemplary unsubstituted alkenylene groups include, but are not limited to, ethenylene ($-CH{=}CH-$) and propenylene (e.g., $-CH{=}CHCH_2-$, $-CH_2-CH{=}CH-$). Exemplary substituted alkenylene groups, e.g., substituted with one or more alkyl (methyl) groups, include but are not limited to, substituted ethylene ($-C(CH_3){=}CH-$, $-CH{=}C(CH_3)-$), substituted propylene (e.g., $-C(CH_3){=}CHCH_2-$, $-CH{=}C(CH_3)CH_2-$, $-CH{=}CHCH(CH_3)-$, $-CH{=}CHC(CH_3)_2-$, $-CH(CH_3)-CH{=}CH-$, $-C(CH_3)_2-CH{=}CH-$, $-CH_2-C(CH_3){=}CH-$, $-CH_2-CH{=}C(CH_3)-$), and the like.

"$C_{2-6}$ alkynylene" refers to a $C_{2-6}$ alkynyl group wherein another hydrogen is removed to provide a divalent radical of alkynylene, and which may be substituted or unsubstituted alkynylene. In some embodiments, $C_{2-4}$ alkynylene is yet alternative. Exemplary alkynylene groups include, but are not limited to, ethynylene ($-C{\equiv}C-$), substituted or unsubstituted propynylene ($-C{\equiv}CCH_2-$), and the like.

"Halo" or "halogen" refers to fluorine (F), chlorine (Cl), bromine (Br) and iodine (I).

"$C_{1-6}$ haloalkyl" represents the "$C_{1-6}$ alkyl" described above, which is substituted with one or more halogen groups. Examples include the mono-, di-, poly-halogenated, including perhalogenated, alkyl. A monohalogen substituent may have one iodine, bromine, chlorine or fluorine atom in the group; a dihalogen substituent and a polyhalogen substituent may have two or more identical halogen atoms or a combination of different halogens. Examples of alternative haloalkyl groups include monofluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The haloalkyl groups can be substituted at any available point of attachment, for example, with 1 to 5 substituents, 1 to 3 substituents or 1 substituent.

"$C_{3-7}$ cycloalkyl" refers to a radical of non-aromatic cyclic hydrocarbon group having 3 to 7 ring carbon atoms and zero heteroatoms. In some embodiments, $C_{3-6}$ cycloalkyl is yet alternative, and $C_{5-6}$ cycloalkyl is still alternative. The cycloalkyl also includes a ring system in which the cycloalkyl described herein is fused with one or more aryl or heteroaryl groups, wherein the point of attachment is on the cycloalkyl ring, and in such case, the number of carbon atoms continues to represent the number of carbon atoms in the cycloalkyl system. Exemplary cycloalkyl groups include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc.

"3- to 11-membered heterocyclyl" refers to a radical of 3- to 11-membered non-aromatic ring system having ring carbon atoms and 1 to 5 ring heteroatoms, wherein each of the heteroatoms is independently selected from nitrogen, oxygen, sulfur, boron, phosphorus and silicon. In the heterocyclyl containing one or more nitrogen atoms, the point of attachment can be a carbon or nitrogen atom as long as the valence permits. In some embodiments, 3- to 9-membered heterocyclyl is alternative, which is a radical of 3- to 9-membered non-aromatic ring system having ring carbon atoms and 1 to 5 ring heteroatoms. In some embodiments, 3- to 7-membered heterocyclyl is alternative, which is a radical of 3- to 7-membered non-aromatic ring system having ring carbon atoms and 1 to 4 ring heteroatoms. 3- to 6-membered heterocyclyl is alternative, which is a radical of 3- to 6-membered non-aromatic ring system having ring carbon atoms and 1 to 3 ring heteroatoms. 4- to 6-membered heterocyclyl is alternative, which is a radical of 4- to 6-membered non-aromatic ring system having ring carbon atoms and 1 to 3 ring heteroatoms. 5- to 6-membered heterocyclyl is still alternative, which is a radical of 5- to 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the cycloalkyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. Exemplary 3-membered heterocyclyl groups containing one heteroatom include, but are not limited to, aziridinyl, oxiranyl and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothienyl, pyrrolidinyl, dihydropyrrolyl and pyrrolyl-2, 5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocycly groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6, 6-bicyclic heterocyclyl herein) include, but are not limited to, tetrahydroquinolinyl, tetrahydroisoquinolinyl, etc.

The 3- to 11-membered heterocyclyl also includes spiroheterocyclyl, that is, a group in which two rings (e.g., a heterocycle and a carbocycle) share a carbon atom, wherein at least one of the rings is a heterocyclyl as defined above. More specifically, the spiroheterocyclyl is a spiro ring formed by two 4-membered rings, two 5-membered rings, two 6-membered rings, one 4-membered ring and one 5-membered ring, one 4-membered ring and one 6-membered ring, or one 5-membered ring and one 6-membered ring, wherein at least one of the rings is a 4- to 6-membered heterocyclyl as defined above. The 4- to 6-membered heterocyclyl containing 1, 2 or 3 O, N or S heteroatoms is alternative. The 4- to 6-membered heterocyclyl containing 1 N heteroatom is still alternative. Specific spiroheterocyclyl groups include, but are not limited to:

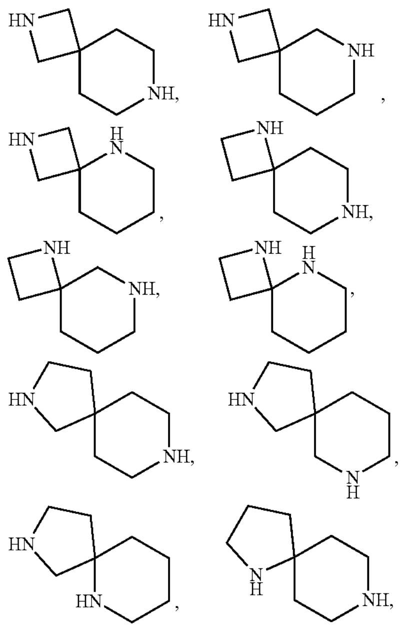

-continued

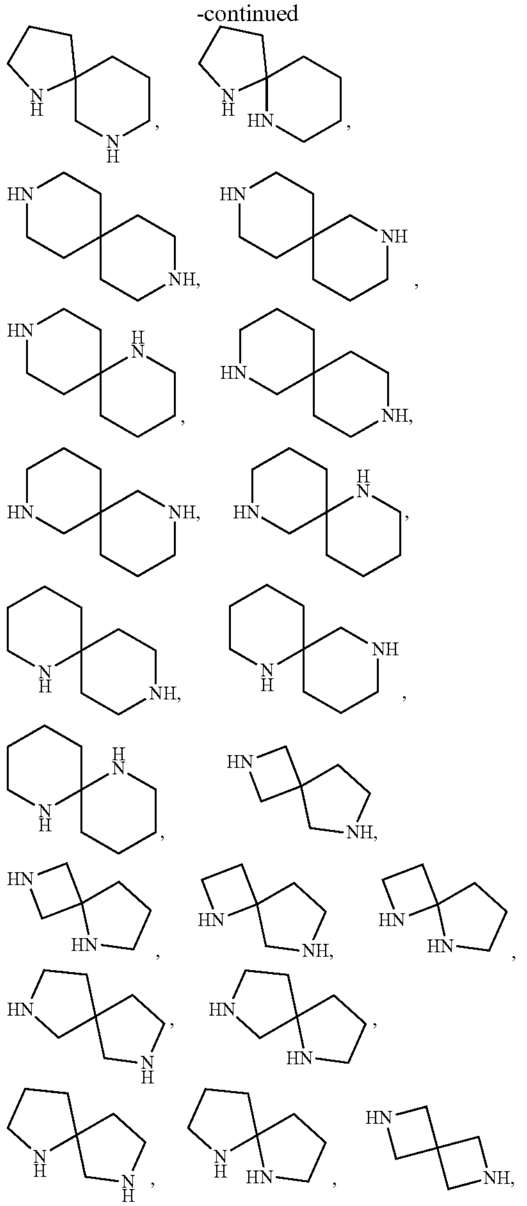

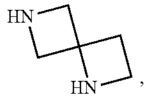

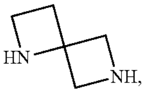

and

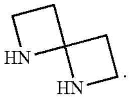

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared π electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl, e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system.

"5- to 10-membered heteroaryl" refers to a radical of 5- to 10-membered monocyclic or bicyclic 4n+2 aromatic ring system (e.g., having 6 or 10 shared π electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. Heteroaryl bicyclic systems may include one or more heteroatoms in one or two rings. Heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 6-membered heteroaryl groups are yet alternative, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (such as, 1, 2, 4-oxadiazoly), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6, 6-bicyclic heteroaryl groups include, but are not limited to, naphthyridinyl, pteridinyl, quinolyl, isoquinolyl, cinnolinyl, quinoxalinyl, phthalazinyl and quinazolinyl.

"Carbonyl", whether used alone or in conjunction with other terms (e.g., aminocarbonyl), is represented by —C(O)—.

"Oxo" represents =O.

"Thioxo" represents =S.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary substituents on carbon atoms include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3{}^+X^-$, $—N(OR^{cc})R^{bb}$, —SH, $—SR^{aa}$, $—SSR^{cc}$, $—C(=O)R^{aa}$, $—CO_2H$, —CHO, $—C(OR^{cc})_2$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—N^{bb}CO_2R^{aa}$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$$—OC(=NR^{bb})N(R^{bb})_2$, $—NR^{bb}C(=NR^{bb})N(R^{bb})_2$$—C(=O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(=O)R^{aa}$, $—OS(=O)R^{aa}$, $—Si(R^{aa})_3$, $—OSi(R^{aa})_3$, $—C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)_2R^{aa}$, $—OP(=O)_2R^{aa}$, $—P(=O)(R^{aa})_2$, $—OP(=O)(R^{aa})_2$, $—OP(=O)(OR^{cc})_2$, $—P(=O)_2N(R^{bb})_2$, $—OP(=O)_2N(R^{bb})_2$, $—P(=O)(NR^{bb})_2$, $—OP(=O)(NR^{bb})_2$, $—NR^{bb}P(=O)(OR^{cc})_2$, $—N^{bb}P(=O)(NR^{bb})_2$, $—P(R^{cc})_2$, $—P(R^{cc})_3$, $—OP(R^{cc})_2$, $—OP(R^{cc})_3$, $—B(R^{aa})_2$, $—B(OR^{cc})_2$, $—BR^{aa}(OR^{cc})$, alkyl, haloalkyl, alkenyl, alkynyl, carbocyclyl, heterocyclyl, aryl and heteroaryl, wherein each of the alkyl, alkenyl, alkynyl, carbocyclyl, heterocyclyl, aryl and heteroaryl is independently substituted with 0, 1, 2, 3, 4 or 5 $R^{dd}$ groups;

or two geminal hydrogen on a carbon atom are replaced with =O, =S, $=NN(R^{bb})_2$, $—NNR^{bb}C(=O)R^{aa}$$=NNR^{bb}C(=O)OR^{aa}$$=NNR^{bb}S(=O)_2R^{aa}$$=NR^{bb}$ or $=NOR^{cc}$ groups;

each of the $R^{aa}$ is independently selected from alkyl, haloalkyl, alkenyl, alkynyl, carbocyclyl, heterocyclyl, aryl and heteroaryl, or two of the $R^{aa}$ groups are combined to form a heterocyclyl or heteroaryl ring, wherein each of the alkyl, alkenyl, alkynyl, carbocyclyl, heterocyclyl, aryl and heteroaryl is independently substituted with 0, 1, 2, 3, 4 or 5 $R^{dd}$ groups;

each of the $R^{bb}$ is independently selected from hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)_2R^{aa}$, $—P(=O)(R^{aa})_2$, $—P(=O)_2N(R^{cc})_2$, $—P(=O)(NR^{cc})_2$, alkyl, haloalkyl, alkenyl, alkynyl, carbocyclyl, heterocyclyl, aryl and heteroaryl, or two $R^{bb}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{dd}$ groups;

each of the $R^{cc}$ is independently selected from hydrogen, alkyl, haloalkyl, alkenyl, alkynyl, carbocyclyl, heterocyclyl, aryl and heteroaryl, or two $R^{cc}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{dd}$ groups;

each of the $R^{dd}$ is independently selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3{}^+X^-$, $—N(OR^{ee})R^{ff}$, —SH, $—SR^{ee}$, $—SSR^{ee}$, $—C(=O)R^{ee}$, $—CO_2H$, $—CO_2R^{ee}$, $—OC(=O)R^{ee}$, $—OCO_2R^{ee}$, $—C(=O)N(R^{ff})_2$, $—OC(=O)N(R^{ff})_2$, $—NR^{ff}C(=O)$ $R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)_2R^{ee}$, $-P(=O)(R^{ee})_2$, $-OP(=O)(R^{ee})_2$, $-OP(=O)(OR^{ee})_2$, alkyl, haloalkyl, alkenyl, alkynyl, carbocyclyl, heterocyclyl, aryl, heteroaryl, wherein each of the alkyl, alkenyl, alkynyl, carbocyclyl, heterocyclyl, aryl and heteroaryl is independently substituted with 0, 1, 2, 3, 4 or 5 $R^{gg}$ groups, or two geminal $R^{dd}$ substituents can be combined to form =O or =S;

each of the $R^{ee}$ is independently selected from alkyl, haloalkyl, alkenyl, alkynyl, carbocyclyl, aryl, heterocyclyl, and heteroaryl, wherein each of the alkyl, alkenyl, alkynyl, carbocyclyl, heterocyclyl, aryl and heteroaryl is independently substituted with 0, 1, 2, 3, 4 or 5 $R^{gg}$ groups;

each of the $R^{ff}$ is independently selected from hydrogen, alkyl, haloalkyl, alkenyl, alkynyl, carbocyclyl, heterocyclyl, aryl and heteroaryl, or two $R^{ff}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{gg}$ groups;

each of the $R^{gg}$ is independently selected from halogen, $-CN$, $-NO_2$, $-N_3$, $-SO_2H$, $-SO_3H$, $-OH$, $-OC_{1-6}$ alkyl, $-ON(C_{1-6}$ alkyl$)_2$, $-N(C_{1-6}$ alkyl$)_2$, $-N(C_{1-6}$ alkyl$)_3{}^+X^-$, $-NH(C_{1-6}$ alkyl$)_2{}^+X^-$, $-NH_2(C_{1-6}$ alkyl$)^+X^-$, $-NH_3{}^+X^-$, $-N(OC_{1-6}$ alkyl$)(C_{1-6}$ alkyl), $-N(OH)(C_{1-6}$ alkyl), $-NH(OH)$, $-SH$, $-SC_{1-6}$ alkyl, $-SS(C_{1-6}$ alkyl), $-C(=O)(C_{1-6}$ alkyl), $-CO_2H$, $-CO_2(C_{1-6}$ alkyl), $-OC(=O)(C_{1-6}$ alkyl), $-OCO_2(C_{1-6}$ alkyl), $-C(=O)NH_2$, $-C(=O)N(C_{1-6}$ alkyl$)_2$, $-OC(=O)NH(C_{1-6}$ alkyl), $-NHC(=O)(C_{1-6}$ alkyl), $-N(C_{1-6}$ alkyl$)C(=O)(C_{1-6}$ alkyl), $-NHCO_2(C_{1-6}$ alkyl), $-NHC(=O)N(C_{1-6}$ alkyl$)_2$, $-NHC(=O)NH(C_{1-6}$ alkyl), $-NHC(=O)NH_2$, $-C(=NH)O(C_{1-6}$ alkyl), $-OC(=NH)(C_{1-6}$ alkyl), $-OC(=NH)OC_{1-6}$ alkyl, $-C(=NH)N(C_{1-6}$ alkyl$)_2$, $-C(=NH)NH(C_{1-6}$ alkyl), $-C(=NH)NH_2$, $-OC(=NH)N(C_{1-6}$ alkyl$)_2$, $-OC(NH)NH(C_{1-6}$ alkyl), $-OC(NH)NH_2$, $-NHC(NH)N(C_{1-6}$ alkyl$)_2$, $-NHC(=NH)NH_2$, $-NHSO_2(C_{1-6}$ alkyl), $-SO_2N(C_{1-6}$ alkyl$)_2$, $-SO_2NH(C_{1-6}$ alkyl), $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl$)_3$, $-OSi(C_{1-6}$ alkyl$)_3$, $-C(=S)N(C_{1-6}$ alkyl$)_2$, $C(=S)NH(C_{1-6}$ alkyl), $C(=S)NH_2$, $-C(=O)S(C_{1-6}$ alkyl), $-C(=S)SC_{1-6}$ alkyl, $-SC(=S)SC_{1-6}$ alkyl, $-P(=O)_2(C_{1-6}$ alkyl), $-P(=O)(C_{1-6}$ alkyl$)_2$, $-OP(=O)(C_{1-6}$ alkyl$)_2$, $-OP(=O)(OC_{1-6}$ alkyl$)_2$, $C_{1-6}$ alkyl, $C_{1-6}$ haloalkyl, $C_2$-$C_6$ alkenyl, $C_2$-$C_6$ alkynyl, $C_3$-$C_7$ carbocyclyl, $C_6$-$C_{10}$ aryl, $C_3$-$C_7$ heterocyclyl, $C_5$-$C_{10}$ heteroaryl; or two geminal $R^{gg}$ substituents may combine to form =O or =S; wherein $X^-$ is a counterion.

Exemplary substituents on nitrogen atoms include, but are not limited to, hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{bb})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, alkyl, haloalkyl, alkenyl, alkynyl, carbocyclyl, heterocyclyl, aryl and heteroaryl, or two $R^{cc}$ groups attached to a nitrogen atom combine to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{dd}$ groups, and wherein $R^{aa}$, $R^{bb}$, $R^{cc}$ and $R^{dd}$ are as described herein.

Other Definitions

As used herein, "cancer" refers to any disease induced or caused by inappropriately high levels of cell division, inappropriately low levels of apoptosis, or both. Examples of cancer include, but are not limited to, leukemias (e.g., acute leukemia, acute lymphoblastic leukemia, acute myeloid leukemia, acute myelogenous leukemia, acute promyelocytic leukemia, acute myelomonocytic leukemia, acute monocytic leukemia, acute erythrocytic leukemia, chronic leukemia, chronic myelogenous leukemia, chronic lymphocytic leukemia), polycythemia vera, lymphoma (Hodgkin's disease, non-Hodgkin's disease), Waldenstrom's Macroglobulinemia, heavy chain disease and solid tumors.

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term "pharmaceutically acceptable" as used herein refers to the substance, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The term "salt" refers to a relatively non-toxic addition salt of inorganic and organic acids to the compounds of the present disclosure. These salts can be prepared in situ during the final separation and purification of the compounds, or by isolating salts produced by separately reacting the purified compound in the free base form with a suitable organic or inorganic acid.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N, N'-dibenzylethylenediamine, chloroprocaine, choline, diethanolamine, ethylenediamine, N-methylglucamine and procaine.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., "Pharmaceutical Salts," J. Pharm. Sci., 1977; 66: 1-19 for reference).

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "human", "patient" and "subject" can be used interchangeably herein.

"Disease," "disorder," and "condition" can be used interchangeably herein.

Unless indicated, otherwise the term "treatment" as used herein includes the effect on a subject who is suffering from a particular disease, disorder, or condition, which reduces the severity of the disease, disorder, or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a compound refers to an amount sufficient to elicit a target biological response. As understood by those skilled in the art, the effective amount of the compound of the disclosure can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

Unless indicated, otherwise the "therapeutically effective amount" of the compound as used herein is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless indicated, otherwise the "prophylactically effective amount" of the compound as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the compounds of the present disclosure and other therapeutic agents. For example, the compounds of the present disclosure can be administered simultaneously or sequentially in separate unit dosage with other therapeutic agents, or simultaneously in a single unit dosage with other therapeutic agents.

DETAILED DESCRIPTION OF THE INVENTION

As used herein, "compounds of the present disclosure" refer to the compounds of general formula (I) (and subformulae thereof) below, or pharmaceutically acceptable salts, enantiomers, diastereomers, racemates, solvates, hydrates, polymorphs, prodrugs or isotope variants thereof, and mixtures thereof.

Compounds are generally described herein using standard nomenclature. It should be understood, unless otherwise specified, that compounds with asymmetric center(s) include all optical isomers and mixtures thereof. Furthermore, unless otherwise specified, all isomer compounds and carbon-carbon double bonds included in the present disclosure may be in the form of Z and E. Compounds which exist in different tautomeric forms, one of which is not limited to any particular tautomer, but is intended to cover all tautomeric forms.

In one embodiment, the present disclosure refers to a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (X):

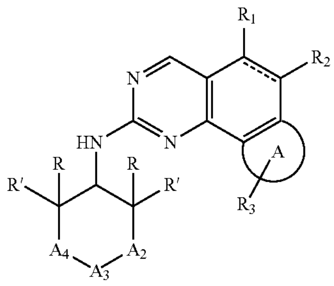

(X)

wherein:

indicates a single bond or a double bond;

ring A is a 5- to 6-membered heteroaryl; alternatively selected from pyrrolyl, furyl, thienyl, imidazolyl, pyrazolyl, oxazolyl, isoxazolyl, thiazolyl, isothiazolyl, triazolyl, oxadiazolyl and thiadiazolyl; alternatively selected from:

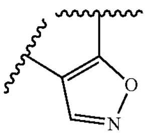
and
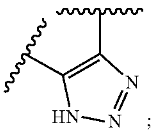
;

$A_2$ is CRR' or NR";
$A_3$ is CRR' or $NR_4$;
$A_4$ is CRR' or NR";
or $A_3$, $A_4$ and substituents thereon are combined to form $C_{6-10}$ aryl or 5- to 10-membered heteroaryl;
R and R' are independently selected from H, D, —$OR_{O1}$, —$NR_{N1}R_{N2}$, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;
$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;
$R_2$ is selected from H, D, halogen, —CN, —$OR_a$, —$SR_a$, —$NR_bR_c$, —C(O)$R_a$, —C(O)$OR_a$, —C(O)$NR_bR_c$, —$C_{0-6}$ alkylene-$OR_5$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;
$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;
$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;
$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;
$R_{O1}$, $R_{N1}$ and $R_{N2}$ are independently selected from H, $C_{1-6}$ alkyl, $C_{1-6}$ haloalkyl, —C(O)$R_d$, —S(O)$_mR_d$, —$C_{1-6}$ alkylene-$OR_5$, —$C_{1-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;
or $R_{N1}$ and $R_{N2}$ are taken together with the nitrogen atom to which they are attached to form 3- to 7-membered heterocyclyl or 5- to 10-membered heteroaryl, which is optionally substituted by 1, 2 or 3 $R_8$ groups;
$R_4$ and R" are independently selected from H, $C_{1-6}$ alkyl, $C_{1-6}$ haloalkyl, $C_{2-6}$ alkenyl, $C_{2-6}$ alkynyl, —C(O)$R_d$, —S(O)$_mR_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;
$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;
m is 0, 1 or 2;
$R_5$, $R_6$ and $R_7$ are independently selected from H, $C_{1-6}$ alkyl and $C_{1-6}$ haloalkyl;
$R_8$ is independently selected from H, D, halogen, —CN, -L-$C_{3-7}$ cycloalkyl, -L-3- to 7-membered heterocyclyl, -L-$C_{6-10}$ aryl and -L-5- to 10-membered heteroaryl;
L is selected from a chemical bond, —C(O)—, —C(O)NH—, —$C_{1-6}$ alkylene-, —$C_{2-6}$ alkenylene- and —$C_{2-6}$ alkynylene-; and
$R_8$ is further substituted by H, D, halogen, —CN, $C_{1-6}$ alkyl or $C_{1-6}$ haloalkyl.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I):

(I)

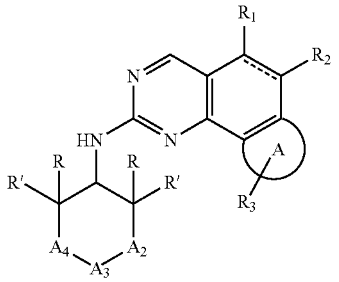

wherein:
⎓ indicates a single bond or a double bond;
ring A is a 5- to 6-membered heteroaryl; alternatively selected from pyrrolyl, furyl, thienyl, imidazolyl, pyrazolyl, oxazolyl, isoxazolyl, thiazolyl, isothiazolyl, triazolyl, oxadiazolyl and thiadiazolyl; alternatively selected from:

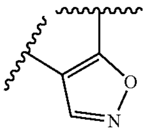
and
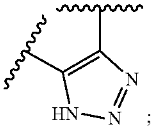
;

$A_2$ is CRR' or NR";
$A_3$ is CRR' or $NR_4$;
$A_4$ is CRR' or NR";
or $A_3$, $A_4$ and substituents thereon are combined to form $C_{6-10}$ aryl or 5- to 10-membered heteroaryl;
R and R' are independently selected from H, D, —$OR_{O1}$, —$NR_{N1}R_{N2}$, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_{O1}$, $R_{N1}$ and $R_{N2}$ are independently selected from H, $C_{1-6}$ alkyl, $C_{1-6}$ haloalkyl, —C(O)$R_d$, —S(O)$_mR_d$, —$C_{1-6}$ alkylene-$OR_5$, —$C_{1-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

or $R_{N1}$ and $R_{N2}$ are taken together with the nitrogen atom to which they are attached to form 3- to 7-membered heterocyclyl or 5- to 10-membered heteroaryl, which is optionally substituted by 1, 2 or 3 $R_8$ groups;

$R_4$ and R" are independently selected from H, $C_{1-6}$ alkyl, $C_{1-6}$ haloalkyl, $C_{2-6}$ alkenyl, $C_{2-6}$ alkynyl, —C(O)$R_d$, —S(O)$_mR_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl;

$R_8$ is independently selected from H, D, halogen, —CN, -L-$C_{3-7}$ cycloalkyl, -L-3- to 7-membered heterocyclyl, -L-$C_{6-10}$ aryl and -L-5- to 10-membered heteroaryl;

L is selected from a chemical bond, —C(O)—, —C(O)NH—, —$C_{1-6}$ alkylene-, —$C_{2-6}$ alkenylene- and —$C_{2-6}$ alkynylene-; and $R_8$ is further substituted by H, D, halogen, —CN, $C_{1-6}$ alkyl or $C_{1-6}$ haloalkyl.

----

In one embodiment, ---- indicates a single bond; in another embodiment, ---- indicates a double bond.

Ring A

In one embodiment, ring A is a 5- to 6-membered heteroaryl; in another embodiment, ring A is selected from pyrrolyl, furyl, thienyl, imidazolyl, pyrazolyl, oxazolyl, isoxazolyl, thiazolyl, isothiazolyl, triazolyl, oxadiazolyl and thiadiazolyl; in another embodiment, ring A is selected from:

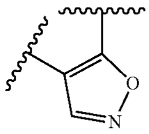
and
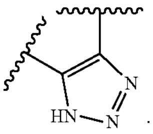
.

$A_2$, $A_3$ and $A_4$

In one embodiment, $A_2$ is CRR'; in another embodiment, $A_2$ is NR".

In one embodiment, $A_3$ is CRR'; in another embodiment, $A_3$ is $NR_4$.

In one embodiment, $A_4$ is CRR'; in another embodiment, $A_4$ is NR".

In another embodiment, $A_3$, $A_4$ and substituents thereon are combined to form $C_{6-10}$ aryl; in another embodiment, $A_3$, $A_4$ and substituents thereon are combined to form 5- to 10-membered heteroaryl.

R and R'

In one embodiment, R is H; in another embodiment, R is D; in another embodiment, R is —$OR_{O1}$; in another embodiment, R is —$NR_{N1}R_{N2}$; in another embodiment, R is $C_{1-6}$ alkyl; in another embodiment, R is $C_{1-6}$ haloalkyl; in another embodiment, R is —$C_{0-6}$ alkylene-$C_{3-7}$ cycloalkyl; in another embodiment, R is —$C_{0-6}$ alkylene-3- to 7-membered heterocyclyl; in another embodiment, R is —$C_{0-6}$ alkylene-$C_{6-10}$ aryl; in another embodiment, R is —$C_{0-6}$ alkylene-5- to 10-membered heteroaryl.

In one embodiment, R' is H; in another embodiment, R' is D; in another embodiment, R' is —$OR_{O1}$; in another embodiment, R' is —$NR_{N1}R_{N2}$; in another embodiment, R' is $C_{1-6}$ alkyl; in another embodiment, R' is $C_{1-6}$ haloalkyl; in another embodiment, R' is —$C_{0-6}$ alkylene-$C_{3-7}$ cycloalkyl; in another embodiment, R' is —$C_{0-6}$ alkylene-3- to 7-membered heterocyclyl; in another embodiment, R' is —$C_{0-6}$ alkylene-$C_{6-10}$ aryl; in another embodiment, R' is —$C_{0-6}$ alkylene-5- to 10-membered heteroaryl.

In another embodiment, R, R' and the carbon atom attached thereto are combined to form C═O.

$R_1$

In one embodiment, $R_1$ is H; in another embodiment, $R_1$ is D; in another embodiment, $R_1$ is halogen; in another embodiment, $R_1$ is —CN; in another embodiment, $R_1$ is —$OR_a$; in another embodiment, $R_1$ is —$SR_a$; in another embodiment, $R_1$ is —$NR_bR_c$; in another embodiment, $R_1$ is —C(O)$R_a$; in another embodiment, $R_1$ is —C(O)$OR_a$; in another embodiment, $R_1$ is —C(O)$NR_bR_c$; in another embodiment, $R_1$ is $C_{1-6}$ alkyl; in another embodiment, $R_1$ is $C_{1-6}$ haloalkyl; in another embodiment, $R_1$ is $C_{3-7}$ cycloalkyl; in another embodiment, $R_1$ is 3- to 7-membered heterocyclyl; in another embodiment, $R_1$ is $C_{6-10}$ aryl; in another embodiment, $R_1$ is 5- to 10-membered heteroaryl; in another embodiment, the $C_{3-7}$ cycloalkyl or 3- to 7-membered heterocyclyl in $R_1$ is optionally substituted by oxo or thioxo.

$R_2$

In one embodiment, $R_2$ is H; in another embodiment, $R_2$ is D; in another embodiment, $R_2$ is halogen; in another embodiment, $R_2$ is —CN; in another embodiment, $R_2$ is —$OR_a$; in another embodiment, $R_2$ is —$SR_a$; in another embodiment, $R_2$ is —$NR_bR_c$; in another embodiment, $R_2$ is —$C(O)R_a$; in another embodiment, $R_2$ is —$C(O)OR_a$; in another embodiment, $R_2$ is —$C(O)NR_bR_c$; in another embodiment, $R_2$ is —$C_{0-6}$ alkylene-$OR_5$; in another embodiment, $R_2$ is $C_{1-6}$ alkyl; in another embodiment, $R_2$ is $C_{1-6}$ haloalkyl; in another embodiment, $R_2$ is $C_{3-7}$ cycloalkyl; in another embodiment, $R_2$ is 3- to 7-membered heterocyclyl; in another embodiment, $R_2$ is $C_{6-10}$ aryl; in another embodiment, $R_2$ is 5- to 10-membered heteroaryl; in another embodiment, the $C_{3-7}$ cycloalkyl or 3- to 7-membered heterocyclyl in $R_2$ is optionally substituted by oxo or thioxo.

$R_3$

In one embodiment, $R_3$ is $C_{1-6}$ alkyl; in another embodiment, $R_3$ is $C_{1-6}$ haloalkyl; in another embodiment, $R_3$ is —$C_{0-6}$ alkylene-$C_{3-7}$ cycloalkyl; in another embodiment, $R_3$ is —$C_{0-6}$ alkylene-3- to 7-membered heterocyclyl; in another embodiment, $R_3$ is —$C_{0-6}$ alkylene-$C_{6-10}$ aryl; in another embodiment, $R_3$ is —$C_{0-6}$ alkylene-5- to 10-membered heteroaryl; in another embodiment, the $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl in $R_3$ may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl.

$R_a$

In one embodiment, $R_a$ is H; in another embodiment, $R_a$ is $C_{1-6}$ alkyl; in another embodiment, $R_a$ is $C_{2-6}$ alkenyl; in another embodiment, $R_a$ is $C_{2-6}$ alkynyl; in another embodiment, $R_a$ is $C_{1-6}$ haloalkyl; in another embodiment, $R_a$ is —$C_{0-6}$ alkylene-$C_{3-7}$ cycloalkyl; in another embodiment, $R_a$ is —$C_{0-6}$ alkylene-3- to 7-membered heterocyclyl; in another embodiment, $R_a$ is —$C_{0-6}$ alkylene-$C_{6-10}$ aryl; in another embodiment, $R_a$ is —$C_{0-6}$ alkylene-5- to 10-membered heteroaryl.

$R_b$ and $R_c$

In one embodiment, $R_b$ is H; in another embodiment, $R_b$ is $C_{1-6}$ alkyl; in another embodiment, $R_b$ is $C_{2-6}$ alkenyl; in another embodiment, $R_b$ is $C_{2-6}$ alkynyl; in another embodiment, $R_b$ is $C_{1-6}$ haloalkyl; in another embodiment, $R_b$ is —$C_{0-6}$ alkylene-$C_{3-7}$ cycloalkyl; in another embodiment, $R_b$ is —$C_{0-6}$ alkylene-3- to 7-membered heterocyclyl; in another embodiment, $R_b$ is —$C_{0-6}$ alkylene-$C_{6-10}$ aryl; in another embodiment, $R_b$ is —$C_{0-6}$ alkylene-5- to 10-membered heteroaryl.

In one embodiment, $R_c$ is H; in another embodiment, $R_c$ is $C_{1-6}$ alkyl; in another embodiment, $R_c$ is $C_{2-6}$ alkenyl; in another embodiment, $R_c$ is $C_{2-6}$ alkynyl; in another embodiment, $R_c$ is $C_{1-6}$ haloalkyl; in another embodiment, $R_c$ is —$C_{0-6}$ alkylene-$C_{3-7}$ cycloalkyl; in another embodiment, $R_c$ is —$C_{0-6}$ alkylene-3- to 7-membered heterocyclyl; in another embodiment, $R_c$ is —$C_{0-6}$ alkylene-$C_{6-10}$ aryl; in another embodiment, R, is —$C_{0-6}$ alkylene-5- to 10-membered heteroaryl.

In another embodiment, $R_b$ and $R_c$ are taken together with the nitrogen atom to which they are attached to form 3- to 7-membered heterocyclyl; in another embodiment, $R_b$ and $R_c$ are taken together with the nitrogen atom to which they are attached to form 5- to 6-membered heteroaryl.

$R_{O1}$, $R_{N1}$ and $R_{N2}$

In one embodiment, $R_{O1}$ is H; in another embodiment, $R_{O1}$ is $C_{1-6}$ alkyl; in another embodiment, $R_{O1}$ is $C_{1-6}$ haloalkyl; in another embodiment, $R_{O1}$ is —$C(O)R_d$; in another embodiment, $R_{O1}$ is —$S(O)_mR_d$; in another embodiment, $R_{O1}$ is —$C_{1-6}$ alkylene-$OR_5$; in another embodiment, $R_{O1}$ is —$C_{1-6}$ alkylene-$NR_6R_7$; in another embodiment, $R_{O1}$ is —$C_{0-6}$ alkylene-$C_{3-7}$ cycloalkyl; in another embodiment, $R_{O1}$ is —$C_{0-6}$ alkylene-3- to 7-membered heterocyclyl; in another embodiment, $R_{O1}$ is —$C_{0-6}$ alkylene-$C_{6-10}$ aryl; in another embodiment, $R_{O1}$ is —$C_{0-6}$ alkylene-5- to 10-membered heteroaryl.

In one embodiment, $R_{N1}$ is H; in another embodiment, $R_{N1}$ is $C_{1-6}$ alkyl; in another embodiment, $R_{N1}$ is $C_{1-6}$ haloalkyl; in another embodiment, $R_{N1}$ is —$C(O)R_d$; in another embodiment, $R_{N1}$ is —$S(O)_mR_d$; in another embodiment, $R_{N1}$ is —$C_{1-6}$ alkylene-$OR_5$; in another embodiment, $R_{N1}$ is —$C_{1-6}$ alkylene-$NR_6R_7$; in another embodiment, $R_{N1}$ is —$C_{0-6}$ alkylene-$C_{3-7}$ cycloalkyl; in another embodiment, $R_{N1}$ is —$C_{0-6}$ alkylene-3- to 7-membered heterocyclyl; in another embodiment, $R_{N1}$ is —$C_{0-6}$ alkylene-$C_{6-10}$ aryl; in another embodiment, $R_{N1}$ is —$C_{0-6}$ alkylene-5- to 10-membered heteroaryl.

In one embodiment, $R_{N2}$ is H; in another embodiment, $R_{N2}$ is $C_{1-6}$ alkyl; in another embodiment, $R_{N2}$ is $C_{1-6}$ haloalkyl; in another embodiment, $R_{N2}$ is —$C(O)R_d$; in another embodiment, $R_{N2}$ is —$S(O)_mR_d$; in another embodiment, $R_{N2}$ is —$C_{1-6}$ alkylene-$OR_5$; in another embodiment, $R_{N2}$ is —$C_{1-6}$ alkylene-$NR_6R_7$; in another embodiment, $R_{N2}$ is —$C_{0-6}$ alkylene-$C_{3-7}$ cycloalkyl; in another embodiment, $R_{N2}$ is —$C_{0-6}$ alkylene-3- to 7-membered heterocyclyl; in another embodiment, $R_{N2}$ is —$C_{0-6}$ alkylene-$C_{6-10}$ aryl; in another embodiment, $R_{N2}$ is —$C_{0-6}$ alkylene-5- to 10-membered heteroaryl.

In another embodiment, $R_{N1}$ and $R_{N2}$ are taken together with the nitrogen atom to which they are attached to form 3- to 7-membered heterocyclyl, which is optionally substituted by 1, 2 or 3 $R_8$ groups; in another embodiment, $R_{N1}$ and $R_{N2}$ are taken together with the nitrogen atom to which they are attached to form 5- to 10-membered heteroaryl, which is optionally substituted by 1, 2 or 3 $R_8$ groups.

$R_4$ and R"

In one embodiment, $R_4$ is H; in another embodiment, $R_4$ is $C_{1-6}$ alkyl; in another embodiment, $R_4$ is $C_{1-6}$ haloalkyl; in another embodiment, $R_4$ is $C_{2-6}$ alkenyl; in another embodiment, $R_4$ is $C_{2-6}$ alkynyl; in another embodiment, $R_4$ is —$C(O)R_d$; in another embodiment, $R_4$ is —$S(O)_mR_d$; in another embodiment, $R_4$ is —$C_{0-6}$ alkylene-$C_{3-7}$ cycloalkyl; in another embodiment, $R_4$ is —$C_{0-6}$ alkylene-3- to 7-membered heterocyclyl; in another embodiment, $R_4$ is —$C_{0-6}$ alkylene-$C_{6-10}$ aryl; in another embodiment, $R_4$ is —$C_{0-6}$ alkylene-5- to 10-membered heteroaryl.

In one embodiment, R" is H; in another embodiment, R" is $C_{1-6}$ alkyl; in another embodiment, R" is $C_{1-6}$ haloalkyl; in another embodiment, R" is $C_{2-6}$ alkenyl; in another embodiment, R" is $C_{2-6}$ alkynyl; in another embodiment, R" is —$C(O)R_d$; in another embodiment, R" is —$S(O)_mR_d$; in another embodiment, R" is —$C_{0-6}$ alkylene-$C_{3-7}$ cycloalkyl; in another embodiment, R" is —$C_{0-6}$ alkylene-3- to 7-membered heterocyclyl; in another embodiment, R" is —$C_{0-6}$ alkylene-$C_{6-10}$ aryl; in another embodiment, R" is —$C_{0-6}$ alkylene-5- to 10-membered heteroaryl.

$R_d$

In one embodiment, $R_d$ is $C_{1-6}$ alkyl; in another embodiment, $R_d$ is $C_{1-6}$ haloalkyl; in another embodiment, $R_d$ is —$C_{0-6}$ alkylene-$OR_5$; in another embodiment, $R_d$ is —$C_{0-6}$ alkylene-$NR_6R_7$; in another embodiment, $R_d$ is —$C_{0-6}$ alkylene-$C_{3-7}$ cycloalkyl; in another embodiment, $R_d$ is —$C_{0-6}$ alkylene-3- to 7-membered heterocyclyl; in another embodiment, $R_d$ is —$C_{0-6}$ alkylene-$C_{6-10}$ aryl; in another embodiment, $R_d$ is —$C_{0-6}$ alkylene-5- to 10-membered heteroaryl.

m

In one embodiment, m is 0; in another embodiment, m is 1; in another embodiment, m is 2.

$R_5$, $R_6$ and $R_7$

In one embodiment, $R_5$ is H; in another embodiment, $R_5$ is $C_{1-6}$ alkyl; in another embodiment, $R_5$ is $C_{1-6}$ haloalkyl.

In one embodiment, $R_6$ is H; in another embodiment, $R_6$ is $C_{1-6}$ alkyl; in another embodiment, $R_6$ is $C_{1-6}$ haloalkyl.

In one embodiment, $R_7$ is H; in another embodiment, $R_7$ is $C_{1-6}$ alkyl; in another embodiment, $R_7$ is $C_{1-6}$ haloalkyl.

$R_8$

In one embodiment, $R_8$ is H; in another embodiment, $R_8$ is D; in another embodiment, $R_8$ is halogen; in another embodiment, $R_8$ is —CN; in another embodiment, $R_8$ is -L-$C_{3-7}$ cycloalkyl; in another embodiment, $R_8$ is -L-3- to 7-membered heterocyclyl; in another embodiment, $R_8$ is -L-$C_{6-10}$ aryl; in another embodiment, $R_8$ is -L-5- to 10-membered heteroaryl.

In one embodiment, $R_8$ is further substituted by H; in one embodiment, $R_8$ is further substituted by D; in one embodiment, $R_8$ is further substituted by halogen; in one embodiment, $R_8$ is further substituted by —CN; in one embodiment, $R_8$ is further substituted by $C_{1-6}$ alkyl; in one embodiment, $R_8$ is further substituted by $C_{1-6}$ haloalkyl.

L

In one embodiment, L is a chemical bond; in another embodiment, L is —C(O)—; in another embodiment, L is —C(O)NH—; in another embodiment, L is —$C_{1-6}$ alkylene-; in another embodiment, L is —$C_{2-6}$ alkenylene-; in another embodiment, L is —$C_{2-6}$ alkynylene-.

Any technical solution in any one of the above embodiments, or any combination thereof, may be combined with any technical solution in any one of the above embodiments, or any combination thereof. For example, any technical solution of $A_2$, or any combination thereof, may be combined with any technical solution of $A_3$, $A_4$, $R_1$—$R_8$, R, R', $R_a$, $R_b$, $R_c$, $R_d$, L and m, etc or any combination thereof. The present disclosure is intended to include all combination of such technical solutions, which are not exhaustively listed here to save space.

In a specific embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-1) or (II-1):

(I-1)

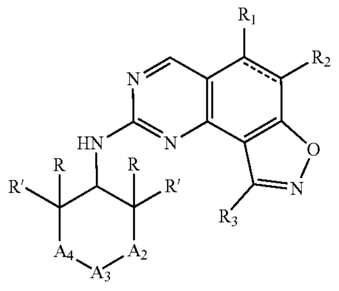

or

-continued (II-1)

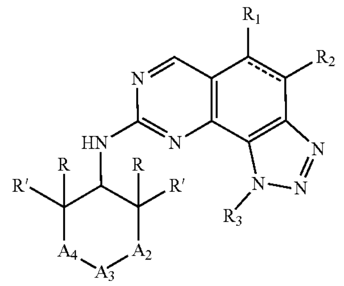

wherein each group is as defined above.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-2) or (II-2):

(I-2)

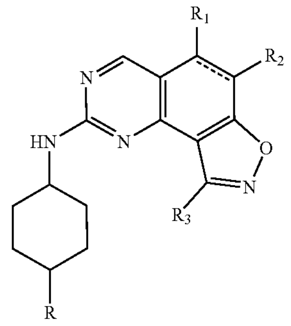

or (II-2)

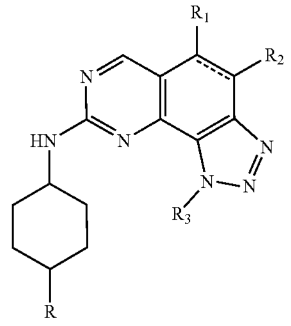

wherein:

⎓ indicates a single bond or a double bond;

$R_1$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, —$OR_a$, —$SR_a$, —$NR_bR_c$, —$C(O)R_a$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; R is —$OR_{O1}$ or —$NR_{N1}R_{N2}$;

$R_{O1}$, $R_{N1}$ and $R_{N2}$ are independently selected from H, $C_{1-6}$ alkyl, $C_{1-6}$ haloalkyl, —$C(O)R_d$, —$S(O)_mR_d$, —$C_{1-6}$ alkylene-$OR_5$, —$C_{1-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

or $R_{N1}$ and $R_{N2}$ are taken together with the nitrogen atom to which they are attached to form 3- to 7-membered heterocyclyl or 5- to 10-membered heteroaryl, which is optionally substituted by 1, 2 or 3 $R_8$ groups;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl;

$R_8$ is independently selected from H, D, halogen, —CN, -L-$C_{3-7}$ cycloalkyl, -L-3- to 7-membered heterocyclyl, -L-$C_{6-10}$ aryl and -L-5- to 10-membered heteroaryl;

L is selected from a chemical bond, —C(O)—, —C(O)NH—, —$C_{1-6}$ alkylene-, —$C_{2-6}$ alkenylene- and —$C_{2-6}$ alkynylene-; and $R_8$ is further substituted by H, D, halogen, —CN, $C_{1-6}$ alkyl or $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

$\overline{----}$ indicates a single bond or a double bond;

$R_1$ is selected from H, D, halogen, —CN, —$OR_a$, —$SR_a$ and —$NR_bR_c$;

$R_2$ is selected from H, D, halogen, —CN, —$OR_a$, —$SR_a$ and —$NR_bR_c$;

$R_3$ is selected from $C_{1-6}$ alkyl, $C_{1-6}$ haloalkyl, —$C_{0-6}$ alkylene-$C_{3-7}$ cycloalkyl and —$C_{0-6}$ alkylene-3- to 7-membered heterocyclyl;

R is —$OR_{O1}$ or —$NR_{N1}R_{N2}$;

$R_{O1}$, $R_{N1}$ and $R_{N2}$ are independently selected from H, $C_{1-6}$ alkyl, $C_{1-6}$ haloalkyl, —$C(O)R_d$, —$S(O)_mR_d$, —$C_{1-6}$ alkylene-$OR_5$, —$C_{1-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

or $R_{N1}$ and $R_{N2}$ are taken together with the nitrogen atom to which they are attached to form 3- to 7-membered heterocyclyl or 5- to 10-membered heteroaryl, which is optionally substituted by 1, 2 or 3 $R_8$ groups;

$R_d$ is selected from $C_{1-6}$ alkyl, $C_{1-6}$ haloalkyl, —$C_{0-6}$ alkylene-$OR_5$ and —$C_{0-6}$ alkylene-$NR_6R_2$;

m is 0, 1 or 2;

$R_5$, $R_6$ and $R_7$ are independently selected from H, $C_{1-6}$ alkyl and $C_{1-6}$ haloalkyl;

$R_8$ is independently selected from H, D, halogen, —CN, -L-$C_{3-7}$ cycloalkyl, -L-3- to 7-membered heterocyclyl, -L-$C_{6-10}$ aryl and -L-5- to 10-membered heteroaryl;

L is selected from a chemical bond, —C(O)—, —C(O)NH—, —$C_{1-6}$ alkylene-, —$C_{2-6}$ alkenylene- and —$C_{2-6}$ alkynylene-; and $R_8$ is further substituted by H, D, halogen, —CN, $C_{1-6}$ alkyl or $C_{1-6}$ haloalkyl.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-2) or (II-2):

(I-2)

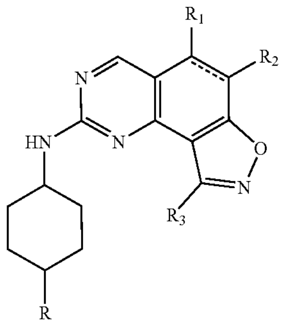

or (II-2)

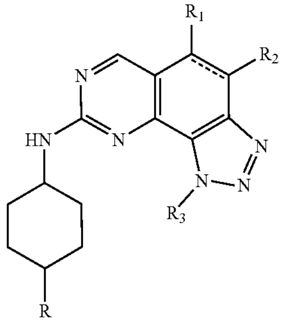

wherein:

$\overline{----}$ indicates a single bond or a double bond;

$R_1$ is H, D, halogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_2$, $C_{1-6}$ alkyl and $C_{1-6}$ haloalkyl; R is —$NR_{N1}R_{N2}$;

$R_{N1}$ is selected from H, $C_{1-6}$ alkyl and $C_{1-6}$ haloalkyl;

$R_{N2}$ is selected from $C_{1-6}$ alkyl, $C_{1-6}$ haloalkyl, —$S(O)_mR_d$, —$C(O)R_d$, —$C_{1-6}$ alkylene-$OR_5$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, or halogen;

$R_2$ is selected from H, D, and halogen;

$R_3$ is selected from $C_{1-6}$ alkyl and $C_{1-6}$ haloalkyl;

R is —$NR_{N1}R_{N2}$;

$R_{N1}$ is selected from H, $C_{1-6}$ alkyl and $C_{1-6}$ haloalkyl;

$R_{N2}$ is selected from $C_{1-6}$ alkyl, $C_{1-6}$ haloalkyl, —$S(O)_mR_d$, —$C_{1-6}$ alkylene-$OR_5$, and -3- to 7-membered heterocyclyl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H;

$R_2$ is H;

$R_3$ is $C_{1-6}$ alkyl;

R is —$NR_{N1}R_{N2}$;

$R_{N1}$ is selected from H and $C_{1-6}$ alkyl, alternatively $R_{N1}$ is H or Me;

$R_{N2}$ is selected from $C_{1-6}$ alkyl, —$S(O)_mR_d$, —$C_{0-6}$ alkylene-$OR_5$,

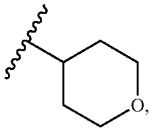, and 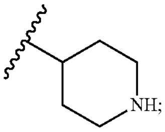;

alternatively Me, —$S(O)_2Me$, —$CH_2CH_2$—$OCH_3$,

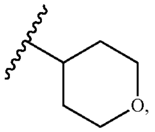, and 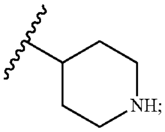;

$R_d$ is $C_{1-6}$ alkyl;

m is 2;

$R_5$ is selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, halogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_2$, $C_{1-6}$ alkyl and $C_{1-6}$ haloalkyl;

R is —$NR_{N1}R_{N2}$;

$R_{N1}$ is H;

$R_{N2}$ is selected from —$S(O)_mR_d$ and —$C(O)R_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, halogen, $C_{1-6}$ alkyl, or $C_{1-6}$ haloalkyl;

$R_2$ is selected from H, D, halogen, $C_{1-6}$ alkyl, and $C_{1-6}$ haloalkyl;

$R_3$ is selected from $C_{1-6}$ alkyl and $C_{1-6}$ haloalkyl;

R is —$NR_{N1}R_{N2}$;

$R_{N1}$ is H;

$R_{N2}$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, or halogen;

$R_2$ is selected from H, D, and halogen;

$R_3$ is selected from $C_{1-6}$ alkyl and $C_{1-6}$ haloalkyl;

R is —$NR_{N1}R_{N2}$;

$R_{N1}$ is H;

$R_{N2}$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, and —$C_{0-6}$ alkylene-3- to 7-membered heterocyclyl, m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H;

$R_2$ is H;

$R_3$ is $C_{1-6}$ alkyl;

R is —$NR_{N1}R_{N2}$;

$R_{N1}$ is H;

$R_{N2}$ is —$S(O)_mR_d$; alternatively —$S(O)_2Me$;

$R_d$ is $C_{1-6}$ alkyl;

m is 2.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-3), (I-3-1), (I-3-2), (II-3), (II-3-1) or (II-3-2):

(I-3)

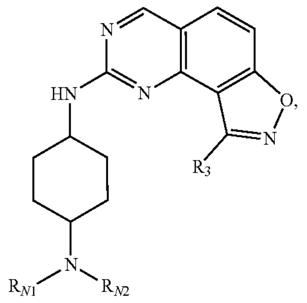

(I-3-1)

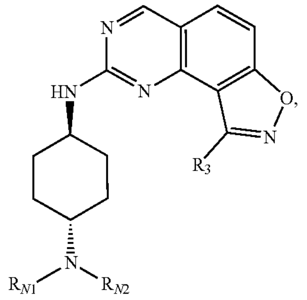

(I-3-2)

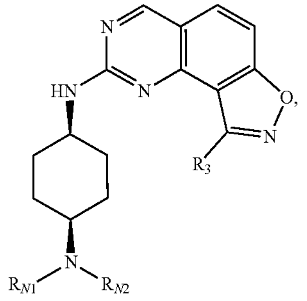

(II-3)

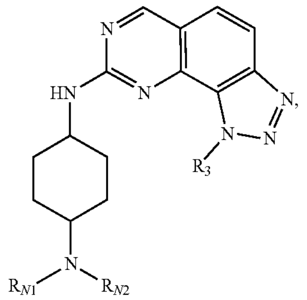

-continued (II-3-1)

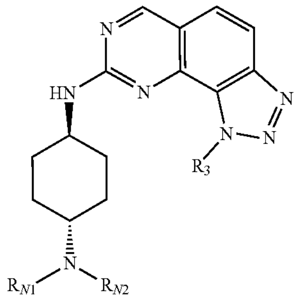

or (II-3-2)

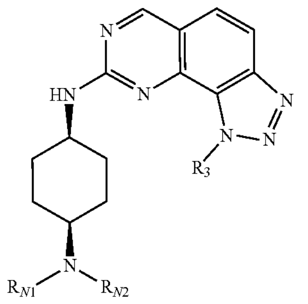

wherein $R_3$, $R_{N1}$ and $R_{N2}$ are as defined above.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-3), (I-3-1), (I-3-2), (II-3), (II-3-1) or (II-3-2):

(II-3)

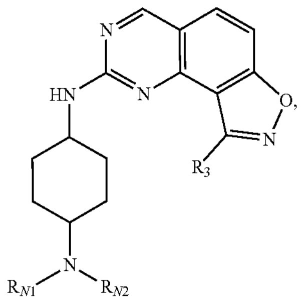

(I-3-1)

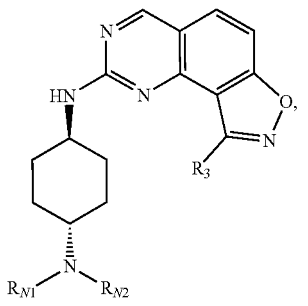

-continued (I-3-2)

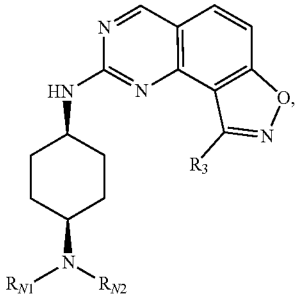

(II-3)

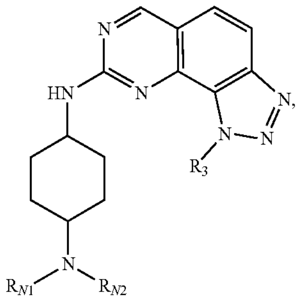

(II-3-1)

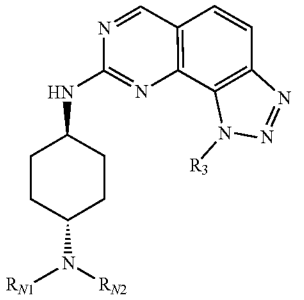

or (II-3-2)

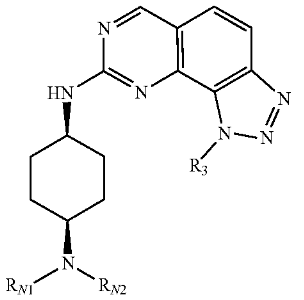

wherein:

$R_3$ is $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_{N1}$ and $R_{N2}$ are independently selected from H, $C_{1-6}$ alkyl, $C_{1-6}$ haloalkyl, —C(O)$R_d$, —S(O)$_m R_d$, —$C_{1-6}$ alkylene-$OR_5$, —$C_{1-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; alternatively selected from: H, Me, —S(O)$_2$Me, —$CH_2CH_2OCH_3$,

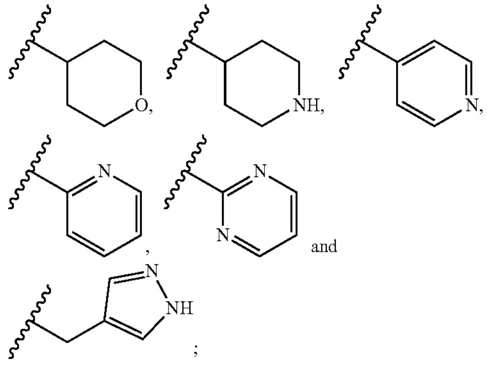

, and ;

or $R_{N1}$ and $R_{N2}$ are taken together with the nitrogen atom to which they are attached to form 3- to 7-membered heterocyclyl and 5- to 10-membered heteroaryl, which is optionally substituted by 1, 2 or 3 $R_8$ groups; alternatively selected from:

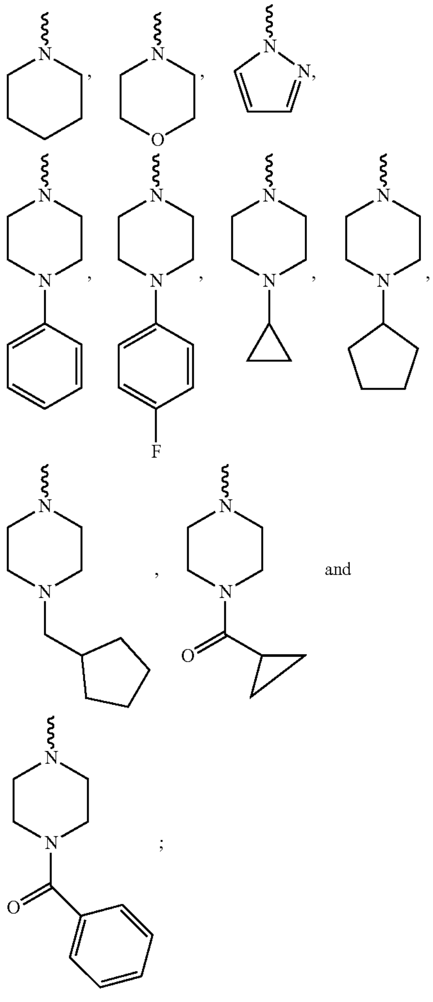

, , , , , , , and ;

$R_d$ is selected from $C_{1-6}$ alkyl and $C_{1-6}$ haloalkyl;

m is 0, 1 or 2;

$R_5$, $R_6$ and $R_7$ are independently selected from H, $C_{1-6}$ alkyl and $C_{1-6}$ haloalkyl;

$R_8$ is independently selected from H, D, -L-$C_{3-7}$ cycloalkyl, -L-3- to 7-membered heterocyclyl, -L-$C_{6-10}$ aryl and -L-5- to 10-membered heteroaryl;

L is selected from a chemical bond, —C(O)—, —C(O)NH—, —$C_{1-6}$ alkylene-, —$C_{2-6}$ alkenylene- and —$C_{2-6}$ alkynylene-; and $R_8$ is further substituted by H, D, halogen, —CN, $C_{1-6}$ alkyl or $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

$R_3$ is $C_{1-6}$ alkyl, $C_{1-6}$ haloalkyl, —$C_{0-6}$ alkylene-$C_{3-7}$ cycloalkyl or —$C_{0-6}$ alkylene-3- to 7-membered heterocyclyl;

$R_{N1}$ is selected from H, $C_{1-6}$ alkyl, $C_{1-6}$ haloalkyl, —C(O)$R_d$ and —$S(O)_mR_d$;

$R_{N2}$ is selected from H, $C_{1-6}$ alkyl, $C_{1-6}$ haloalkyl, —C(O)$R_d$, —$S(O)_mR_d$, —$C_{1-6}$ alkylene-$OR_5$, —$C_{1-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; alternatively selected from: H, Me, —$S(O)_2Me$, —$CH_2CH_2OCH_3$,

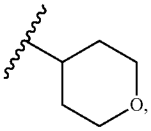
,
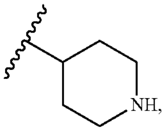
,
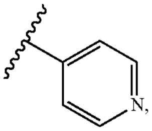
,
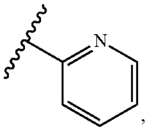
,
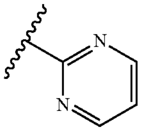
and
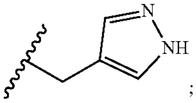
;

$R_d$ is selected from $C_{1-6}$ alkyl and $C_{1-6}$ haloalkyl;

m is 0, 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

$R_3$ is $C_{1-6}$ alkyl or $C_{1-6}$ haloalkyl;

$R_{N1}$ is H;

$R_{N2}$ is 3- to 7-membered heterocyclyl; alternatively

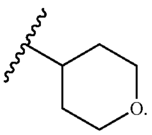 [SMILES: *C1CCOCC1]
.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-1) or (II-1):

(I-1)

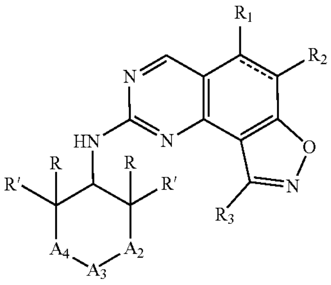

or (II-1)

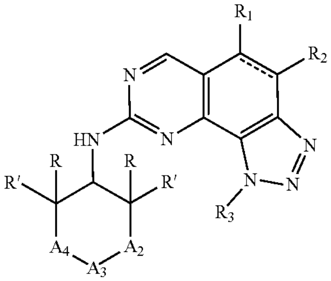

wherein:

$\overset{----}{=}$ indicates a single bond or a double bond;

$A_2$ is CRR' or NR";

$A_3$ is CRR' or $NR_4$;

$A_4$ is CRR' or NR";

or $A_3$, $A_4$ and substituents thereon are combined to form $C_{6-10}$ aryl or 5- to 10-membered heteroaryl;

R and R' are independently selected from H, D, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_4$ and R" are independently selected from H, $C_{1-6}$ alkyl, $C_{1-6}$ haloalkyl, $C_{2-6}$ alkenyl, $C_{2-6}$ alkynyl, —C(O)$R_d$, —S(O)$_m R_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

$\overline{\underline{\ \ }}$ indicates a single bond or a double bond;

$A_2$ is CRR' or NR";

$A_3$ is CRR' or $NR_4$;

$A_4$ is CRR' or NR";

or $A_3$, $A_4$ and substituents thereon are combined to form $C_{6-10}$ aryl or 5- to 10-membered heteroaryl;

R and R' are independently selected from H, D, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_1$ is selected from H, D, halogen, —CN, —$OR_a$, —$SR_a$ and —$NR_bR_c$;

$R_2$ is selected from H, D, halogen, —CN, —$OR_a$, —$SR_a$ and —$NR_bR_c$;

$R_3$ is selected from $C_{1-6}$ alkyl and $C_{1-6}$ haloalkyl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_4$ and R" are independently selected from H, $C_{1-6}$ alkyl, $C_{1-6}$ haloalkyl, $C_{2-6}$ alkenyl, $C_{2-6}$ alkynyl, —C(O)$R_d$, —S(O)$_m R_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, $C_{6-10}$ aryl and 6- to 10-membered heteroaryl;

m is 0, 1 or 2;

$R_5$, $R_6$ and $R_7$ are independently selected from H, $C_{1-6}$ alkyl and $C_{1-6}$ haloalkyl.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-4), (I-4-1), (I-4-2), (II-4), (II-4-1) or (II-4-2):

(I-4)

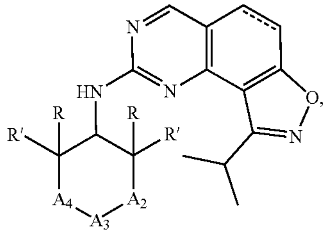

(I-4-1)

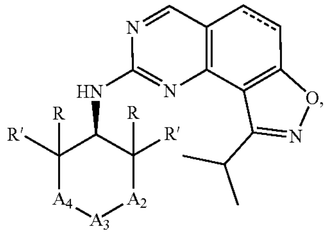

(I-4-2)

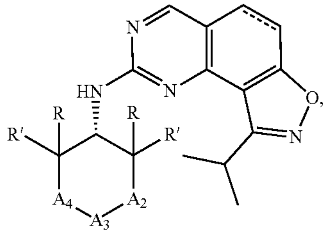

(II-4)

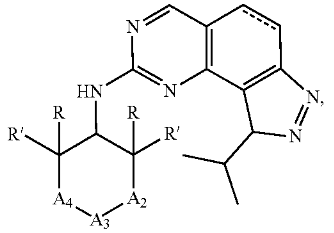

(II-4-1)

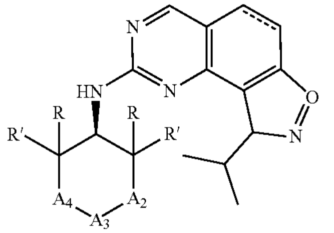

or

-continued (II-4-2)

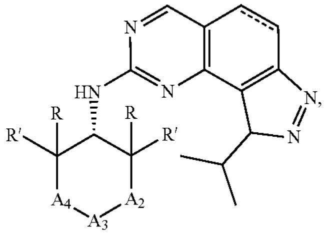

wherein:

$\overline{\overline{\ldots}}$ indicates a single bond or a double bond;

$A_2$ is CRR' or NR";

$A_3$ is CRR' or $NR_4$;

$A_4$ is CRR' or NR";

or $A_3$, $A_4$ and substituents thereon are combined to form $C_{6-10}$ aryl;

R and R' are independently selected from H, D, $C_{1-6}$ alkyl, $C_{1-6}$ haloalkyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_4$ and R" are independently selected from H, $C_{1-6}$ alkyl, $C_{1-6}$ haloalkyl, —C(O)$R_d$ and —S(O)$_m$$R_d$; $R_4$ and R" are alternatively selected from H, $C_{1-6}$ alkyl, $C_{1-6}$ haloalkyl and —S(O)$_m$$R_d$; alternatively selected from: H, methyl,

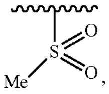, 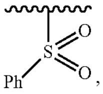, 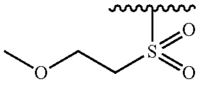 and 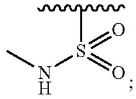;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, $C_{6-10}$ aryl and 6- to 10-membered heteroaryl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorgh, a prodrug, or an isotope variant thereof, or a mixture thereof, wherein:

$\overline{\overline{\ldots}}$ indicates a single bond or a double bond;

$A_2$ is CRR';

$A_3$ is $NR_4$;

$A_4$ is CRR';

R and R' are H or D;

$R_4$ is selected from H, —C(O)$R_d$ and —S(O)$_m$$R_d$; alternatively $R_4$ is H or —S(O)$_m$$R_d$;

$R_d$ is selected from $C_{1-6}$ alkyl and $C_{1-6}$ haloalkyl;

m is 1 or 2.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-5) or (II-5):

(I-5)

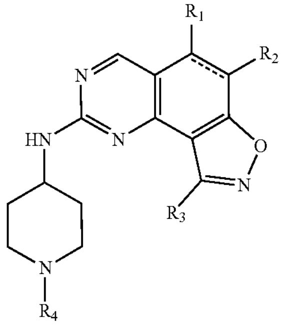

or (II-5)

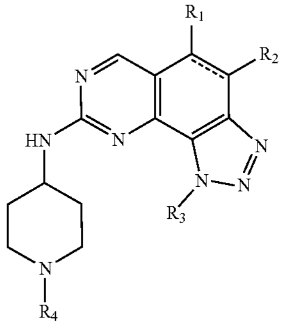

wherein:

$\overline{\overline{\ldots}}$ indicates a single bond or a double bond;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_4$ is selected from $C_{1-6}$ alkyl, $C_{1-6}$ haloalkyl, $C_{2-6}$ alkenyl, $C_{2-6}$ alkynyl, —C(O)$R_d$, —S(O)$_m$$R_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is selected from H, D, halogen, —CN, —$OR_a$, —$SR_a$ and —$NR_bR_c$;

$R_2$ is selected from H, D, halogen, —CN, —$OR_a$, —$SR_a$ and —$NR_bR_c$;

$R_3$ is selected from $C_{1-6}$ alkyl and $C_{1-6}$ haloalkyl;

$R_4$ is selected from $C_{1-6}$ alkyl, $C_{1-6}$ haloalkyl, $C_{2-6}$ alkenyl, $C_{2-6}$ alkynyl, —$C(O)R_d$, —$S(O)_mR_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, $C_{6-10}$ aryl and 6- to 10-membered heteroaryl;

m is 0, 1 or 2;

$R_5$, $R_6$ and $R_7$ are independently selected from H, $C_{1-6}$ alkyl and $C_{1-6}$ haloalkyl.

In another embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-5) or (II-5):

(I-5)

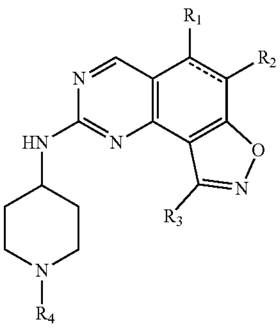

or

-continued (II-5)

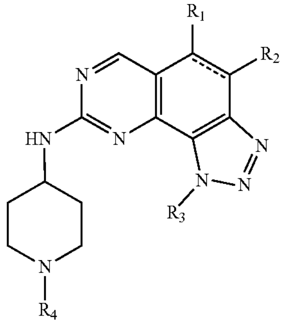

wherein:

⎓ indicates a single bond or a double bond;

$R_1$ is selected from H, D, halogen, —CN, —$OR_a$, —$SR_a$ and —$NR_bR_c$;

$R_2$ is selected from H, D, halogen, —$SR_a$, —$NR_bR_c$, $C_{1-6}$ alkyl, $C_{1-6}$ haloalkyl, —$C_{0-6}$ alkylene-$OR_a$, —$C_{0-6}$ alkylene-CN, $C_{3-7}$ cycloalkyl, 3- to 7-membered heterocyclyl, $C_{6-10}$ aryl and 5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_2$, $C_{1-6}$ alkyl and $C_{1-6}$ haloalkyl;

$R_4$ is H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl, —$C_{0-6}$ alkylene-5- to 10-membered heteroaryl, —$C(O)R_a$, or —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is selected from H, D, and halogen;

$R_2$ is selected from H, D, halogen, $C_{1-6}$ alkyl, $C_{1-6}$ haloalkyl, —$C_{0-6}$ alkylene-$OR_a$, —$C_{0-6}$ alkylene-CN, $C_{3-7}$ cycloalkyl, 3- to 7-membered heterocyclyl, $C_{6-10}$ aryl and 5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3 or 4 substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is H, $C_{1-6}$ alkyl, $C_{1-6}$ haloalkyl, —$C(O)R_a$, or —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, or halogen;

$R_2$ is selected from H, D, halogen, $C_{1-6}$ alkyl, $C_{1-6}$ haloalkyl, —$C_{0-6}$ alkylene-$OR_a$, and —$C_{0-6}$ alkylene-CN;

$R_a$ is H, $C_{1-6}$ alkyl, or $C_{1-6}$ haloalkyl;

$R_3$ is selected from $C_{1-6}$ alkyl and $C_{1-6}$ haloalkyl;

$R_4$ is H, $C_{1-6}$ alkyl, $C_{1-6}$ haloalkyl, or —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, or halogen;

$R_2$ is selected from H, D, halogen, $C_{1-6}$ alkyl, $C_{1-6}$ haloalkyl, and —$C_{1-6}$ alkylene-OH;

$R_3$ is $C_{1-6}$ alkyl;

$R_4$ is H, $C_{1-6}$ alkyl, or —$S(O)_mR_d$; alternatively H, Me, Me

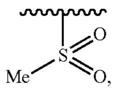,
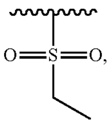,
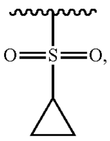,

-continued

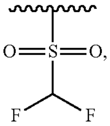,
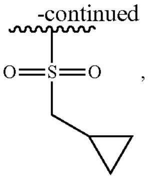,
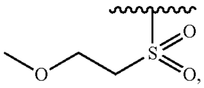,
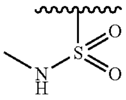
or
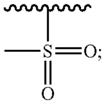;

$R_d$ is $C_{1-6}$ alkyl, $C_{1-6}$ haloalkyl, —$C_{0-6}$ alkylene-$OR_5$, —$NR_6R_2$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is selected from H, D, halogen, —CN, —$SR_a$ and —$NR_bR_c$;

$R_2$ is selected from H, D, halogen, —CN, —$SR_a$, —$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_2$, $C_{1-6}$ alkyl and $C_{1-6}$ haloalkyl;

$R_4$ is —$S(O)_mR_d$, or —$C(O)R_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is selected from H, D, and halogen;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3 or 4 substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_2$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, or halogen;

$R_2$ is selected from H, D, halogen, $C_{1-6}$ alkyl and $C_{1-6}$ haloalkyl;

$R_3$ is selected from $C_{1-6}$ alkyl and $C_{1-6}$ haloalkyl;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, or halogen;

$R_2$ is selected from H, D, halogen, $C_{1-6}$ alkyl, and $C_{1-6}$ haloalkyl;

$R_3$ is $C_{1-6}$ alkyl;

$R_4$ is —$S(O)_mR_d$; alternatively

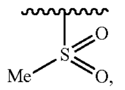
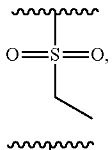
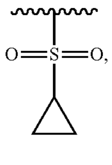
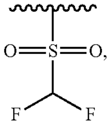
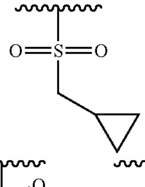
,
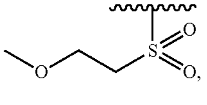
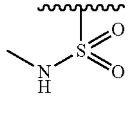
or -continued

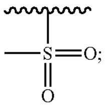

$R_d$ is $C_{1-6}$ alkyl, $C_{1-6}$ haloalkyl, —$C_{0-6}$ alkylene-$OR_5$, —$NR_6R_2$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, or halogen;

$R_2$ is selected from H, D, halogen, $C_{1-6}$ alkyl and $C_{1-6}$ haloalkyl;

$R_3$ is selected from —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is —$S(O)_mR_d$;

$R_d$ is $C_{1-6}$ alkyl, $C_{1-6}$ haloalkyl, —$C_{0-6}$ alkylene-$OR_5$, —$NR_6R_2$, or —$C_{0-6}$ alkylene-$C_{3-7}$ cycloalkyl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H, D, or halogen;

$R_2$ is selected from H, D, halogen, $C_{1-6}$ alkyl and $C_{1-6}$ haloalkyl;

$R_3$ is $C_{3-7}$ cycloalkyl, which may be optionally substituted by 1, 2, 3 or 4 substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is —$S(O)_mR_d$; alternatively

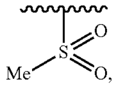
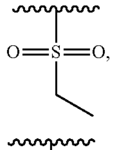
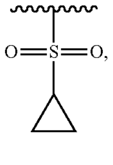
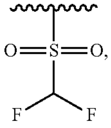
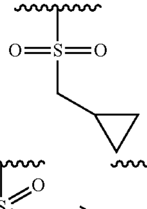
,
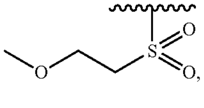
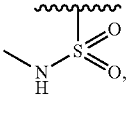
or -continued

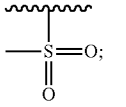

$R_d$ is $C_{1-6}$ alkyl, $C_{1-6}$ haloalkyl, —$C_{0-6}$ alkylene-$OR_5$, —$NR_6R_2$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_1$ is H;

$R_2$ is $C_{1-6}$ haloalkyl;

$R_3$ is cyclopentyl, which can be optionally substituted by 1, 2 or 3 —OH or $C_{1-6}$ alkyl groups, alternatively

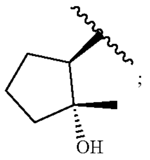 [SMILES: *[C@@H]1CCC[C@@]1(C)O]

$R_4$ is —$S(O)_mR_d$; alternatively

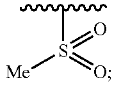

$R_d$ is $C_{1-6}$ alkyl, or $C_{1-6}$ haloalkyl;

m is 2.

In a specific embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-6) or (II-6):

(I-6)

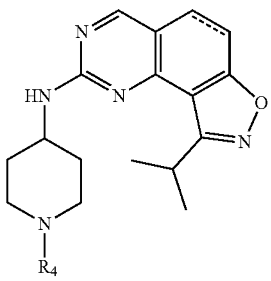

or

-continued (II-6)

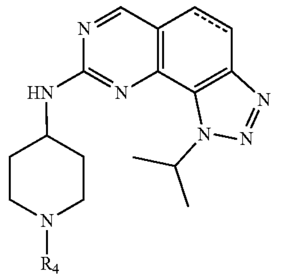

wherein:

⎓ indicates a single bond or a double bond;

$R_4$ is selected from $C_{1-6}$ alkyl, $C_{1-6}$ haloalkyl, —$C(O)R_d$ and —$S(O)_mR_d$; alternatively selected from $C_{1-6}$ alkyl, $C_{1-6}$ haloalkyl and —$S(O)_mR_d$; alternatively selected from: methyl,

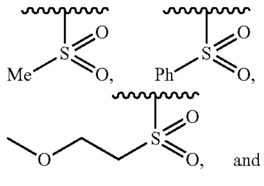

and

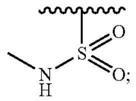

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, $C_{6-10}$ aryl and 6- to 10-membered heteroaryl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a double bond;

$R_4$ is selected from —$C(O)R_d$ and —$S(O)_mR_d$; alternatively —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, $C_{6-10}$ aryl and 6- to 10-membered heteroaryl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a double bond;

$R_4$ is selected from —$C(O)R_d$ and —$S(O)_mR_d$; alternatively —$S(O)_mR_d$;

$R_d$ is selected from $C_{1-6}$ alkyl and $C_{1-6}$ haloalkyl;

m is 1 or 2.

In a specific embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-6) or (II-6):

(I-6)

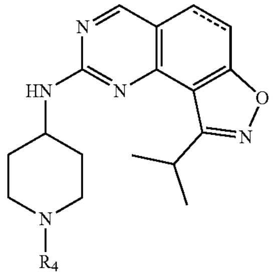

or (II-6)

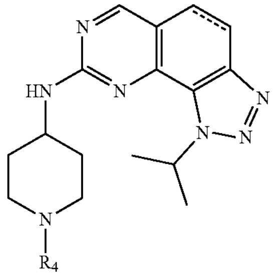

wherein:

⎓ indicates a single bond or a double bond;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

⎓ indicates a single bond or a double bond;

$R_4$ is —$S(O)_mR_d$; alternatively

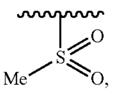 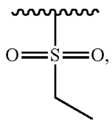 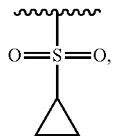

-continued

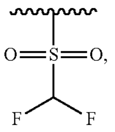 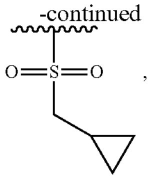 ,

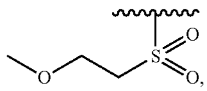 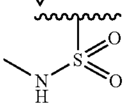 or

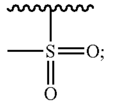

$R_d$ is $C_{1-6}$ alkyl, $C_{1-6}$ haloalkyl, —$C_{0-6}$ alkylene-$OR_5$, —$NR_6R_7$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl.

In a specific embodiment, the present disclosure provides a compound, or a pharmaceutically acceptable salt, an enantiomer, a diastereomer, a racemate, a solvate, a hydrate, a polymorph, a prodrug, or an isotope variant thereof, or a mixture thereof, which has a structure of general formula (I-7) or (II-7):

(I-7)

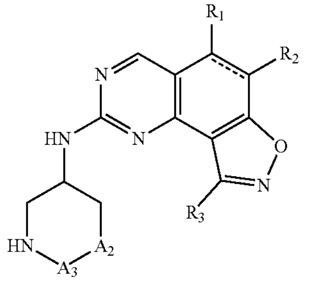

or (II-7)

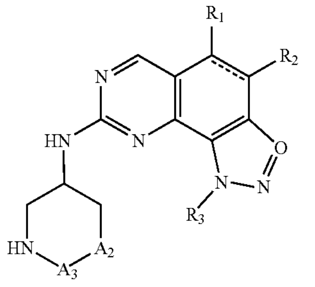

wherein

⎓ indicates a single bond or a double bond;

$R_1$ is H, D, halogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3 or 4 substituents selected from D, halogen, $-C_{0-6}$ alkylene-$OR_5$, $-CN$, $-NR_6R_7$, $C_{1-6}$ alkyl and $C_{1-6}$ haloalkyl;

$A_2$ is CRR' or NR';

$A_3$ is CRR';

R and R' are independently selected from H, D, halogen, $C_{1-6}$ alkyl, $C_{1-6}$ haloalkyl, $-C_{0-6}$ alkylene-$C_{3-7}$ cycloalkyl, $-C_{0-6}$ alkylene-3- to 7-membered heterocyclyl, $-C_{0-6}$ alkylene-$C_{6-10}$ aryl and $-C_{0-6}$ alkylene-5- to 10-membered heteroaryl; or R, R' and the carbon atom attached thereto are combined to form C=O.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

$\overline{\overline{\;\;}}$ indicates a single bond or a double bond;

$R_1$ is H, D, or halogen;

$R_2$ is selected from H, D, and halogen;

$R_3$ is selected from $C_{1-6}$ alkyl and $C_{1-6}$ haloalkyl;

$A_2$ is CRR' or NR';

$A_3$ is CRR';

R and R' are independently selected from H, D, halogen, $C_{1-6}$ alkyl, $C_{1-6}$ haloalkyl, $-C_{0-6}$ alkylene-$C_{3-7}$ cycloalkyl, $-C_{0-6}$ alkylene-3- to 7-membered heterocyclyl, $-C_{0-6}$ alkylene-$C_{6-10}$ aryl and $-C_{0-6}$ alkylene-5- to 10-membered heteroaryl; or R, R' and the carbon atom attached thereto are combined to form C=O.

In a more specific embodiment, the present disclosure provides a compound as mentioned above, or a pharmaceutically acceptable salt, an enantiomer, a diastereomer, a racemate, a solvate, a hydrate, a polymorph, a prodrug, or an isotope variant thereof, or a mixture thereof, wherein:

$\overline{\overline{\;\;}}$ indicates a single bond or a double bond;

$R_1$ is H;

$R_2$ is H;

$R_3$ is $C_{1-6}$ alkyl;

$A_2$ is CRR', alternatively $-CH_2-$;

$A_3$ is CRR';

R and R' are independently H; or R, R' and the carbon atom attached thereto are combined to form C=O.

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula $R \cdot x\ H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates ($R \cdot 0.5\ H_2O$)) and polyhydrates (x is a number greater than 1, for example, dihydrates ($R \cdot 2\ H_2O$) and hexahydrates ($R \cdot 6\ H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes (isotopic variants), which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$ $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}H$ and $^{14}C$), can be used for the measurement of the distribution of drug and/or substrate in tissue. Tritium, which is $^{3}H$ and carbon-14, which is $^{14}C$ isotope, are yet alternative, because they are easy to prepare and detect. Furthermore, replaced by heavier isotopes, such as deuterium, which is $^{2}H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted into an active form that has medical effects in vivo by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference. The present disclosure also provides a pharmaceutical formulation comprising a therapeutically effective amount of a compound of formula (I), or therapeutically acceptable salts thereof, and pharmaceutically acceptable carriers, diluents or excipients thereof. All of these forms belong to the present disclosure.

The alternative compounds disclosed herein include but are not limited to the following compounds, or a pharmaceutically acceptable salt, an enantiomer, a diastereomer, a racemate, a solvate, a hydrate, a polymorph, a prodrug, or an isotope variant thereof, or a mixture thereof:

I.1

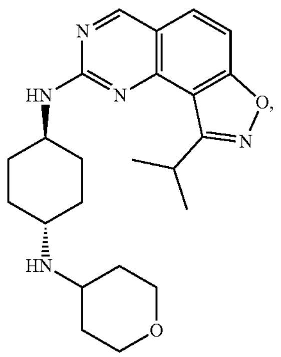

I.2

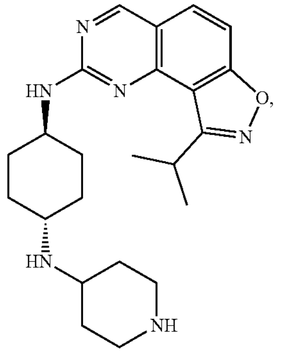

-continued

I.3

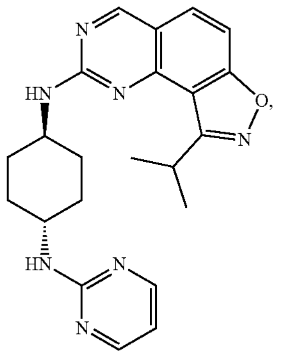

I.4

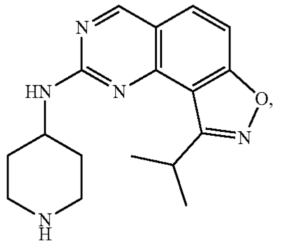

I.5

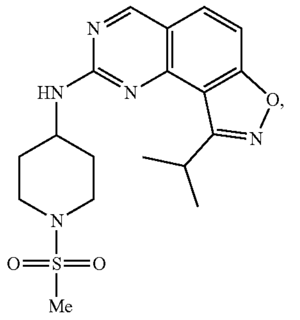

I.6

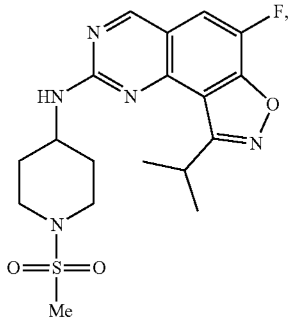

I.7

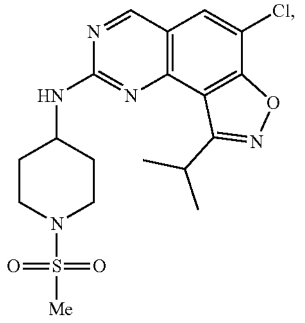

-continued
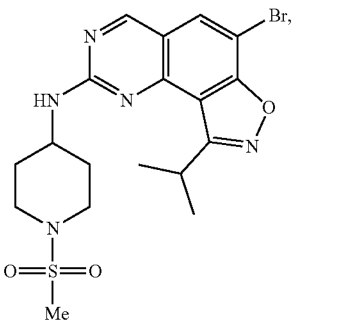
I.8
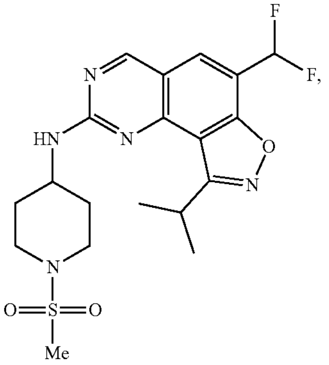
I.9
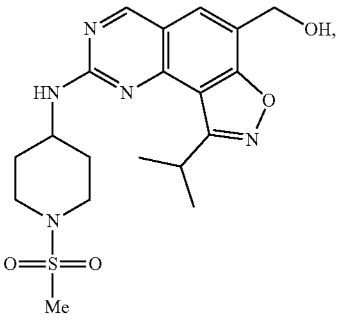
I.10
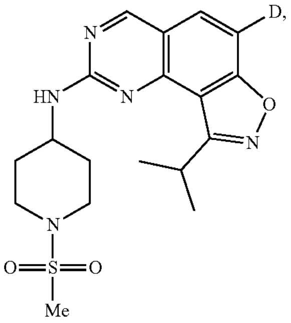
I.11
-continued
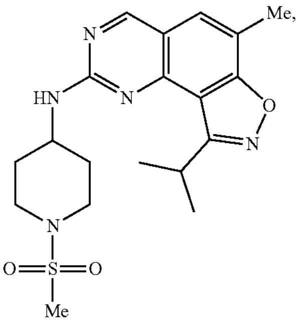
I.12
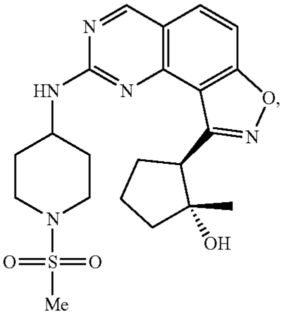
I.13
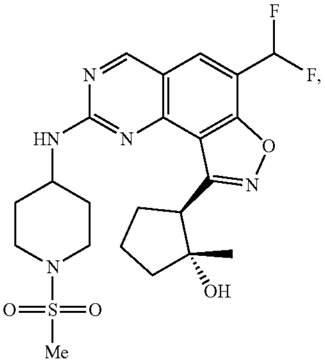
I.14
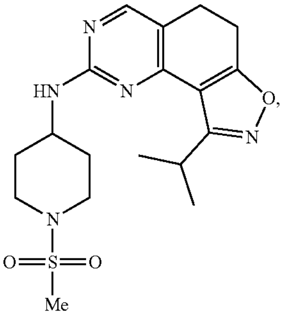
I.15

-continued
I.16
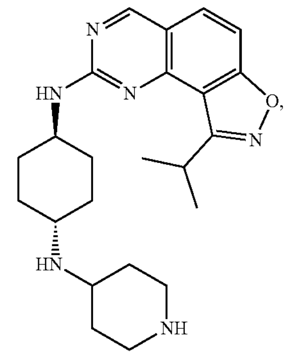
II.1
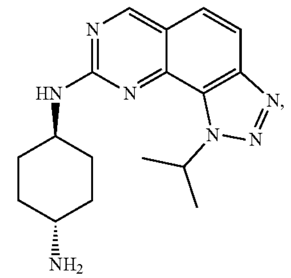
II.2
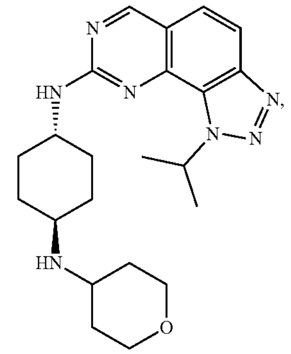
II.3
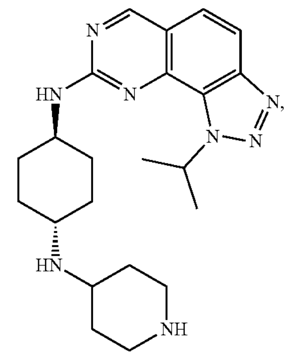
-continued
II.4
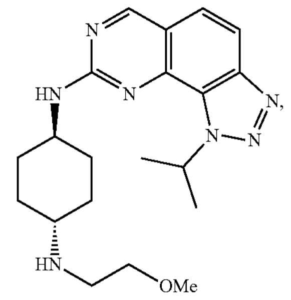
II.5
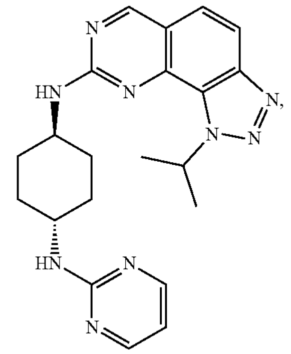
II.6
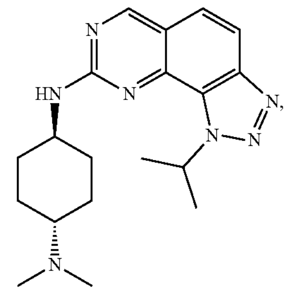
II.7
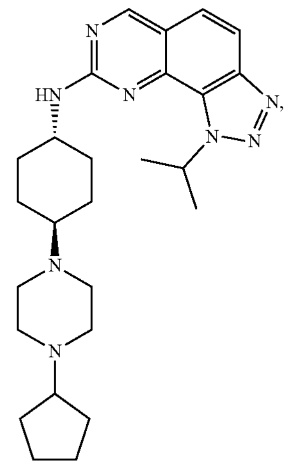

-continued
II.8
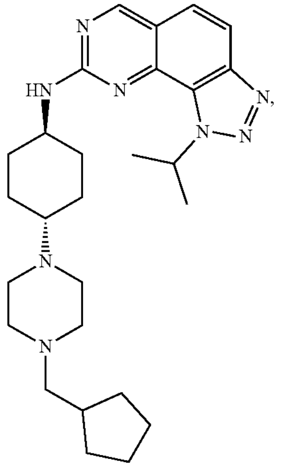
II.9
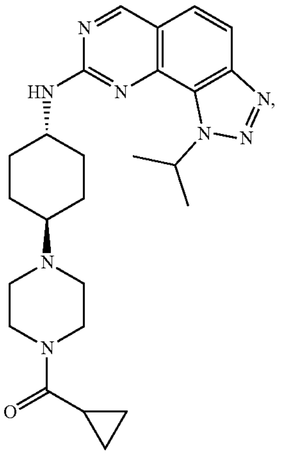
II.10
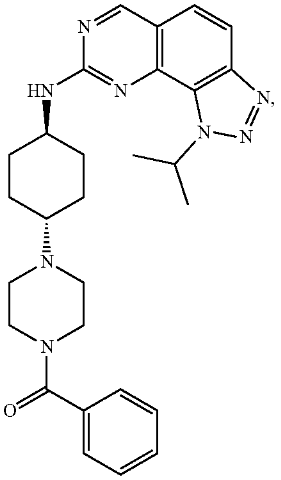
-continued
II.11
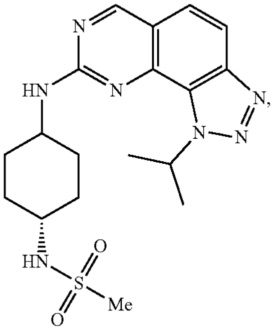
II.12
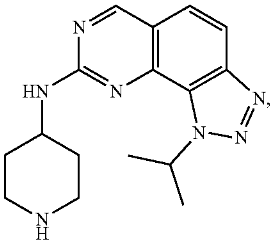
II.13
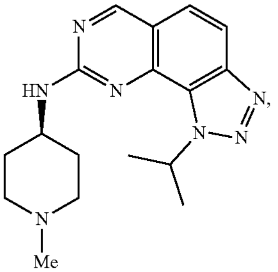
II.14
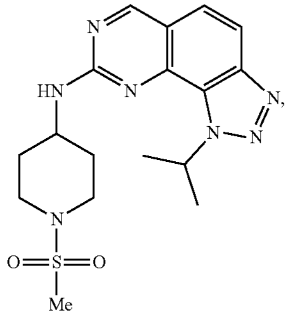
II.15
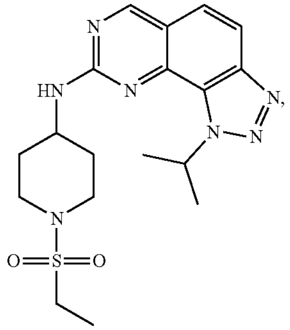

-continued
II.16
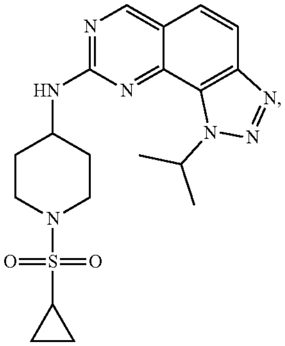
II.17
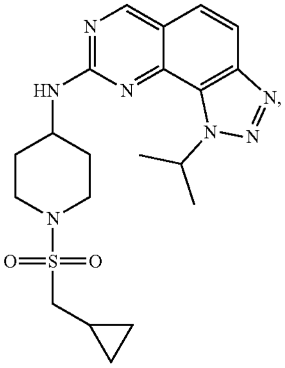
II.18
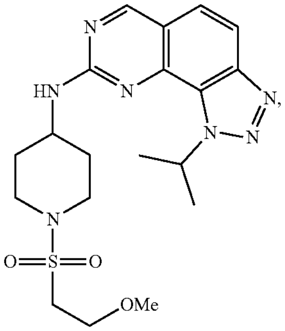
II.19
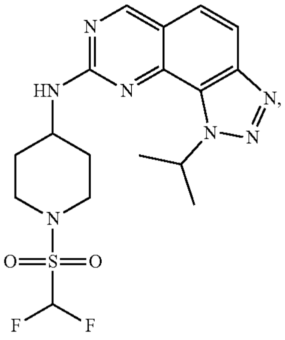
-continued
II.20
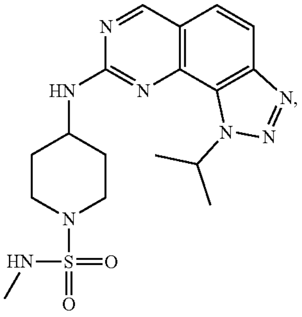
II.21
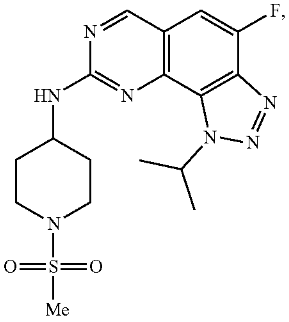
II.22
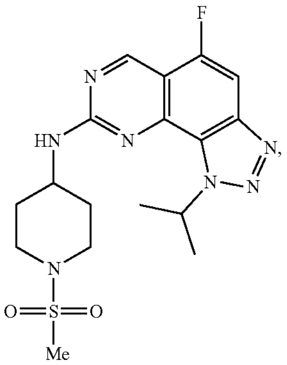
II.23
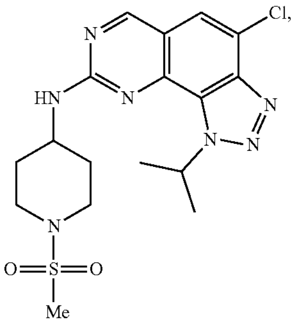

-continued
II.24
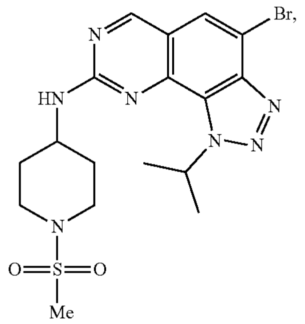
II.25
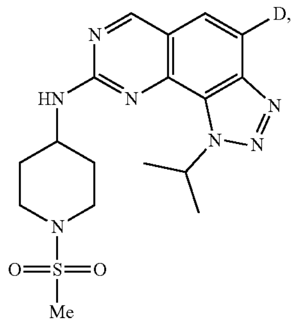
II.26
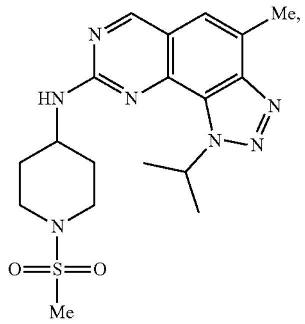
II.27
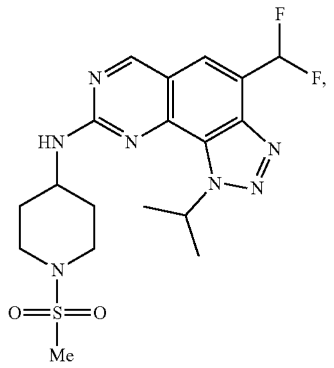
-continued
II.28
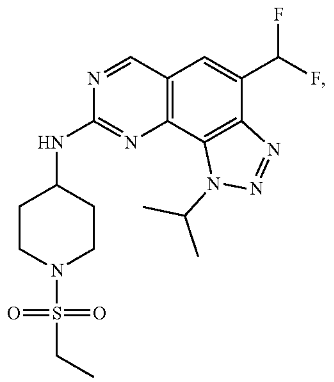
II.29
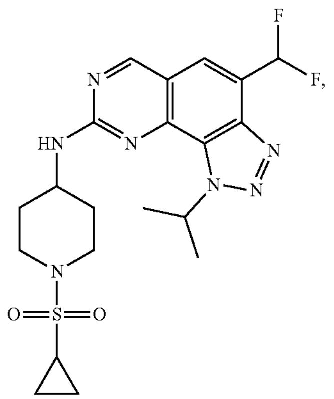
II.30
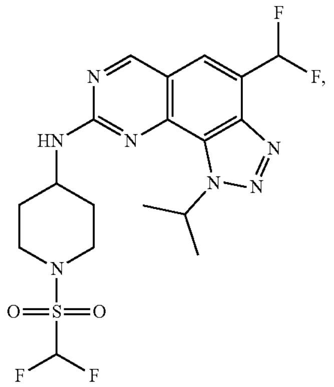
II.31
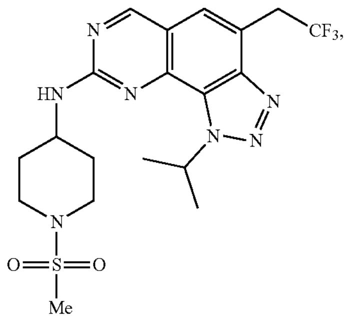

-continued

II.32

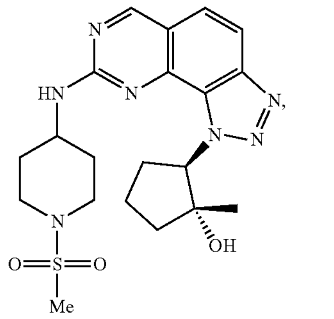

II.33

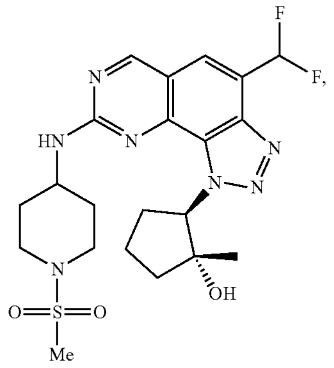

II.34

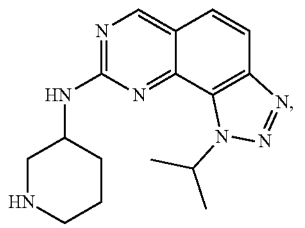

II.35

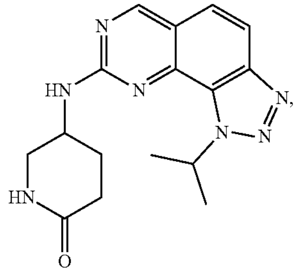

II.36

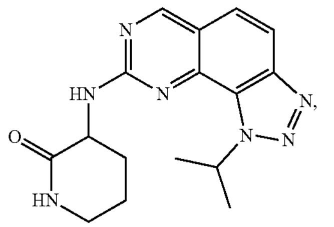

-continued

II.37

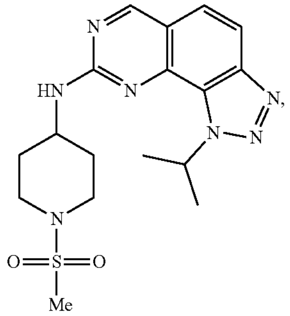

II.38

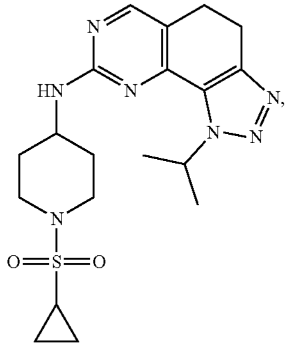

II.39

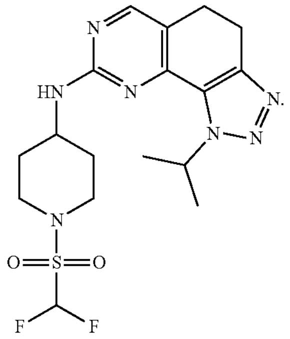

Pharmaceutical Compositions, Kits and Administration

In another aspect, the present disclosure provides a pharmaceutical composition comprising a compound of the present disclosure (also referred to as the "active ingredient") and pharmaceutically acceptable excipients. In some embodiments, the pharmaceutical composition comprises an effective amount of the compound of the present disclosure. In some embodiments, the pharmaceutical composition comprises a therapeutically effective amount of the compound of the present disclosure. In some embodiments, the pharmaceutical composition comprises a prophylactically effective amount of the compound of the present disclosure.

Pharmaceutically acceptable excipients for use in the present disclosure refer to the non-toxic carriers, adjuvants or vehicles, which do not destroy the pharmacological activity of the compounds formulated together. Pharmaceutically acceptable carriers, adjuvants, or vehicles that can be used in the compositions of the present disclosure include (but are not limited to) ion exchangers, alumina, aluminum stearate, lecithin, serum proteins (such as human serum proteins), buffer substances (such as phosphate), glycine, sorbic acid, potassium sorbate, mixture of partial glycerides of saturated plant fatty acids, water, salts or electrolytes (such as protamine sulfate), disodium hydrogen phosphate, potassium hydrogen phosphate, sodium chloride, zinc salts, silica gel, magnesium trisilicate, polyvinyl pyrrolidone, cellulose-based substance, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). The kits provided may include a compound of the present disclosure, other therapeutic agent(s), and a first and a second containers (e.g., vials, ampoules, bottles, syringes, and/or dispersible packages or other suitable containers) containing the compound of the present disclosure and other therapeutic agent(s). In some embodiments, the provided kits can also optionally include a third container containing a pharmaceutically acceptable excipient for diluting or suspending the compound of the present disclosure and/or other therapeutic agent(s). In some embodiments, the compound of the present disclosure provided in the first container and other therapeutic agent(s) provided in the second container are combined to form a unit dosage form.

The pharmaceutical composition provided by the present disclosure can be administered by a variety of routes including, but not limited to, oral administration, parenteral administration, inhalation administration, topical administration, rectal administration, nasal administration, buccal administration, vaginal administration, administration by implant or other means of administration. For example, parenteral administration as used herein includes subcutaneous administration, intradermal administration, intravenous administration, intramuscular administration, intra-articular administration, intra-arterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the route of administration selected, the actual compound administered, the age, weight and response of the individual patient, the severity of the patient's symptoms, etc.

EXAMPLES

The following examples are provided to provide those skilled in the art with a complete disclosure and description of how to implement, prepare and evaluate the methods and compounds claimed herein, and are intended to be illustrative only without limiting the scope of the invention.

The preparation protocol of the compound disclosed herein is shown, for example, in Schemes 1 and 2.

Scheme 1

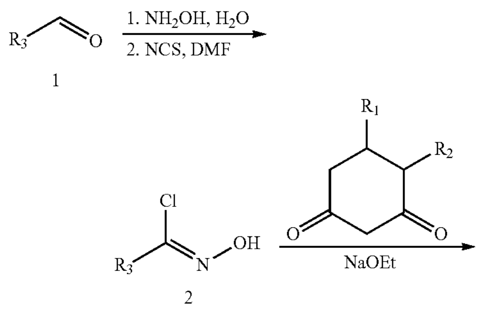

1

2

-continued

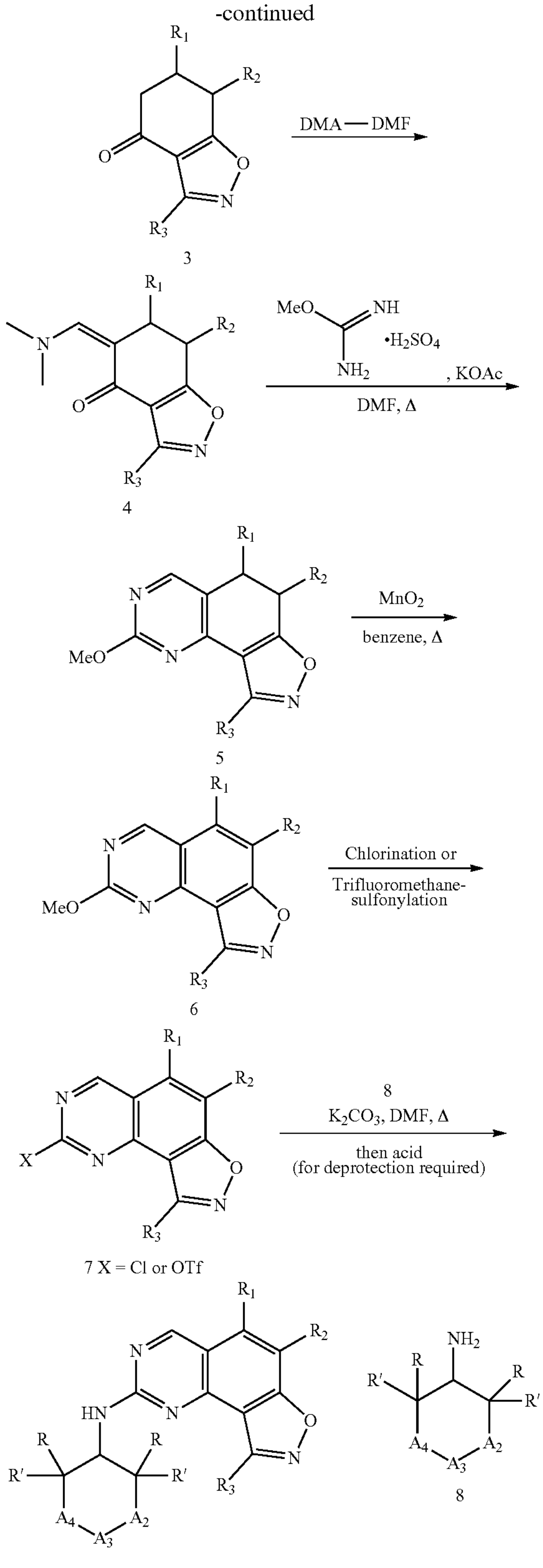

3

4

5

6

7 X = Cl or OTf

I-1

8

The compound of formula I-1 where ⎓ is a double bond could be prepared according to the above general scheme. Firstly, the aldoxime obtained from the reaction of aldehyde (1) with hydroxylamine is reacted with N-chlorosuccinimide (NCS) to afford intermediate (2). (2) is reacted with 1,3-cyclohexanedione to close the isoxazole ring to give 6,7-dihydrobenzo[d]isoxazol-4-(5H)-one (3). Then, (3) is reacted with N,N-dimethylformamide dimethylacetal to afford intermediate (4). Intermediate (4) is reacted with O-methylisourea sulfate to close the pyrimidine ring to give 2-methoxy-5,6-dihydroisoxazolo[5,4-H]quinazoline (5). 2-methoxyisoxazolo[5,4-h]quinazoline (6) is obtained by oxidation-aromatization of (5) under the action of manganese dioxide. (5). Afterwards, (6) is subjected to chlorination or trifluoromethanesulfonylation to obtain a chloride or trifluoromethanesulfonate (7). The compound (7) is coupled with amine (8), or further deprotected (when the molecule contains Boc or other protective groups) to obtain the compound of formula (I-1).

When $R_2$ is H (such as $R_2$ of (6) or $R_2$ of (I-1)), it can be transformed into representative groups such as F, Cl, Br, D, $CHF_2$, $CH_2CF_3$ through corresponding functional groups.

Scheme 1'

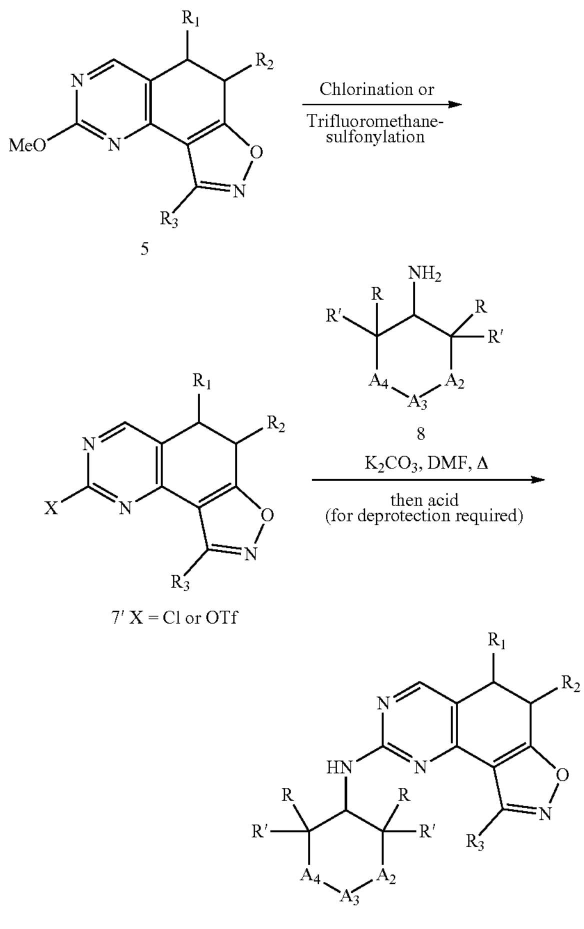

5

8

7' X = Cl or OTf

I-1

The compound of formula I-1 where ⎓ is a single bond could be prepared according to the above general scheme, wherein (5) prepared according to the method of Scheme 1 is directly subjected to chlorination or trifluoromethanesulfonylation (without oxidation-aromatization) to obtain a chloride or trifluoromethanesulfonate (7'). The compound (7') is coupled with amine (8), or further deprotected (when the molecule contains Boc or other protective groups) to obtain the compound of formula (I-1).

Scheme 2

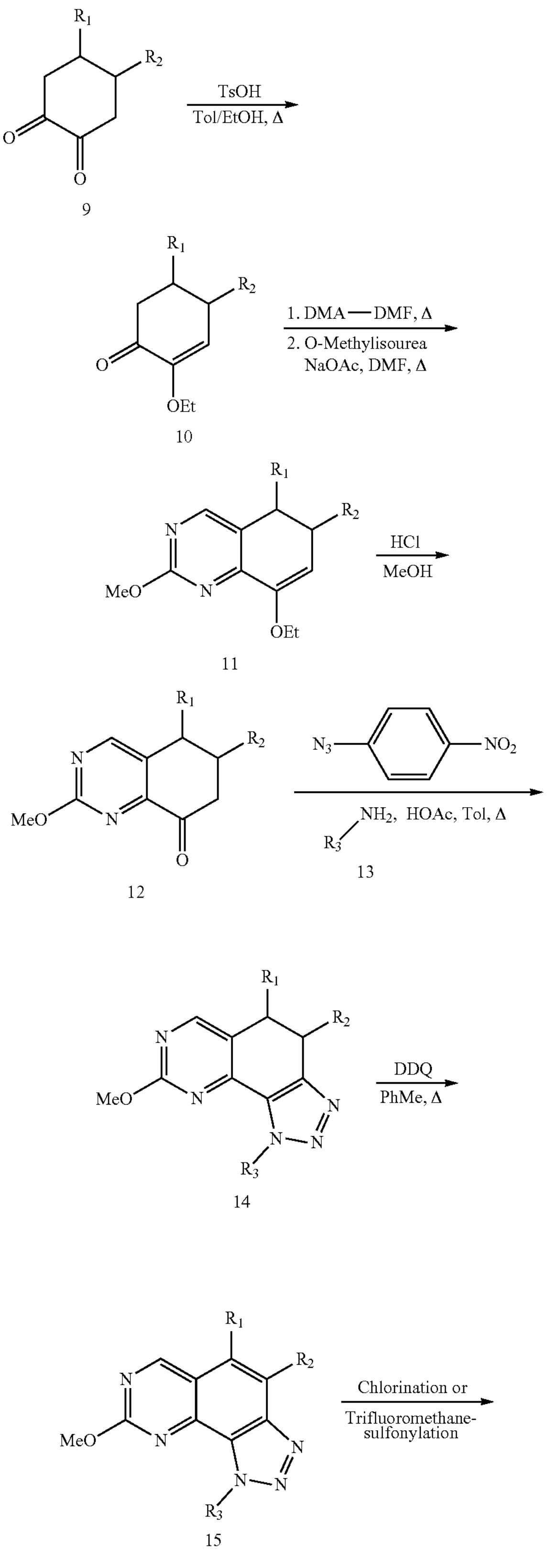

9

10

11

12

13

14

15

-continued

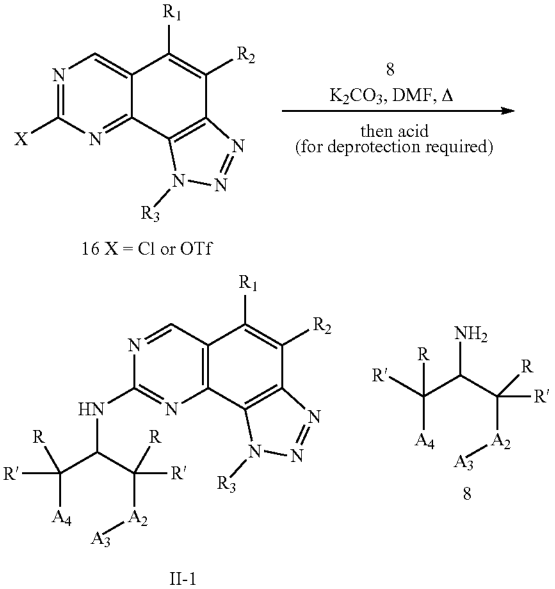

16 X = Cl or OTf

8

II-1

The compound of formula IT-1 where ⎓ is a double bond could be prepared according to the above general scheme. Firstly, 4- and/or 5-substituted 1,2-cyclohexanedione (9) is refluxed in toluene/ethanol under the catalysis of p-toluenesulfonic acid to obtain ketene intermediate (10). Then, (10) is reacted with N,N-dimethylformamide dimethyl acetal, and the obtained enamine intermediate is further reacted with O-methylisourea sulfate to obtain 8-ethoxy-2-methoxy-5,6-dihydroquinazoline (11). (11) is reacted with hydrogen chloride to obtain 2-methoxy-6,7-dihydroquinazoline-8(5H)-ketone (12). (12) is reacted with 1-azido-4-nitrobenzene and amine (13) to obtain 1-substituted 8-methoxy-4,5-dihydro-1H-[1,2,3]triazolo[4,5-H]quinazoline (14). Then, 1-substituted-8-methoxy-1H-[1,2,3]triazolo[4,5-h]quinazoline (15) is obtained by oxidation-aromatization of (14) under the action of 2,3-dichloro-5,6-dicyano-1,4-benzoquinone (DDQ). Afterwards, (15) is subjected to chlorination or trifluoromethanesulfonylation to obtain a chloride or trifluoromethanesulfonate (16). The compound (16) is coupled with amine (8), or further deprotected (when the molecule contains Boc or other protective groups) to obtain the compound of formula (II-1).

When $R_2$ is H (such as $R_2$ of (15) or $R_2$ of (II-1)), it can be transformed into representative groups such as F, Cl, Br, D, $CHF_2$, $CH_2CF_3$ through corresponding functional groups.

Scheme 2'

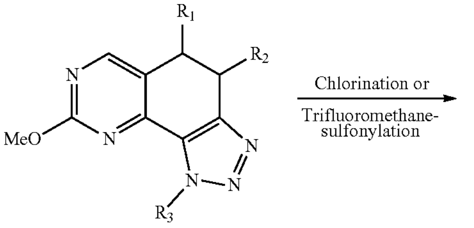

14

-continued

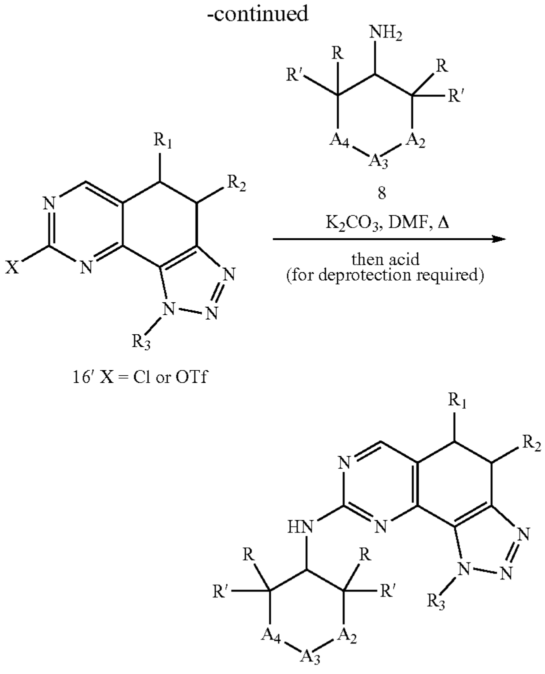

16' X = Cl or OTf

II-1

The compound of formula II-1 where ⎓ is a single bond could be prepared according to the above general scheme, wherein (14) prepared according to the method of Scheme 2 is directly subjected to chlorination or trifluoromethanesulfonylation (without oxidation-aromatization) to obtain a chloride or trifluoromethanesulfonate (16'). The compound (16') is coupled with amine (8), or further deprotected (when the molecule contains Boc or other protective groups) to obtain the compound of formula (II-1).

Example I.1

(1R,4R)—$N^1$-(9-isopropylisoxazolo[5,4-h]quinazolin-2-yl)-$N^4$-(tetrahydro-2H-pyran-4-yl)cyclohexane-1, 4-diamine (I.1)

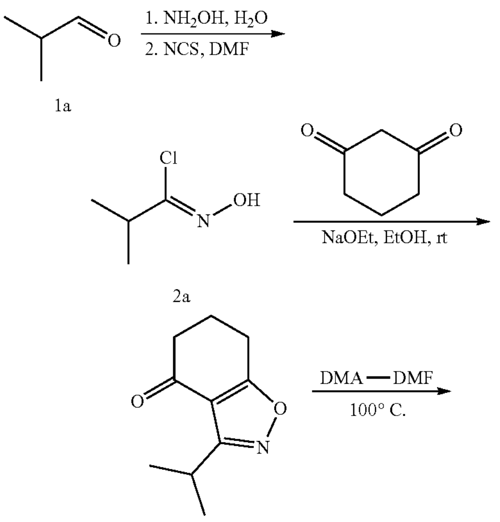

1a

2a

3a

-continued

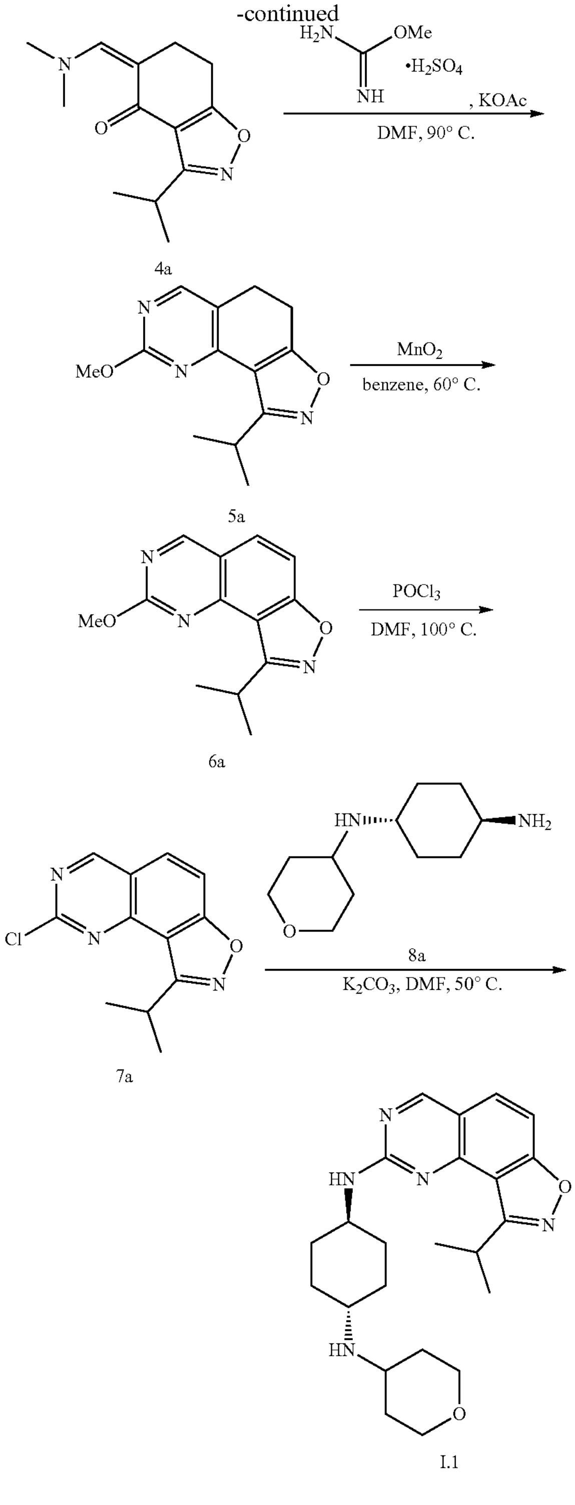

4a

5a

6a

7a

I.1

1): (Z)—N-hydroxyisobutyrimidoyl chloride (2a)

To a solution of isobutyraldehyde 1a (20.0 g, 0.278 mol) in water (300 mL) was added dropwise an aqueous hydroxylamine solution (25.4 mL, 50%) in an ice-water bath. After the addition was completed, the mixture was allowed to warm to room temperature and reacted for 12 hours. The reaction solution was extracted with dichloromethane (200 mL×3), and the organic layers were combined, dried (anhydrous sodium sulfate), filtered by suction, and concentrated. The obtained crude product (20.4 g) was dissolved in N,N-dimethylformamide (200 mL), and N-chlorosuccinimide (34.4 g, 0.258 mmol) was added in four portions in an ice-water bath. The mixture was warmed to room temperature, and the reaction was continued for 24 hours. Diethyl ether (600 mL) was added to dilute the reaction solution, and then the reaction solution was washed with water (80 mL×3), saturated brine (80 mL×1), separately. The resulting solution was dried (anhydrous sodium sulfate), filtered by suction, and concentrated to give the crude title compound 2a (26.0 g) as a pale-yellow oil. LC-MS (ESI), $C_4H_9ClNO$ $[M+H]^+$: m/z=122.0, 124.1. The crude product was directly used in the next reaction without further purification.

2): 3-isopropyl-6,7-dihydrobenzo[d]isoxazol-4-(5H)-one (3a)

To a solution of the crude 2a (26.0 g) from the above step and 1,3-cyclohexanedione (36.0 g, 0.322 mol) in anhydrous ethanol (300 mL) was added dropwise sodium ethoxide (109.6 g, 20% in ethanol) in an ice bath. After the addition was completed, the mixture was warmed to room temperature, and the reaction was continued until TLC monitoring showed that the raw material was completely reacted. Hydrogen chloride (1 N in water) was slowly added dropwise to adjust the pH of the reaction solution to about 8. The solution was concentrated under reduced pressure, and the resulting crude product was purified by flash silica gel column chromatography (petroleum ether/ethyl acetate=20:1 to 10:1) to give the title compound 3a (15.9 g, 89.0 mmol, 32% yield for three steps) as a pale-yellow solid. $^1H$ NMR (600 MHz, Chloroform-d, ppm) δ 3.35 (hept, J=6.9 Hz, 1H), 2.96 (t, J=6.3 Hz, 2H), 2.51 (dd, J=7.2, 5.7 Hz, 2H), 2.20 (p, J=6.4 Hz, 2H), 1.33 (d, J=6.9 Hz, 6H).

3): (Z)-5-((dimethylamino)methylene)-3-isopropyl-6,7-dihydrobenzo[d]isoxazol-4-(5H)-one (4a)

A solution of 3a (14.0 g, 78.2 mmol) and N,N-dimethylformamide dimethylacetal (51.9 mL, 0.391 mol) in N,N-dimethylformamide (104 mL) was stirred to react at 100° C. for 12 hours. After cooling to room temperature, the reaction solution was concentrated under reduced pressure to give the title compound 4a (17.3 g, 73.9 mmol) as a brown oil. This crude product was directly used in the next reaction without further purification. LC-MS (ESI), $C_{13}H_{19}N_2O_2$ $[M+H]^+$: m/z=235.2.

4): 9-isopropyl-2-methoxy-5,6-dihydroisoxazolo[5,4-H]quinazoline (5a)

The crude product from the previous step was dissolved in N,N-dimethylformamide (200 mL), and O-methylisourea sulfate (38.5 g, 156.4 mmol) and anhydrous potassium acetate (15.3 g, 156.4 mmol) were added. The mixture was then heated to 90° C. and stirred for 12 hours. After cooling to room temperature, the reaction solution was diluted with water (200 mL), and extracted with ethyl acetate (400 mL×3). The organic phases were combined, washed successively with water (80 mL×3) and saturated brine (80 mL×1), dried over anhydrous sodium sulfate and filtered. The filtrate was concentrated and purified by flash silica gel column chromatography (petroleum ether/ethyl acetate=3:1) to give the title compound 5a (8.2 g, 33.6 mmol, 43% yield in two steps) as a pale-yellow solid. $^1H$ NMR (400 MHz, Chloroform-d, ppm) δ 8.26 (s, 1H), 4.01 (s, 3H), 3.65 (p, J=6.7 Hz, 1H), 3.06 (d, J=1.2 Hz, 4H), 1.44 (d, J=6.9 Hz, 6H).

5): 9-isopropyl-2-methoxyisoxazolo[5,4-H]quinazoline (6a)

Manganese dioxide (26.6 g, 306 mmol) was added to a solution of 5a (7.5 g, 30.6 mmol) in benzene (400 mL), and the mixture was heated to 60° C. and stirred to react for 24 hours. The reaction solution was filtered by suction through a Celite pad, and the filter cake was washed with ethyl acetate (300 mL). The filtrate was concentrated under reduced pressure. The obtained residue was purified by flash silica gel column chromatography (petroleum ether/ethyl acetate=4:1) to give the title compound 6a (5.3 g, 21.7 mmol, 71%) as a pale-yellow solid. $^1$H NMR (400 MHz, Chloroform-d, ppm) δ 9.25 (s, 1H), 7.93 (d, J=8.9 Hz, 1H), 7.64 (d, J=8.9 Hz, 1H), 4.19 (s, 3H), 3.96 (dq, J=14.6, 7.2 Hz, 1H), 1.62 (d, J=6.9 Hz, 6H).

6): 2-chloro-9-isopropylisoxazolo[5,4-H]quinazoline (7a)

To a solution of 6a (5.0 g, 20.6 mmol) in DMF (120 mL) was slowly added dropwise phosphorus oxychloride (II.5 mL, 123.6 mmol) in an ice-water bath. After the addition was completed, the reaction was heated to 100° C. and reacted for 1 hour. The reaction was put into ice bath again, and diluted with ethyl acetate (600 mL). Aqueous sodium hydroxide solution (1 N) was slowly added dropwise with vigorous stirring to adjust the pH to about 8. The organic phase was separated, washed successively with water (80 mL×3) and saturated brine (80 mL×1), dried (anhydrous sodium sulfate), and filtered by suction. The filtrate was concentrated. The resulting residue was purified by flash silica gel column chromatography (petroleum ether/ethyl acetate=8:1) to give the title compound 7a (2.7 g, 10.9 mmol, 53%) as a pale-yellow solid. $^1$H NMR (400 MHz, Chloroform-d, ppm) δ 9.33 (s, 1H), 8.03 (d, J=9.9 Hz, 1H), 7.86 (d, J=9.9 Hz, 1H), 4.00 (p, J=7.7, 7.3 Hz, 1H), 1.61 (d, J=7.8 Hz, 6H).

7): (1R,4R)—N$^1$-(9-isopropylisoxazolo[5,4-h]quinazolin-2-yl)-N$^4$-(tetrahydro-2H-pyran-4-yl)cyclohexane-1,4-diamine (I.1)

To a suspension of 7a (60.0 mg, 0.243 mmol) and hydrochloride of (1R,4R)—N$^1$-(tetrahydro-2H-pyran-4-yl) cyclohexane-1,4-diamine 8a (118.1 mg, 0.486 mmol) in N,N-dimethylformamide (2 mL) was added potassium carbonate (134.1 mg, 0.972 mmol). The reaction was heated to 50° C., and reacted at this temperature for 3 hours under stirring. The reaction was put into ice-water bath, and diluted with ethyl acetate (15 mL) and water (4 mL). Aqueous hydrochloric acid solution (0.1 N) was slowly added dropwise with vigorous stirring to adjust the pH to about 8. The aqueous phase was separated. The organic phase was washed successively with water (3 mL×2) and saturated brine (5 mL×1), dried (anhydrous sodium sulfate), filtered by suction, and concentrated. The resulting residue was purified by flash silica gel column chromatography (dichloromethane/methanol=100:1) to give the title compound 1.1 (82.7 mg, 0.202 mmol, 83%) as a pale-yellow solid. $^1$H NMR (400 MHz, chloroform-d, ppm) δ 8.92 (s, 1H), 7.70 (d, J=8.8 Hz, 1H), 7.36 (d, J=8.8 Hz, 1H), 5.32 (d, J=7.7 Hz, 1H), 4.00 (ddd, J=12.1, 4.4, 2.2 Hz, 2H), 3.90 (p, J=6.9 Hz, 1H), 3.42 (td, J=11.8, 2.0 Hz, 2H), 2.86 (td, J=10.6, 5.2 Hz, 1H), 2.74 (s, 1H), 2.29 (s, 2H), 2.03 (s, 2H), 1.92-1.85 (m, 2H), 1.59 (d, J=7.0 Hz, 6H), 1.46-1.37 (m, 2H), 1.37-1.30 (m, 4H).

Example I.2

Hydrochloride of (1R,4R)—N$^1$-(9-isopropylisoxazolo[5,4-h]quinazolin-2-yl)-N$^4$-(piperidin-4-yl)cyclohexane-1,4-diamine (I.2)

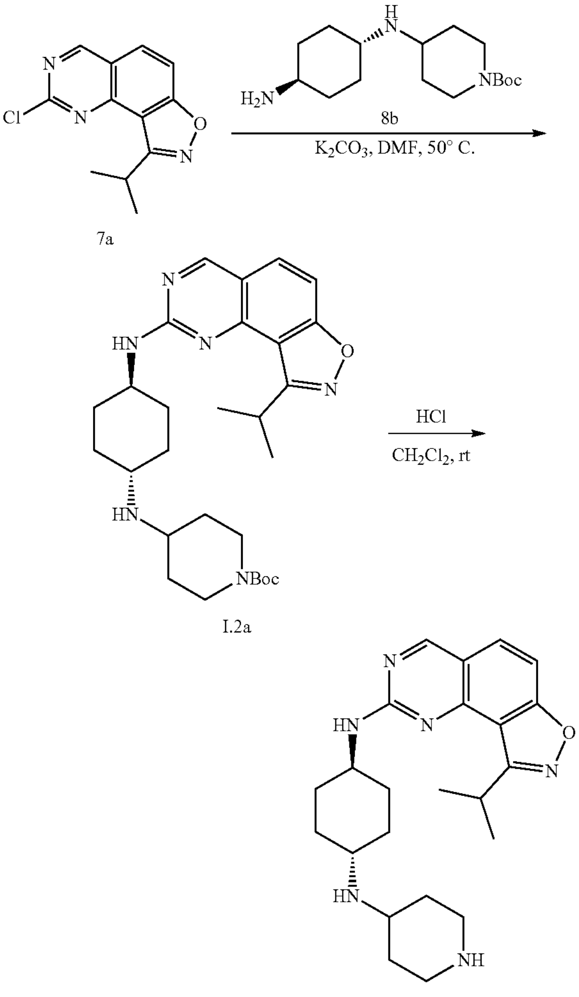

7a 8b I.2a I.2

1): Tert-butyl 4-(((1R,4R)-4-((9-isopropylisoxazolo[5,4-h]quinazolin-2-yl)amino)cyclohexyl)amino)piperidine-1-carboxylate (I.2a)

To a solution of 7a (60.0 mg, 0.243 mmol) and tert-butyl 4-(((1R,4R)-4-aminocyclohexyl)amino)piperidine-1-carboxylate 8b (144.4 mg, 0.486 mmol) in N,N-dimethylformamide (2 mL) was added potassium carbonate (67.0 mg, 0.486 mmol). The reaction was heated to 50° C., and reacted at this temperature for 3 hours under stirring. The reaction was put into ice-water bath, and diluted with ethyl acetate (15 mL) and water (4 mL). Aqueous hydrochloric acid solution (0.1 M) was slowly added dropwise with vigorous stirring to adjust the pH to about 8. The aqueous phase was separated. The organic phase was washed successively with water (3 mL×2) and saturated brine (5 mL×1), dried (anhydrous sodium sulfate), filtered by suction, and concentrated. The resulting residue was purified by flash silica gel column chromatography (dichloromethane/methanol=100:1) to give the title compound I.2a (106.2 mg, 0.209 mmol, 86%) as a pale-yellow solid. LC-MS (ESI), $C_{28}H_{41}N_6O_3$ $[M+H]^+$: m/z=509.3.

2): (1R,4R)—N[1]-(9-isopropylisoxazolo[5,4-h]quinazolin-2-yl)-N[4]-(piperidin-4-yl)cyclohexane-1,4-diamine (I.2)

I.2a (60 mg, 0.118 mmol) was dissolved in dichloromethane (2 mL), and hydrogen chloride (4 N solution in 1,4-dioxane, 0.3 mL) was added. The reaction solution was stirred at room temperature for 2 hours, and then filtered by suction. The obtained filter residue was dried in vacuum by oil pump to constant weight to give the hydrochloride of the title compound 1.2 (49.3 mg, 94%) as a yellow powder. LC-MS (ESI), $C_{23}H_{33}N_6O$ $[M+H]^+$: m/z=409.2.

Example I.3

(1R,4R)—N[1]-(9-isopropylisoxazolo[5,4-h]quinazolin-2-yl)-N[4]-(pyrimidin-2-yl)cyclohexane-1,4-diamine

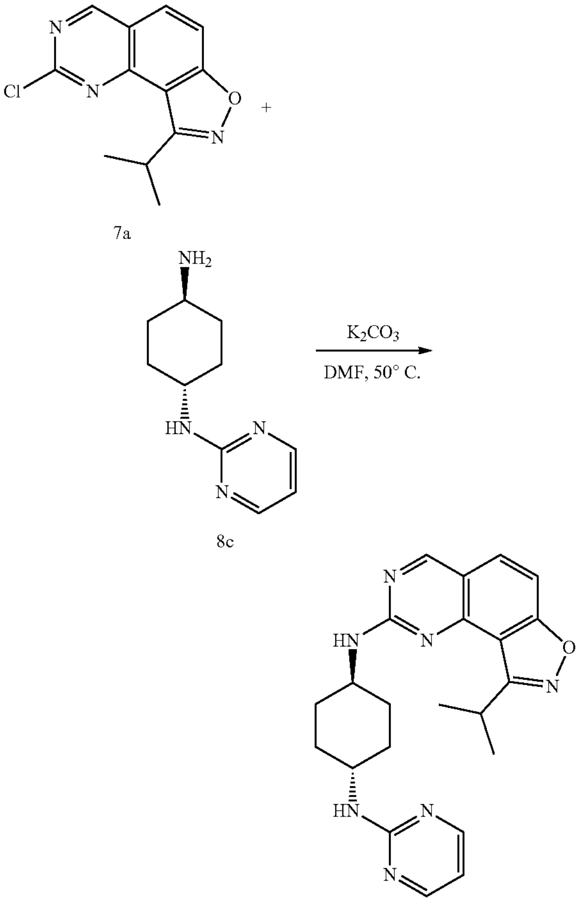

7a

8c

I.3

By referring to the synthetic method of I.1 in Example I.1, compound 1.3 (69.6 mg, 0.173 mmol, 71%) was prepared from 7a (60.0 mg, 0.243 mmol) and hydrochloride of (1R,4R)—N[1]-(pyrimidin-2-yl)cyclohexane-1,4-diamine 8c (110.9 mg, 0.486 mmol). LC-MS (ESI), $C_{22}H_{26}N_7O$ $[M+H]^+$: m/z=404.1.

Example I.4

Hydrochloride of 9-isopropyl-N-(piperidin-4-yl)isoxazolo[5,4-h]quinazolin-2-amine (I.4)

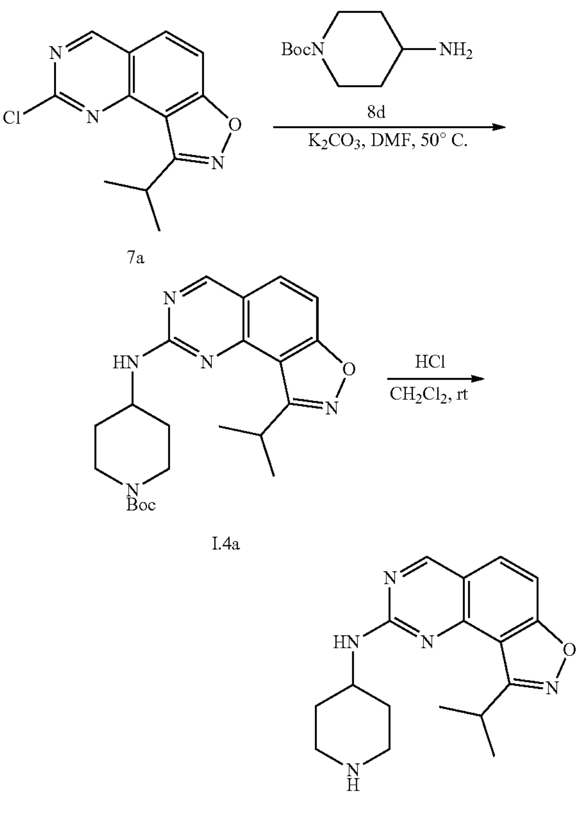

8d

7a

I.4a

I.4

1): Tert-butyl 4-((9-isopropylisoxazolo[5,4-h]quinazolin-2-yl)amino)piperidine-1-carboxylate (I.4a)

By referring to the synthetic method of I.2a in Example I.2, compound I.4a (83 mg, 0.202 mmol, 83%) was prepared from 7a (60.0 mg, 0.243 mmol) and tert-butyl 4-aminopiperidine-1-carboxylate 8d (97 mg, 0.486 mmol). $^1H$ NMR (400 MHz, chloroform-d, ppm) δ 8.94 (s, 1H), 7.72 (d, J=8.8 Hz, 1H), 7.38 (d, J=8.8 Hz, 1H), 5.45 (s, 1H), 4.21-4.06 (m, 3H), 3.90 (p, J=6.9 Hz, 1H), 2.99 (t, J=12.5 Hz, 2H), 2.22-2.09 (m, 2H), 1.58 (d, J=6.9 Hz, 6H), 1.50 (s, 2H), 1.48 (s, 9H).

2): Hydrochloride of 9-isopropyl-N-(piperidin-4-yl)isoxazolo[5,4-h]quinazolin-2-amine (I.4)

By referring to the synthesis method of I.2 in Example I.2, compound 1.4 (55 mg, 0.177 mmol, 93%) was prepared from I.4a (80 mg, 0.19 mmol). $^1H$ NMR (400 MHz, dimethyl sulfoxide-$d_6$, ppm) δ 9.18 (s, 1H), 9.01 (s, 1H), 8.78 (s, 1H), 7.99 (d, J=8.8 Hz, 1H), 7.53 (d, J=8.8 Hz, 1H), 4.11 (s, 1H), 3.92-3.81 (m, 1H), 3.36 (s, 2H), 3.04 (q, J=11.4 Hz, 2H), 2.16 (d, J=13.7 Hz, 2H), 1.91-1.70 (m, 2H), 1.50 (d, J=6.9 Hz, 6H).

Example I.5

9-isopropyl-N-(1-(methylsulfonyl)piperidin-4-yl) isoxazolo[5,4-h]quinazolin-2-amine (I.5)

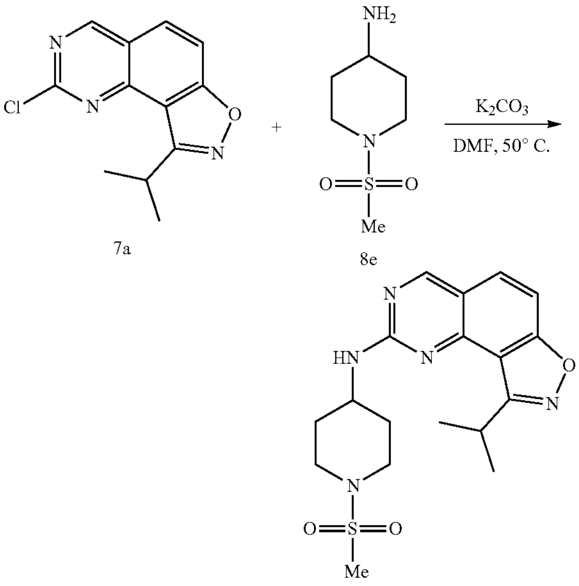

7a

8e

I.5

By referring to the synthesis method of I.1 in Example I.1, compound 1.5 (82.1 mg, 0.211 mmol, 87%) was prepared from 7a (60.0 mg, 0.243 mmol) and 1-methylsulfonyl-4-aminopiperidine 8e (86.6 mg, 0.486 mmol). $^1$H NMR (400 MHz, chloroform-d, ppm) δ 8.97 (s, 1H), 7.74 (d, J=8.8 Hz, 1H), 7.41 (d, J=8.8 Hz, 1H), 5.42 (s, 1H), 4.20-4.09 (m, 1H), 3.91 (dd, J=13.9, 7.0 Hz, 2H), 3.83 (d, J=12.1 Hz, 2H), 2.98 (s, 2H), 2.86 (s, 3H), 2.37-2.25 (m, 2H), 1.76 (td, J=10.5, 6.7 Hz, 2H), 1.59 (d, J=7.6 Hz, 6H).

Example I.6

6-fluoro-9-isopropyl-N-(1-(methylsulfonyl)piperidin-4-yl)isoxazolo[5,4-h]quinazolin-2-amine (I.6)

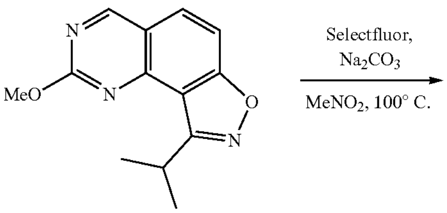

6a

-continued

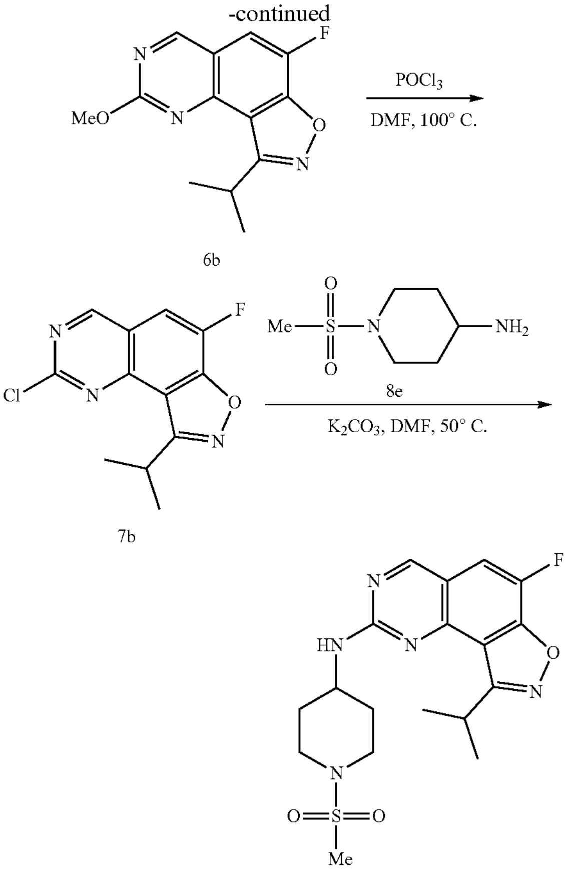

6b

7b

8e

I.6

1): 6-fluoro-9-isopropyl-2-methoxyisoxazolo[5,4-h] quinazoline (6b)

To a solution of 6a (761 mg, 3.13 mmol) in nitromethane (16 mL) were added sodium carbonate (663 mg, 6.26 mmol) and 1-chloromethyl-4-fluoro-1,4-diazoniabicyclo[2.2.2]octane bis(tetrafluoroborate) (Selectfluor, 3.3 g, 9.39 mmol) at room temperature. The mixture was heated to 100° C. and the tube was sealed to react for 8 hours. After cooling to room temperature, the reaction solution was diluted with ethyl acetate (50 mL) and aqueous saturated sodium bicarbonate solution (60 mL). The aqueous phase was separated, and extracted with ethyl acetate (50 mL×2). The organic phases were combined, washed successively with aqueous saturated sodium bicarbonate solution (50 mL×1) and saturated saline solution (50 mL×1), dried (anhydrous sodium sulfate), and filtered. The filtrate was concentrated under reduced pressure. The resulting residue was purified by flash silica gel column chromatography (petroleum ether/ethyl acetate=10:1) to give the titled compound 6b (189 mg, 0.72 mmol, yield 23%) as a pale-yellow solid. LC-MS (ESI), $C_{13}H_{13}FN_3O_2[M+H]^+$: m/z=262.3.

2): 2-chloro-6-fluoro-9-isopropylisoxazolo[5,4-h] quinazoline (7b)

By referring to the synthesis method of 7a in Example I.1, compound 7b (74 mg, 0.28 mmol, 41%) was prepared from 6b (180 mg, 0.69 mmol). LC-MS (ESI), $C_{12}H_{10}ClFN_3O$ $[M+H]^+$: m/z=266.7.

3): 6-fluoro-9-isopropyl-N-(1-(methylsulfonyl)piperidin-4-yl)isoxazolo[5,4-h]quinazolin-2-amine (I.6)

By referring to the synthesis method of I.1 in Example I.1, compound 1.6 (86 mg, 0.21 mmol, 79%) was prepared from 7b (70 mg, 0.26 mmol) and 8e (93 mg, 0.52 mmol). LC-MS (ESI), $C_{18}H_{23}FN_5O_3S$ $[M+H]^+$: m/z=408.1.

Example I.7

6-chloro-9-isopropyl-N-(1-(methylsulfonyl)piperidin-4-yl)isoxazolo[5,4-h]quinazolin-2-amine (I.7)

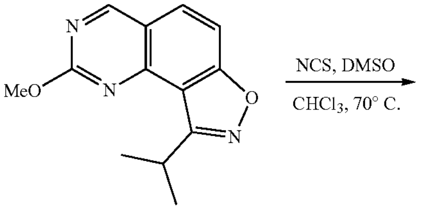

6a

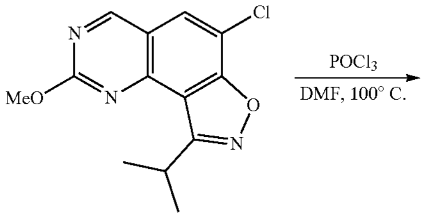

6c

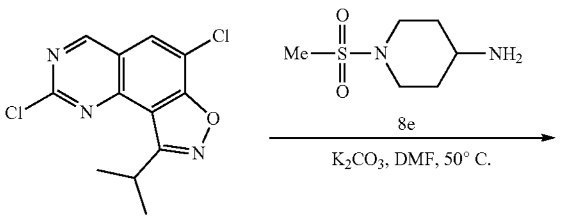

7c

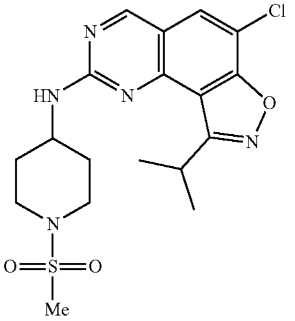

I.7

1): 6-chloro-9-isopropyl-2-methoxyisoxazolo[5,4-h]quinazoline (6b)

To a solution of 6a (300 mg, 1.23 mmol) in chloroform (6 mL) were added dimethylsulfoxide (12 mg, 0.15 mmol) and N-chlorosuccinimide (414 mg, 3.1 mmol) at room temperature. The reaction solution was heated to 70° C., and reacted under stirring at this temperature for 8 hours. After cooling to room temperature, the reaction solution was diluted with ethyl acetate (20 mL) and aqueous saturated sodium bicarbonate solution (30 mL). The aqueous phase was separated, and extracted with ethyl acetate (20 mL×2). The organic phases were combined, washed successively with water (30 mL×1) and saturated saline solution (50 mL×1), dried (anhydrous sodium sulfate), and filtered. The filtrate was concentrated under reduced pressure. The resulting residue was purified by flash silica gel column chromatography (petroleum ether/ethyl acetate=10:1) to give the titled compound 6c (130 mg, 0.47 mmol, yield 38%) as a pale-yellow solid. LC-MS (ESI), $C_{13}H_{13}ClN_3O_2[M+H]^+$: m/z=278.1.

2): 2,6-dichloro-9-isopropylisoxazolo[5,4-h]quinazoline (7b)

By referring to the synthesis method of 7a in Example I.1, compound 7c (59 mg, 0.21 mmol, yield 49%) was prepared from 6c (120 mg, 0.43 mmol). LC-MS (ESI), $C_{12}H_{10}Cl_2N_3O$ $[M+H]^+$: m/z=282.0.

3): 6-chloro-9-isopropyl-N-(1-(methylsulfonyl)piperidin-4-yl)isoxazolo[5,4-h]quinazolin-2-amine (I.7)

By referring to the synthesis method of I.1 in Example I.1, compound 1.7 (63 mg, 0.15 mmol, 86%) was prepared from 7c (50 mg, 0.18 mmol) and 8e (64 mg, 0.36 mmol). LC-MS (ESI), $C_{18}H_{23}ClN_5O_3S$ [M+H]+: m/z=424.1.

Example I.8

6-bromo-9-isopropyl-N-(1-(methylsulfonyl)piperidin-4-yl)isoxazolo[5,4-h]quinazolin-2-amine (I.8)

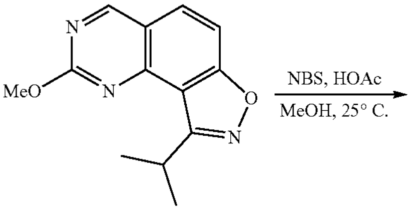

6a

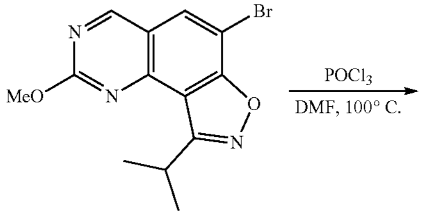

6d

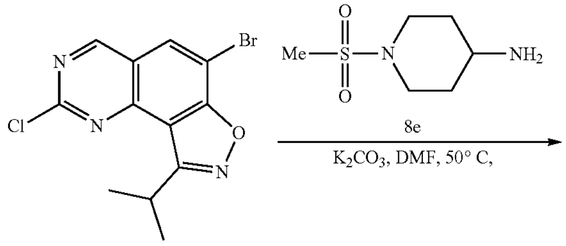

7d

-continued

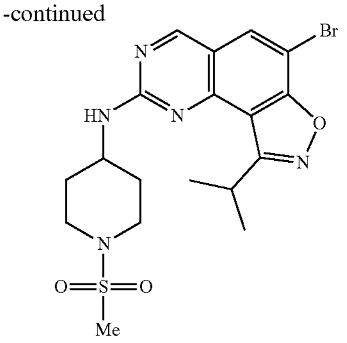

I.8

1): 6-bromo-9-isopropyl-2-methoxyisoxazolo[5,4-h]quinazoline (6d)

To a solution of 6a (I.2 g, 4.93 mmol) in methanol (25 mL) were added acetic acid (889 mg, 14.8 mmol) and N-bromosuccinimide (2.19 g, 12.3 mmol) at room temperature. The reaction was stirred for 4 hours. The reaction solution was concentrated under reduced pressure, and the residue was diluted with ethyl acetate (60 mL) and saturated sodium bicarbonate solution (80 mL). The aqueous phase was separated, and extracted with ethyl acetate (60 mL×2). The organic phases were combined, washed with saturated saline (100 mL×1), dried (anhydrous sodium sulfate), and filtered. The filtrate was concentrated under reduced pressure. The resulting residue was purified by flash silica gel column chromatography (petroleum ether/ethyl acetate=8:1) to give the titled compound 6d (I.4 g, 4.4 mmol, yield 90%) as a pale-yellow solid. 1H NMR (400 MHz, chloroform-d, ppm) δ 9.20 (s, 1H), 8.11 (s, 1H), 4.18 (s, 3H), 3.95 (p, J=6.9 Hz, 1H), 1.61 (d, J=6.9 Hz, 6H).

2): 6-bromo-2-chloro-9-isopropylisoxazolo[5,4-h]quinazoline (7d)

By referring to the synthesis method of 7a in Example I.1, compound 7d (0.44 g, 1.36 mmol, 31%) was prepared from 6d (I.40 g, 4.40 mmol). $^{1}$H NMR (400 MHz, chloroform-d, ppm) δ 9.28 (s, 1H), 8.22 (s, 1H), 3.99 (p, J=6.9 Hz, 1H), 1.60 (d, J=2.5 Hz, 6H).

3): 6-bromo-9-isopropyl-N-(1-(methylsulfonyl)piperidin-4-yl)isoxazolo[5,4-h]quinazolin-2-amine (I.8)

By referring to the synthesis method of I.1 in Example I.1, compound 1.8 (70 mg, 0.15 mmol, 83%) was prepared from 7d (60 mg, 0.18 mmol) and 8e (64 mg, 0.36 mmol). $^{1}$H NMR (400 MHz, chloroform-d, ppm) δ 8.91 (s, 1H), 7.91 (s, 1H), 5.59 (s, 1H), 4.10 (d, J=7.1 Hz, 1H), 3.88 (q, J=7.0 Hz, 1H), 3.82 (dt, J=8.7, 3.9 Hz, 2H), 2.99 (td, J=12.8, 6.4 Hz, 2H), 2.86 (s, 3H), 2.27 (dq, J=12.5, 3.8 Hz, 2H), 1.76 (td, J=14.2, 10.5 Hz, 2H), 1.58 (d, J=7.0 Hz, 6H).

Example I.9

6-(difluoromethyl)-9-isopropyl-N-(1-(methylsulfonyl)piperidin-4-yl)isoxazolo[5,4-h]quinazolin-2-amine (I.9)

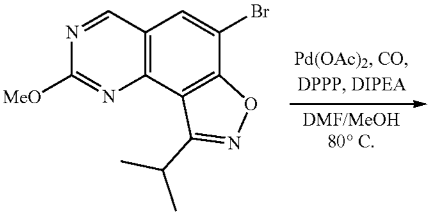

6d

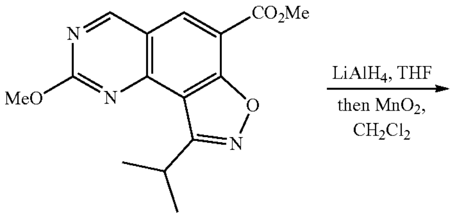

6e

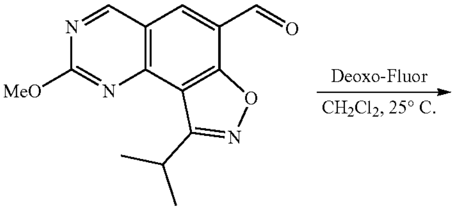

6f

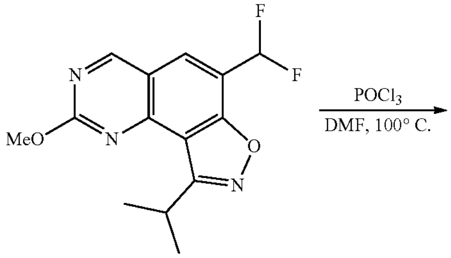

6g

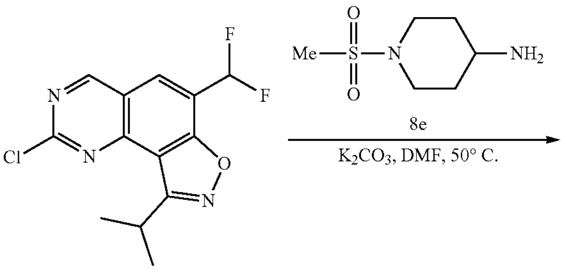

7e

-continued

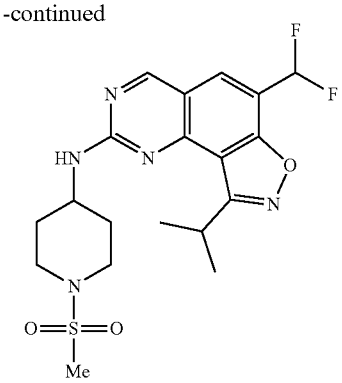

I.9

1): Methyl 9-isopropyl-2-methoxyisoxazolo[5,4-h]quinazolin-6-carboxylate (6e)

To a solution of 6d (622 mg, 1.94 mmol) in N,N-dimethylformamide (10 mL) and methanol (10 mL) were added 1,3-bis(diphenylphosphino)propane (161 mg, 0.39 mmol), palladium acetate (88 mg, 0.39 mmol) and N,N-diisopropylethylamine (2.5 ml, 19.40 mmol) at room temperature. The air in the reaction system was replaced twice by carbon monoxide gas. The mixture was then heated to 80° C. under the protection of carbon monoxide balloon, and reacted overnight. The reaction solution was diluted with ethyl acetate (60 mL) and saturated aqueous sodium bicarbonate solution (50 mL). The organic phase was separated, washed successively with water (50 mL×2) and saturated saline (60 mL×1), dried (anhydrous sodium sulfate), and filtered. The filtrate was concentrated under reduced pressure. The resulting residue was purified by flash silica gel column chromatography (petroleum ether/ethyl acetate=10:1) to give the titled compound 6e (515 mg, 1.71 mmol, yield 88%) as a white solid. $^1$H NMR (400 MHz, chloroform-d, ppm) δ 9.35 (s, 1H), 8.69 (s, 1H), 4.22 (s, 3H), 4.09 (s, 3H), 4.04-3.97 (m, 1H), 1.61 (d, J=7.0 Hz, 6H).

2): 9-isopropyl-2-methoxyisoxazolo[5,4-h]quinazolin-6-methanal (6f)

To a solution of 6e (503 mg, 1.67 mmol) in tetrahydrofuran (9 mL) was added lithium tetrahydroaluminum (95 mg, 2.50 mmol) in batches in an ice bath. The reaction solution was heated to room temperature, and further reacted with stirring for 2 hours. The reaction bottle was then moved into an ice-water bath. The reaction solution was diluted with ethyl acetate (40 mL) and quenched by carefully dropping saturated potassium sodium tartrate aqueous solution (30 mL). The reaction solution was heated to room temperature again, and stirred for 1 h. The aqueous layer was separated and extracted with ethyl acetate (30 mL×2). The organic phases were combined, washed with saturated saline (60 mL×1), dried (anhydrous sodium sulfate), and filtered. The filtrate was concentrated under reduced pressure. The resulting residue was dissolved in dichloromethane (10 mL), and manganese dioxide (30 mg) was added. The mixture was reacted with stirring under reflux overnight, and the reaction solution was concentrated under reduced pressure. The resulting residue was purified by flash silica gel column chromatography (petroleum ether/ethyl acetate=12:1) to give the titled compound 6f (330 mg, 1.22 mmol, yield 73%)

as a pale-yellow solid. 1H NMR (400 MHz, chloroform-d, ppm) δ 10.55 (s, 1H), 9.40 (s, 1H), 8.52 (s, 1H), 4.24 (s, 3H), 4.01 (p, J=7.0 Hz, 1H), 1.64 (d, J=6.9 Hz, 6H).

3): 6-(difluoromethyl)-9-isopropyl-2-methoxyisoxazolo[5,4-h]quinazoline (6g)

To a solution of 6f (176.0 mg, 0.65 mmol) in dichloromethane (4 mL) was added bis(2-methoxyethyl)aminosulfur trifluoride (288.0 mg, 1.30 mmol) at room temperature, and the reaction was stirred overnight. The reaction solution was directly concentrated under reduced pressure, and the resulting residue was purified by flash silica gel column chromatography (petroleum ether/ethyl acetate=8:1) to give the titled compound 6g (162.0 mg, 0.55 mmol, yield 84%) as a pale-yellow solid. $^1$H NMR (400 MHz, chloroform-d, ppm) δ 9.33 (s, 1H), 8.17 (t, 1H), 4.22 (s, 3H), 3.99 (p, J=7.0 Hz, 1H), 1.63 (d, J=6.9 Hz, 6H).

4): 2-chloro-6-(difluoromethyl)-9-isopropylisoxazolo[5,4-h]quinazoline (7e)

By referring to the synthesis method of 7a in Example I.1, compound 7e (54.0 mg, 0.18 mmol, 35%) was prepared from 6g (151.0 mg, 0.51 mmol). $^1$H NMR (400 MHz, chloroform-d, ppm) δ 9.41 (s, 1H), 8.27-8.26 (m, 1H), 7.21 (t, 1H), 4.02 (p, J=7.0 Hz, 1H), 1.61 (d, J=6.9 Hz, 6H).

5): 6-(difluoromethyl)-9-isopropyl-N-(1-(methylsulfonyl)piperidin-4-yl)isoxazolo[5,4-h]quinazolin-2-amine (I.9)

By referring to the synthesis method of I.1 in Example I.1, compound 1.9 (62.0 mg, 0.14 mmol, 79%) was prepared from 7e (54.0 mg, 0.18 mmol) and 8e (64.0 mg, 0.36 mmol). $^1$H NMR (400 MHz, chloroform-d, ppm) δ 9.02 (s, 1H), 7.96 (d, J=1.7 Hz, 1H), 7.11 (s, 1H), 5.60 (s, 1H), 4.13 (t, J=7.1 Hz, 1H), 3.90 (t, J=6.9 Hz, 1H), 3.86-3.76 (m, 2H), 3.04-2.94 (m, 2H), 2.86 (s, 3H), 2.35-2.22 (m, 2H), 1.82-1.71 (m, 2H), 1.59 (d, J=7.0 Hz, 6H).

Example I.10

(9-isopropyl-2-((1-(methylsulfonyl)piperidin-4-yl)amino)isoxazolo[5,4-h]quinazolin-6-yl)methanol (I.10)

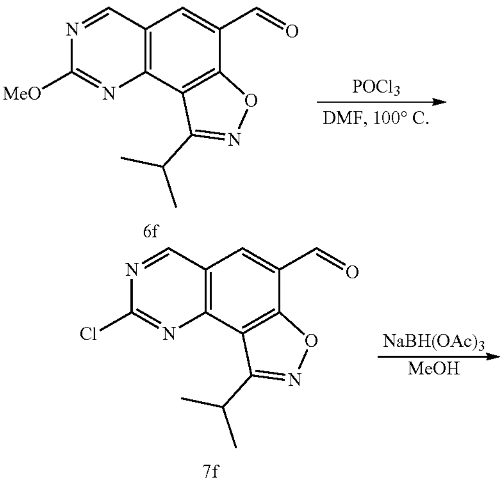

-continued

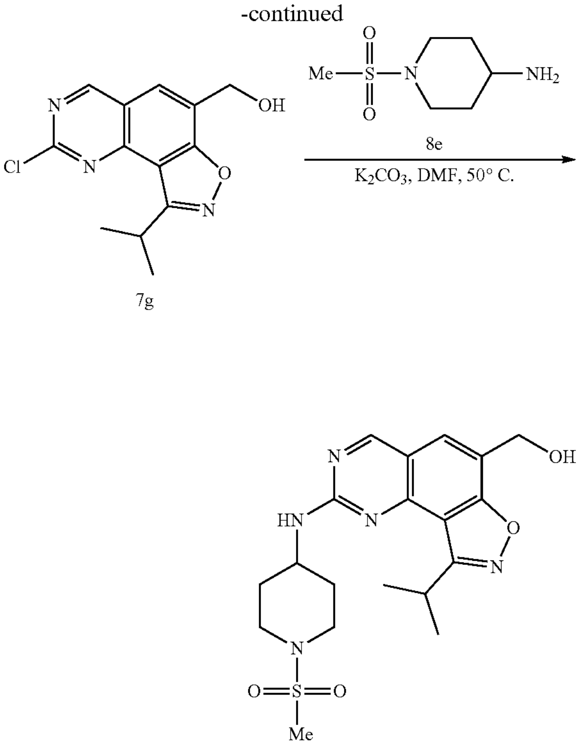

7g

I.10

1): 2-chloro-9-isopropylisoxazolo[5,4-h]quinazolin-6-methanal (7f)

By referring to the synthesis method of 7a in Example I.1, compound 7f (75.0 mg, 0.27 mmol, 51%) was prepared from 6f (144.0 mg, 0.53 mmol). $^1H$ NMR (400 MHz, chloroform-d) δ 10.63 (s, 1H), 9.48 (s, 1H), 8.60 (s, 1H), 4.03 (p, J=6.9 Hz, 1H), 1.62 (d, J=6.9 Hz, 6H).

2): (2-chloro-9-isopropylisoxazolo[5,4-h]quinazolin-6-yl)methanol (7g)

To a solution of 7f (85.0 mg, 0.31 mmol) in methanol (2 mL) was added sodium triacetyl borohydride (100.0 mg, 0.47 mmol) in an ice bath. The reaction was warmed to room temperature and reacted for 6 hours.

After concentrating under reduced pressure to remove most of the solvent, the reaction solution was diluted with dichloromethane (30 mL) and saturated aqueous sodium bicarbonate solution (30 mL), and the aqueous layer was separated and extracted with dichloromethane (30 mL×2). The organic phases were combined, washed with saturated saline (50 mL×1), dried (anhydrous sodium sulfate), and filtered. The filtrate was concentrated under reduced pressure. The resulting residue was purified by flash silica gel column chromatography (petroleum ether/ethyl acetate=4:1) to give the titled compound 7g (69.0 mg, 0.25 mmol, yield 81%) as a pale-yellow solid. LC-MS (ESI), $C_{13}H_{13}ClN_3O_2$ $[M+H]^+$: m/z=278.1.

3): (9-isopropyl-2-((1-(methylsulfonyl)piperidin-4-yl)amino)isoxazolo[5,4-h]quinazolin-6-yl)methanol (I.10)

By referring to the synthesis method of I.1 in Example I.1, compound 1.10 (59.0 mg, 0.14 mmol, yield 79%) was prepared from 7g (50.0 mg, 0.18 mmol) and 8e (64.0 mg, 0.36 mmol). $^1H$ NMR (400 MHz, chloroform-d, ppm) δ 8.96 (s, 1H), 7.76 (s, 1H), 5.44 (s, 1H), 5.06 (d, J=3.6 Hz, 2H), 4.13 (s, 1H), 3.89 (p, J=6.9 Hz, 1H), 3.81 (d, J=12.1 Hz, 2H), 3.72 (q, J=7.0 Hz, 1H), 2.98 (t, J=11.5 Hz, 2H), 2.85 (s, 3H), 2.28 (d, J=12.9 Hz, 2H), 1.79-1.73 (m, 2H), 1.58 (d, J=7.0 Hz, 6H).

Example I.11

9-isopropyl-N-(1-(methylsulfonyl)piperidin-4-yl)isoxazolo[5,4-h]quinazolin-6-d-2-amine (I.11)

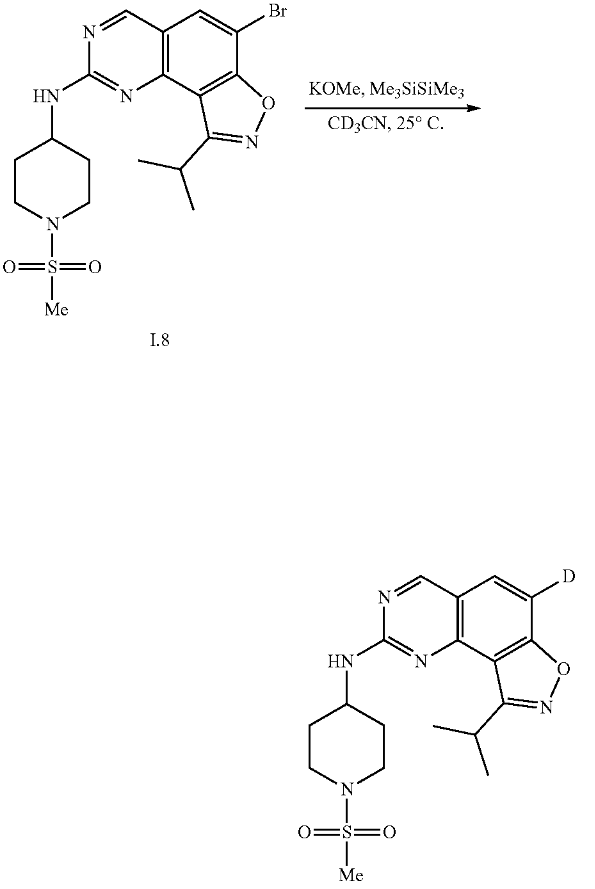

I.8

I.11

To a solution of 1.8 (30.0 mg, 0.06 mmol) in deuterated acetonitrile (1 mL) were added potassium methoxide (9.0 mg, 0.13 mmol) and hexamethyldisilane (18.0 mg, 1.20 mmol) at room temperature. After the completion of addition, the reaction was continued for 12 hours. The reaction solution was diluted with ether (10 mL) and water (10 mL), and the aqueous layer was separated and extracted with ether (10 mL×2). The organic phases were combined, washed with saturated saline (15 mL×1), dried (anhydrous sodium sulfate), and filtered. The filtrate was concentrated under reduced pressure. The resulting residue was purified by flash silica gel column chromatography (dichloromethane/methanol=100:1) to give the titled compound 1.11 (19.0 mg, 0.05 mmol, yield 83%) as a pale-yellow solid. LC-MS (ESI), $C_{18}H_{23}DN_5O_3S$ $[M+H]^+$: m/z=391.2.

Example I.12

9-isopropyl-6-methyl-N-(1-(methylsulfonyl)piperidin-4-yl)isoxazolo[5,4-h]quinazolin-2-amine (I.12)

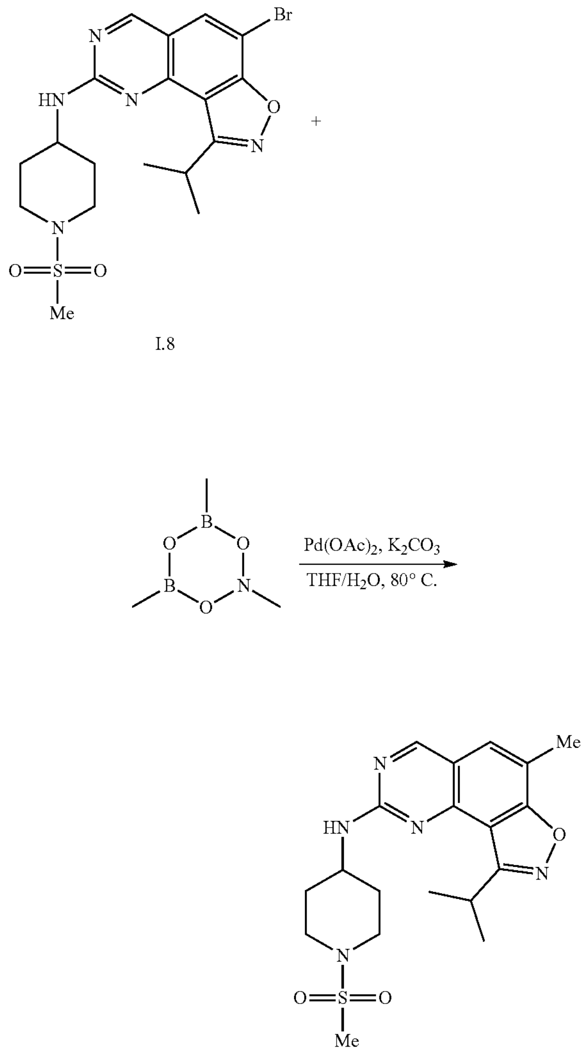

I.8

I.12

To a solution of 1.8 (30.0 mg, 0.060 mmol) in tetrahydrofuran (1 mL) and water (0.1 mL) were added palladium acetate (2.70 mg, 0.012 mmol) and potassium carbonate (83.0 mg, 0.600 mmol) at room temperature. After replacing the air in the reaction system with argon twice, the mixture was heated to 80° C., and the tube was sealed to react for overnight. The reaction solution was diluted with ethyl acetate (10 mL) and saturated sodium bicarbonate aqueous solution (10 mL). The aqueous phase was separated, and extracted with (10 mL×2). The organic phases were combined, washed with saturated saline (10 mL×1), dried (anhydrous sodium sulfate), filtered, and concentrated under reduced pressure. The resulting residue was purified by flash silica gel column chromatography (dichloromethane/methanol=80:1) to give the titled compound 1.12 (14.0 mg, 0.035 mmol, yield 58%) as a white solid. LC-MS (ESI), $C_{19}H_{26}N_5O_3S$ $[M+H]^+$: m/z=404.2.

Example I.13

(1R,2S)-1-methyl-2-(2-((1-(methylsulfonyl)piperidin-4-yl)amino)isoxazolo[5,4-h]quinazolin-9-yl) cyclo pentan-1-ol (I.13)

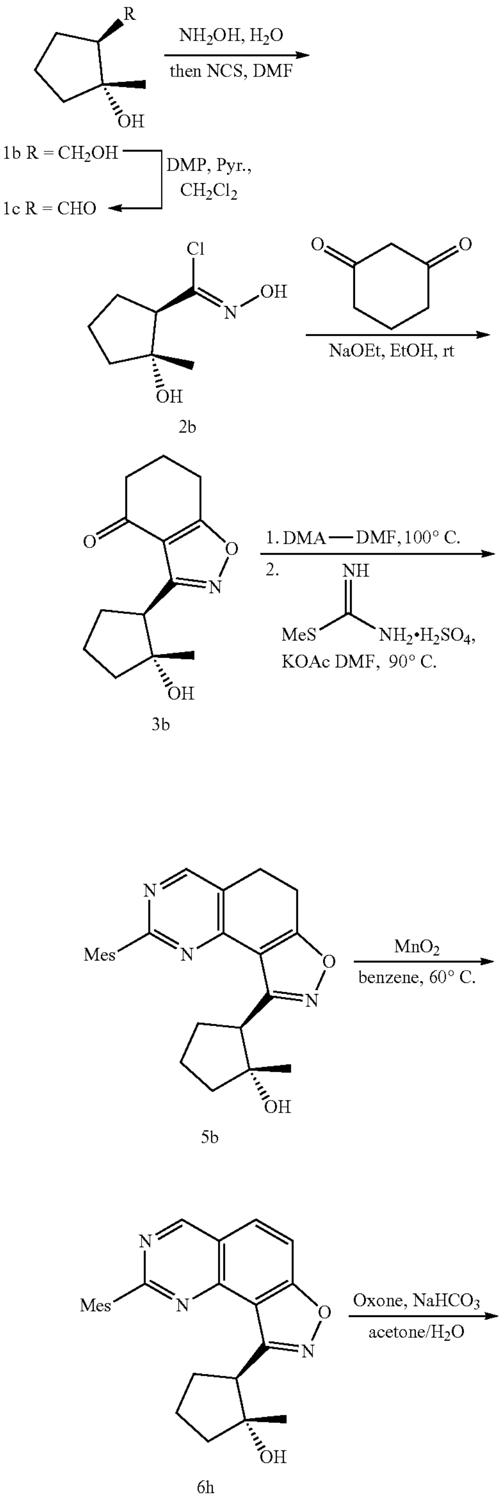

2b

3b

5b

6h

-continued

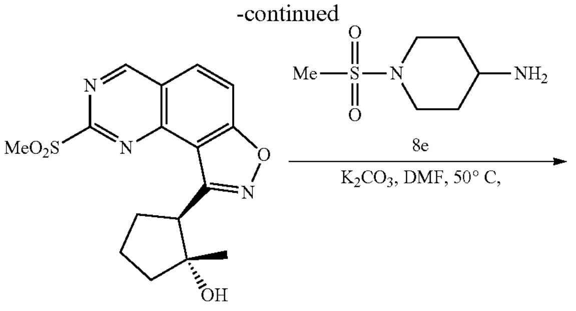

7h

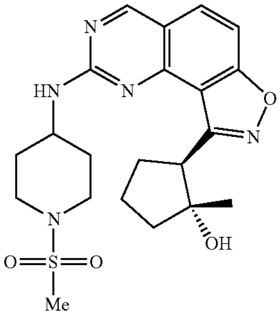

I.13

1): (1R,2S)-2-(hydroxymethyl)-1-methylcyclopentan-1-ol (1b)

1b (650 mg, 5.0 mmol, yield 41%) was prepared under the conditions reported in reference document[1].

[1] G. A. Molander, J. A. McKie. Samnium(II) iodide-induced reductive cyclization of unactivated olefinic ketones. Sequential radical cyclization/intermolecular nucleophilic addition and substitution reactions. J. *Org. Chem.* 1992, 57, 11, 3132-3139

2): (1R,2R)-2-hydroxy-2-methylcyclopentan-1-methanal (1c)

To a solution of 1b (0.62 g, 4.8 mmol) in dichloromethane (24 mL) were added pyridine (3.9 mL, 48.0 mmol) and Dess-Martin Oxidant (4.07 g, 9.6 mmol) at room temperature. After 3 hours of reaction, the reaction solution was diluted with dichloromethane (60 mL) and saturated sodium bicarbonate aqueous solution (60 mL). The organic phase was separated, then washed with saturate saline (60 mL×1), dried (anhydrous sodium sulfate), and filtered. The filtrate was concentrated under reduced pressure. The resulting residue was purified by flash silica gel column chromatography (petroleum ether/ethyl acetate=3:1) to give the titled compound 1c (0.50 g, 3.9 mmol, yield 81%) as a pale-yellow oil. LC-MS (ESI), $C_7H_{13}O_2$[M+H]+: m/z=129.1.

3): (1R,2R,Z)—N,2-dihydroxy-2-methylcyclopentane-1-carbimidoyl chloride (2b)

By referring to the synthesis method of 2a in Example I.1, compound 2b (310.0 mg, 1.75 mmol, 73%) was prepared from 1c (307.0 mg, 2.40 mmol). LC-MS (ESI), $C_7H_{12}ClNO_2Na$ $[M+Na]^+$: m/z=200.1.

4): 3-((1S,2R)-2-hydroxy-2-methylcyclopentyl)-6,7-dihydrobenzo[d]isoxazol-4(5H)-one (3b)

By referring to the synthesis method of 3a in Example I.1, compound 3b (235 mg, 1.0 mmol, 60%) was prepared from 2b (301.0 mg, 1.7 mmol) and 1,3-cyclohexanedione (228 mg, 2.04 mmol). LC-MS (ESI), $C_{13}H_{18}NO_3$ $[M+H]^+$: m/z=236.1.

5): (1R,2S)-1-methyl-2-(2-(methylthio)-5,6-dihydroisoxazolo[5,4-h]quinazolin-9-yl)cyclopentan-1-ol (5b)

A solution of 3b (207.0 mg, 0.88 mmol) in N,N-dimethylformamide dimethylacetal (I.7 mL, 13.20 mol) and N,N-dimethylformamide (5 mL) was stirred and reacted at 100° C. for 12 hours. After cooling to room temperature, the reaction solution was concentrated under reduced pressure. The obtained brown oil was redissolved in N,N-dimethylformamide (5 mL). S-methyl isothiourea sulfate (497.0 mg, 2.64 mmol) and anhydrous potassium acetate (518.0 mg, 5.28 mmol) were added. The reaction was then heated to 90° C. and stirred for 12 hours. After cooling to room temperature, the reaction solution was diluted with water (20 mL) and extracted with ethyl acetate (20 mL×3). The organic phases were combined, washed successively with water (10 mL×3) and saturated saline (50 mL×1), dried with anhydrous sodium sulfate, and filtered. The filtrate was concentrated and then purified by flash silica gel column chromatography (petroleum ether/ethyl acetate=3:1) to give the title compound 5b (84.0 mg, 0.280 mmol, two-step yield 32%) as a pale-yellow solid. LC-MS (ESI), $C_{15}H_{20}N_3O_2S$ [M+H]+: m/z=318.3.

6): (1R,2S)-1-methyl-2-(2-(methylthio)isoxazolo[5,4-h]quinazolin-9-yl)cyclopentan-1-ol (6h)

By referring to the synthesis method of 6a in Example I.1, compound 6h (60 mg, 0.2 mmol, 83%) was prepared from 5b (72.0 mg, 0.240 mmol). LC-MS (ESI), $C_{16}H_{18}N_3O_2S$ $[M+H]^+$: m/z=316.2.

7): (1R,2S)-1-methyl-2-(2-(methylsulfonyl)isoxazolo[5,4-h]quinazolin-9-yl)cyclopentan-1-ol (7h)

To a solution of 6h (54.0 mg, 0.180 mmol) in acetone (1 mL) and water (0.5 mL) was added potassium peroxymonosulfonate (62.0 mg, 0.180 mmol) in batches at room temperature, and the mixture was reacted for 4 hours. After concentrating under reduced pressure to remove most of the solvent, the reaction solution was diluted with ethyl acetate (5 mL) and semi-saturated sodium bicarbonate aqueous solution (5 mL). The aqueous layer was separated, and extracted with ethyl acetate (6 mL×2). The organic phases were combined, washed with saturated saline (10 mL×1), dried with anhydrous sodium sulfate, and filtered. The filtrate was concentrated and then purified by flash silica gel column chromatography (dichloromethane/methanol=60:1) to give the titled compound 7h (45.0 mg, 0.150 mmol, yield 83%) as a yellow solid. LC-MS (ESI), $C_{16}H_{18}N_3O_4S$ $[M+H]^+$: m/z=348.1.

8): (1R,2S)-1-methyl-2-(2-((1-(methylsulfonyl)piperidin-4-yl)amino)isoxazolo[5,4-h]quinazolin-9-yl)cyclopentan-1-ol (I.13)

By referring to the synthesis method of 0.1 in Example I.1, compound 1.13 (35.0 mg, 0.079 mmol, 80%) was prepared from 7h (30.0 mg, 0.099 mmol) and 8e (35 mg, 0.198 mmol). LC-MS (ESI), $C_{21}H_{28}N_5O_4S$ $[M+H]^+$: m/z=446.2.

Example I.14

(1R,2S)-2-(6-(difluoromethyl)-2-((1-(methylsulfonyl)piperidin-4-yl)amino)isoxazolo[5,4-h]quinazolin-9-yl)-1-methylcyclopentan-1-ol (I.14)

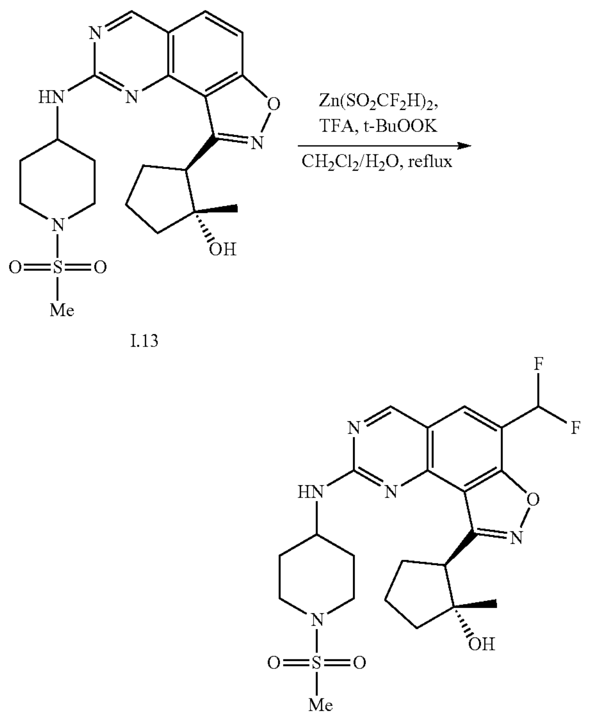

I.13

I.14

1): The reagent of zinc difluoromethanesulfinate was prepared by referring to the method reported by Phil S. Baran's research group[2].

[2] Y. Fujiwara, J. A. Dixon, F. O. Hara, Phil S. Baran. et al. C—H functionalization of heterocycles. *Nature* 2012. 492, 95

2): (1R,2S)-2-(6-(difluoromethyl)-2-((1-(methylsulfonyl)piperidin-4-yl)amino)isoxazolo[5,4-h]quinazolin-9-yl)-1-methylcyclopentan-1-ol (I.14)

Under the protection of argon, freshly prepared zinc difluoromethanesulfinate (67.0 mg, 0.201 mmol) was added into a solution of 1.13 (30.0 mg, 0.067 mmol) in dichloromethane (1 mL) and water (0.4 mL) cooled by ice water bath. Trifluoroacetic acid (31.0 μL, 0.402 mmol) was added, and then tert-butanol peroxide (20.0 μL, 0.402 mmol) was slowly added dropwise to the reaction solution. After the addition was completed, the mixture was heated to reflux and reacted for 24 hours. The reaction solution was diluted with ethyl acetate (5 mL) and saturated aqueous sodium bicarbonate solution (5 mL). The aqueous phase was separated, and extracted with ethyl acetate (5 mL×2). The organic phases were combined, washed with saturated saline (15 mL×1), dried (anhydrous sodium sulfate), and filtered. The filtrate was concentrated under reduced pressure. The resulting residue was purified by flash silica gel column chromatography (dichloromethane/methanol=80:1) to give the titled compound 1.14 (8.0 mg, 0.015 mmol, yield 23%) as a pale-yellow solid. LC-MS (ESI), $C_{22}H_{28}F_2N_5O_4S$ $[M+H]^+$: m/z=496.2.

Example I.15

9-isopropyl-N-(1-(methylsulfonyl)piperidin-4-yl)-5,6-dihydroisoxazolo[5,4-h]quinazolin-2-amine (I.15)

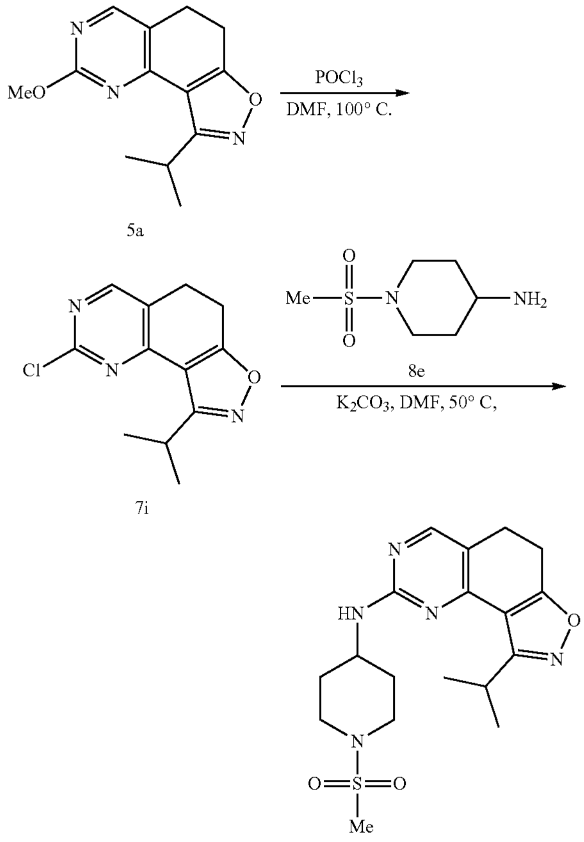

5a

7i

I.15

1): 2-chloro-9-isopropyl-5,6-dihydroisoxazolo[5,4-h]quinazoline (7i)

By referring to the synthesis method of 7a in Example I.1, compound 7i (44.0 mg, 0.180 mmol, 45%) was prepared from 5a (100.0 mg, 0.410 mmol). LC-MS (ESI), $C_{12}H_{13}ClN_3O$ $[M+H]^+$: m/z=250.1.

2): 9-isopropyl-N-(1-(methylsulfonyl)piperidin-4-yl)-5,6-dihydroisoxazolo[5,4-h]quinazolin-2-amine (I.15)

By referring to the synthesis method of 0.1 in Example I.1, compound 1.15 (50.9 mg, 0.130 mmol, 81%) was prepared from 7i (40.0 mg, 0.160 mmol) and 8e (57.0 mg, 0.320 mmol). LC-MS (ESI), $C_{18}H_{26}N_5O_3S$ $[M+H]^+$: m/z=392.2.

Example I.16

Hydrochloride of (1R,4R)—N[1]-(9-isopropylisoxazolo[5,4-h]quinazolin-2-yl)-N[4]-(piperidin-4-yl)cyclohexane-1,4-diamine (I.16)

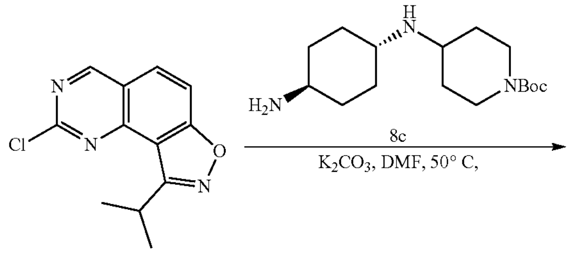

7a

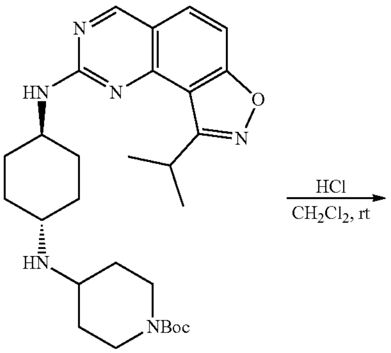

I.16a

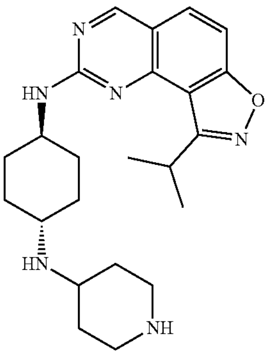

I.16

1)

Tert-butyl 4-(((1R,4R)-4-((9-isopropylisoxazolo[5,4-h]quinazolin-2-yl)amino)cyclohexyl)amino)piperidine-1-carboxylate (I.16a)

To a solution of 7a (60.0 mg, 0.243 mmol) and tert-butyl 4-(((1R,4R)-4-aminocyclohexyl)amino)piperidine-1-carboxylate 8c(144.4 mg, 0.486 mmol) in N,N-dimethylformamide (2 mL) was added potassium carbonate (67.0 mg, 0.486 mmol). The mixture was heated to 50° C., and reacted at this temperature under stirring for 3 hours. The reaction was put into ice-water bath, and diluted with ethyl acetate (15 mL) and water (4 mL). Aqueous hydrochloric acid solution (0.1 N) was slowly added dropwise with vigorous stirring to adjust the pH to about 8. The aqueous phase was separated. The organic phase was washed successively with water (3 mL×2) and saturated saline (5 mL), dried (anhydrous sodium sulfate), filtered by suction, and concentrated. The resulting residue was purified by flash silica gel column chromatography (dichloromethane/methanol=100:1) to give the title compound I.16a (106.2 mg, 0.209 mmol, 86%) as a pale-yellow solid. LC-MS (ESI), $C_{28}H_{41}N_6O_3$ $[M+H]^+$: m/z=509.3.

2): (1R,4R)—N[1]-(9-isopropylisoxazolo[5,4-h]quinazolin-2-yl)-N[4]-(piperidin-4-yl)cyclohexane-1,4-diamine (I.16)

I.16a (60 mg, 0.118 mmol) was dissolved in dichloromethane (2 mL), and a solution of hydrogen chloride in 1,4-dioxane (4 M, 0.3 mL) was added. After stirring at room temperature for 2 hours, the reaction solution was filtered by suction. The obtained filter residue was dried in vacuum by oil pump to constant weight to give the hydrochloride of the title compound 1.16 (49.3 mg, 94%) as a yellow powder. LC-MS (ESI), $C_{23}H_{33}N_6O$ $[M+H]^+$: m/z=409.2.

Example II.1

Hydrochloride of (1R,4R)—N'-(1-isopropyl-1H-[1,2,3]triazolo[4,5-h]quinazolin-8-yl)cyclohexane-1,4-diamine (II.1)

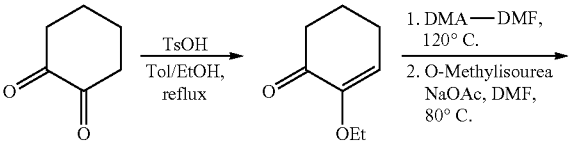

9a 10a

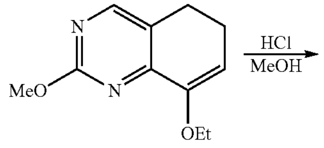

11a

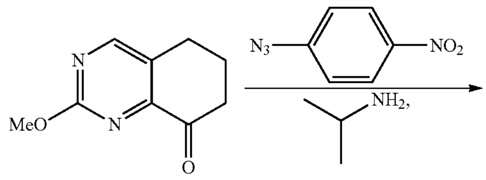

12a 13a

HOAc
Tol, 100° C.

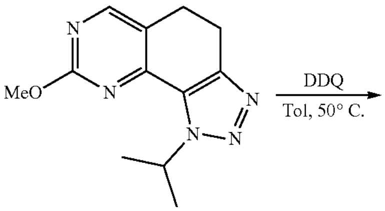

14a

-continued

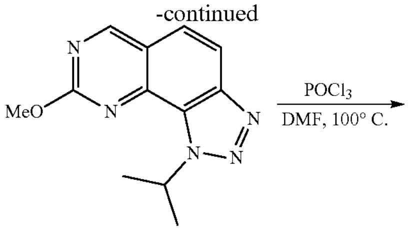

15a

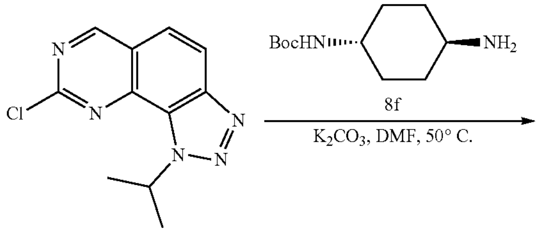

16a

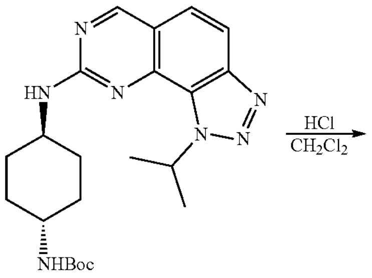

II.1a

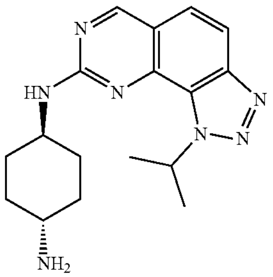

II.1

1): 2-ethoxy-cyclohex-2-en-1-one (10a)

1,2-cyclohexanedione 9a (90 g, 803.2 mmol) and p-toluenesulfonic acid monohydrate (15.3 g, 80.3 mmol) were suspended in toluene/ethanol (v/v=2:1, 1000 mL). The mixture was heated to reflux and the reaction was continued for 36 hours. After the reaction solution was cooled to room temperature, most of the solvent was removed by distillation under reduced pressure. Then, the reaction solution was neutralized with saturated aqueous sodium bicarbonate solution (500 mL) and extracted with dichloromethane (200 mL×3). The organic phases were combined, dried (anhydrous sodium sulfate), filtered by suction, and concentrated. The resulting residue was purified by flash silica gel column chromatography (petroleum ether/ethyl acetate=20:1) to give the titled compound 10a (91.1 g, 650.6 mmol, 81%) as pale-yellow oil. $^1$H NMR (400 MHz, chloroform-d, ppm) δ 5.84 (t, J=4.6 Hz, 1H), 3.74 (q, J=7.0 Hz, 2H), 2.56-2.45 (m, 2H), 2.41 (q, J=5.5 Hz, 3H), 1.95 (p, J=6.2 Hz, 2H), 1.36 (t, J=7.0 Hz, 3H).

2): 8-ethoxy-2-methoxy-5,6-dihydroquinazoline (11a)

A solution of 10a (21 g, 150.0 mmol) and N,N-dimethylformamide dimethylacetal (99.3 mL, 750.0 mmol) in N,N-dimethylformamide (300 mL) was stirred at 120° C. for 13 hours. The reaction solution was cooled to room temperature, and then concentrated under reduced pressure to give the enamine intermediate as a brown oil. The crude product could be used directly in the next reaction without further purification. LC-MS (ESI), $C_{13}H_{20}N_3O$ $[M+H]^+$: m/z=234.2.

The crude product obtained in the previous step, O-methylisourea sulfate (73.9 g, 300.0 mmol) and anhydrous sodium acetate (49.2 g, 600.0 mmol) were suspended in N,N-dimethylformamide (500 mL). The mixture was heated to 80° C. and reacted for 24 hours. After cooling to room temperature, the reaction solution was diluted with dichloromethane (500 mL), filtered by suction, and concentrated. The resulting residue was purified by flash silica gel column chromatography (petroleum ether/ethyl acetate=1:1) to give the title compound 11a (16.4 g, 79.5 mmol, 53%) as a pale-yellow solid. 1H NMR (400 MHz, chloroform-d, ppm) δ 8.20 (s, 1H), 5.46 (t, J=4.7 Hz, 1H), 3.99 (s, 3H), 3.92 (q, J=7.0 Hz, 2H), 2.70 (t, J=7.9 Hz, 2H), 2.40 (td, J=7.9, 4.8 Hz, 2H), 1.44 (t, J=7.0 Hz, 3H).

3): 2-methoxy-6,7-dihydroquinazolin-8(5H)-one (12a)

To a solution of 11a (15 g, 72.8 mmol) in methanol (200 mL) was slowly added hydrogen chloride (37.5 mL, 4 M in dioxane, 150 mmol) in an ice-water bath. The mixture was warmed to room temperature and reacted overnight. Saturated sodium bicarbonate aqueous solution was added dropwise to the reaction solution in an ice-water bath until pH was about 8. The reaction solution was extracted with dichloromethane (200 mL×3). The organic phases were combined, dried (anhydrous sodium sulfate), filtered by suction, and concentrated to give the title compound 12a (12.0 g, 67.4 mmol, 93%) as a pale-yellow solid. 1H NMR (400 MHz, chloroform-d, ppm) δ 8.66 (s, 1H), 4.05 (s, 3H), 2.92 (t, J=6.1 Hz, 2H), 2.84-2.72 (m, 2H), 2.18 (ddd, J=12.7, 7.2, 5.7 Hz, 2H).

4): 1-isopropyl-8-methoxy-4,5-dihydro-1H-[1,2,3]triazolo[4,5-H]quinazoline (14a)

12a (II.5 g, 64.6 mmol) was dissolved in toluene (300 mL), and isopropylamine 13a (16.6 mL, 193.8 mmol), 1-azido-4-nitrobenzene (21.2 g, 129.2 mmol) and glacial acetic acid (I.1 mL, 19.4 mmol) were added in sequence at room temperature. The reaction was heated to 100° C., and stirred overnight. The reaction solution was cooled to room temperature, and concentrated under reduced pressure. The resulting residue was purified by flash silica gel column chromatography (petroleum ether/ethyl acetate=3:1) to give the title compound 14a (9.2 g, 37.5 mmol, 58%) as a pale-yellow solid. 1H NMR (400 MHz, chloroform-d, ppm) δ 8.38 (s, 1H), 5.73 (p, J=6.7 Hz, 1H), 4.03 (s, 3H), 3.08 (ddd, J=7.9, 6.6, 1.8 Hz, 2H), 3.05-2.92 (m, 2H), 1.70 (d, J=6.7 Hz, 6H).

5): 1-isopropyl-8-methoxy-1H-[1,2,3]triazolo[4,5-H]quinazoline (15a)

2,3-dichloro-5,6-dicyano-1,4-benzoquinone (23.6 g, 104.1 mmol) was added to a solution of 14a (8.5 g, 34.7 mmol) in toluene (200 mL). The reaction was heated to 50° C., and continued for 24 hours. After concentration under reduced pressure, the resulting residue was purified by flash silica gel column chromatography (petroleum ether/ethyl acetate=20:1 to 6:1) to give the title compound 15a (6.4 g, 26.4 mmol, 76%) as a pale-yellow solid. 1H NMR (400 MHz, chloroform-d, ppm) δ 9.32 (s, 1H), 8.00 (d, J=8.8 Hz, 1H), 7.68 (d, J=8.9 Hz, 1H), 6.15 (p, J=6.7 Hz, 1H), 4.21 (s, 3H), 1.87 (d, J=6.8 Hz, 6H).

6): 8-chloro-1-isopropyl-1H-[1,2,3]triazolo[4,5-H]quinazoline (16a)

To a solution of 15a (5.8 g, 23.9 mmol) in N,N-dimethylformamide (200 mL) was slowly added dropwise phosphorus oxychloride (22.3 mL, 239.0 mmol) in an ice-water bath. After the addition was completed, the mixture was heated to 100° C. and reacted for 1 hour. The reaction was put into ice-water bath again, and diluted with ethyl acetate (600 mL). Aqueous sodium hydroxide solution (1 N) was slowly added dropwise with vigorous stirring to adjust the pH to about 8. The organic phase was separated, washed successively with water (80 mL×3) and saturated saline (80 mL×1), dried (anhydrous sodium sulfate), filtered by suction, and concentrated. The resulting residue was purified by flash silica gel column chromatography (petroleum ether/ethyl acetate=4:1) to give the title compound 16a (4.7 g, 19.1 mmol) as a pale-yellow solid. $^1$H NMR (400 MHz, chloroform-d, ppm) δ 9.39 (s, 1H), 8.21 (dd, J=8.9, 0.8 Hz, 1H), 7.76 (dd, J=8.9, 0.9 Hz, 1H), 6.14 (p, J=6.7 Hz, 1H), 1.94-1.80 (m, 6H).

7): Tert-butyl ((1R,4R)-4-((1-isopropyl-1H-[1,2,3]triazolo[4,5-h]quinazolin-8-yl)amino)cyclohexyl)carbamate (II.1a)

To a solution of 16a (60.0 mg, 0.243 mmol) and trans-tert-butyl (4-aminocyclohexyl)carbamate 8f (104.0 mg, 0.486 mmol) in N,N-dimethylformamide (2 mL) was added potassium carbonate (67.0 mg, 0.486 mmol). The reaction was heated to 50° C., and reacted at this temperature for 3 hours under stirring. The reaction was put into ice-water bath, and diluted with ethyl acetate (15 mL) and water (4 mL). Aqueous hydrochloric acid solution (0.1 N) was slowly added dropwise with vigorous stirring to adjust the pH to about 8. The aqueous phase was separated. The organic phase was washed successively with water (3 mL×2) and saturated saline (5 mL), dried (anhydrous sodium sulfate), filtered by suction, and concentrated. The resulting residue was purified by flash silica gel column chromatography (dichloromethane/methanol=100:1) to give the title compound II.1a (74.0 mg, 0.175 mmol, 72%) as a pale-yellow solid. $^1$H NMR (400 MHz, chloroform-d, ppm) δ 8.99 (s, 1H), 7.74 (d, J=8.8 Hz, 1H), 7.47 (d, J=8.8 Hz, 1H), 6.13 (p, J=6.7 Hz, 1H), 5.41 (s, 1H), 4.48 (s, 1H), 3.89 (s, 1H), 3.53 (s, 1H), 2.29 (d, J=10.9 Hz, 2H), 2.16 (d, J=11.4 Hz, 2H), 1.82 (d, J=6.7 Hz, 6H), 1.72 (s, 1H), 1.46 (s, 9H), 1.43-1.28 (m, 4H).

8): Hydrochloride of (1R,4R)-N1-(1-isopropyl-1H-[1,2,3]triazolo[4,5-h]quinazolin-8-yl)cyclohexane-1,4-diamine (II.1)

By referring to the synthesis method of I.2 in Example I.2, hydrochloride of compound II.1 (60.0 mg, 0.167 mmol, 95%) was prepared from II.1a (74.0 mg, 0.175 mmol). $^1$H NMR (400 MHz, dimethyl sulfoxide-$d_6$, ppm) δ 9.20 (s, 1H), 8.15 (d, J=5.2 Hz, 2H), 7.88 (s, 1H), 7.66 (t, J=7.9 Hz, 2H), 6.07 (s, 1H), 3.80 (s, 1H), 3.05 (s, 1H), 2.09 (t, J=16.2 Hz, 4H), 1.75 (d, J=6.7 Hz, 6H), 1.56 (q, J=12.1 Hz, 2H), 1.48-1.36 (m, 2H).

Example II.2-II.20

| Example No. | Side chain structure | Example structure | Example name |
|---|---|---|---|
| II.2 | 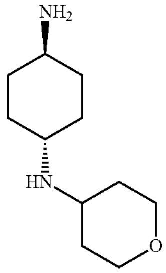 8a | 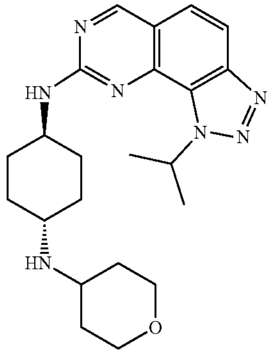 [SMILES: CC(C)n1nnc2ccc3cnc(N[C@H]4CC[C@H](NC5CCOCC5)CC4)nc3c21] | (1R,4R)-N$^1$-(1-isopropyl-1H-[1,2,3]triazolo[4,5-h]quinazolin-8-yl)-N$^4$-(tetrahydro-2H-pyran-4-yl)cyclohexane-1,4-diamine |

-continued

| Example No. | Side chain structure | Example structure | Example name |
|---|---|---|---|
| II.3 | 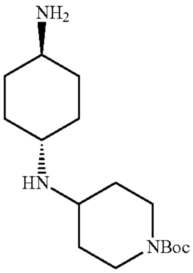 8b | 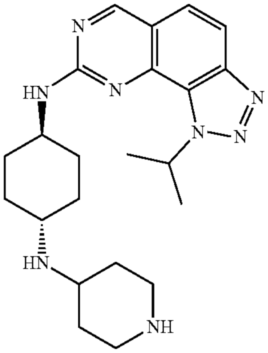 [SMILES: CC(C)n1nnc2ccc3cnc(N[C@H]4CC[C@H](NC5CCNCC5)CC4)nc3c21] | (1R,4R)-$N^1$-(1-isopropyl-1H-[1,2,3]triazolo[4,5-h]quinazolin-8-yl)-$N^4$-(piperidin-4-yl)cyclohexane-1,4-diamine |
| II.4 | 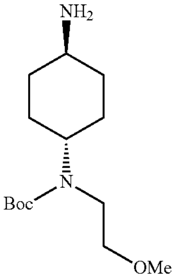 8g | 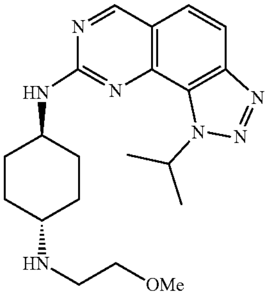 [SMILES: COCCN[C@H]1CC[C@H](Nc2ncc3ccc4nnn(C(C)C)c4c3n2)CC1] | (1R,4R)-$N^1$-(1-isopropyl-1H-[1,2,3]triazolo[4,5-h]quinazolin-8-yl)-$N^4$-(2-methoxyethyl)cyclohexane-1,4-diamine |
| II.5 | 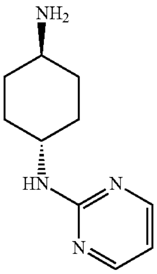 8c | 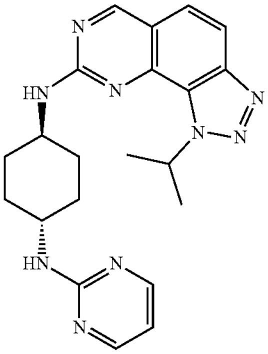 [SMILES: CC(C)n1nnc2ccc3cnc(N[C@H]4CC[C@H](Nc5ncccn5)CC4)nc3c21] | (1R,4R)-$N^1$-(1-isopropyl-1H-[1,2,3]triazolo[4,5-h]quinazolin-8-yl)-$N^4$-(pyrimidin-2-yl)cyclohexane-1,4-diamine |
| II.6 | 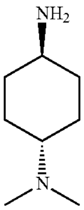 8h | 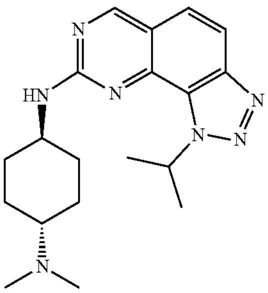 [SMILES: CC(C)n1nnc2ccc3cnc(N[C@H]4CC[C@H](N(C)C)CC4)nc3c21] | (1R,4R)-$N^1$-(1-isopropyl-1H-[1,2,3]triazolo[4,5-h]quinazolin-8-yl)-$N^4$,$N^4$-dimethylcyclohexane-1,4-diamine |

-continued
| Example No. | Side chain structure | Example structure | Example name |
|---|---|---|---|
| II.7 | 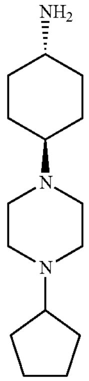 8i | 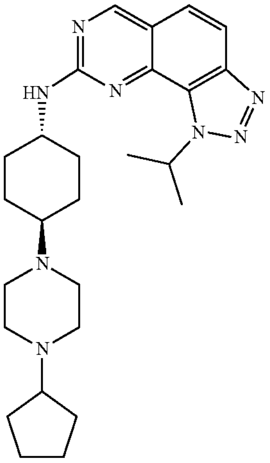 [SMILES: CC(C)n1nnc2ccc3cnc(N[C@H]4CC[C@H](N5CCN(C6CCCC6)CC5)CC4)nc3c21] | N-((1R,4R)-4-(4-cyclopentylpiperazin-1-yl)cyclohexyl)-1-isopropyl-1H-[1,2,3]triazolo[4,5-h]quinazolin-8-amine |
| II.8 | 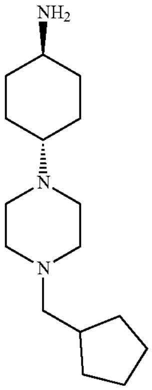 8j | 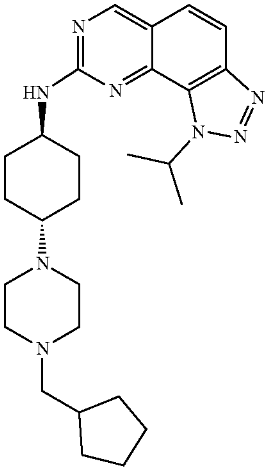 [SMILES: CC(C)n1nnc2ccc3cnc(N[C@H]4CC[C@H](N5CCN(CC6CCCC6)CC5)CC4)nc3c21] | N-((1R,4R)-4-(4-(cyclopentylmethyl)piperazin-1-yl)cyclohexyl)-1-isopropyl-1H-[1,2,3]triazolo[4,5-h]quinazolin-8-amine |
| II.9 | 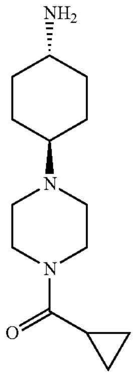 8k | 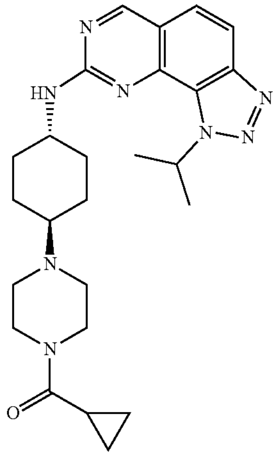 [SMILES: CC(C)n1nnc2ccc3cnc(N[C@H]4CC[C@H](N5CCN(C(=O)C6CC6)CC5)CC4)nc3c21] | Cyclopropyl(4-((1R,4R)-4-((1-isopropyl-1H-[1,2,3]triazolo[4,5-h]quinazolin-8-yl)amino)cyclohexyl)piperazin-1-yl)ketone |

-continued

| Example No. | Side chain structure | Example structure | Example name |
|---|---|---|---|
| II.10 | 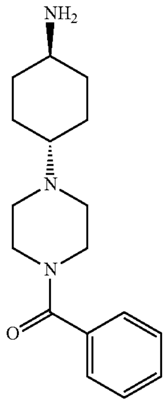 8l | 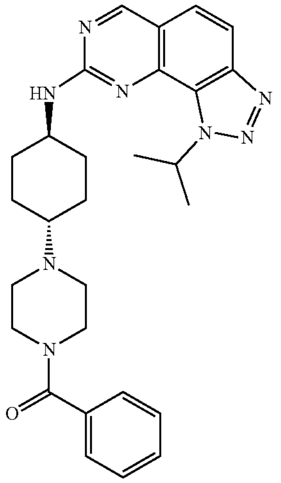 [SMILES: CC(C)n1nnc2ccc3cnc(N[C@H]4CC[C@H](N5CCN(C(=O)c6ccccc6)CC5)CC4)nc3c21] | (4-((1R,4R)-4-((1-isopropyl-1H-[1,2,3]triazolo[4,5-h] quinazolin-8-yl)amino)cyclohexyl)piperazin-1-yl)(phenyl) ketone |
| II.11 | 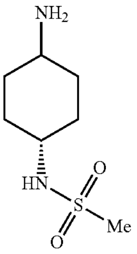 8m | 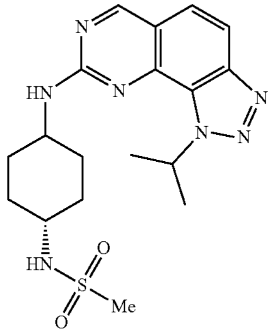 | N-(4-((1-isopropyl-1H-[1,2,3]triazolo[4,5-h]quinazolin-8-yl)amino)cyclohexyl)methanesulfonamide |
| II.12 | 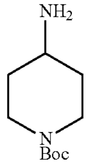 8d | 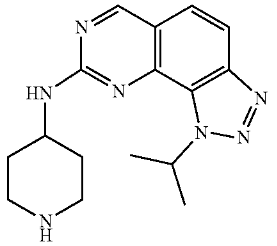 [SMILES: CC(C)n1nnc2ccc3cnc(NC4CCNCC4)nc3c21] | 1-isopropyl-N-(piperidin-4-yl)-1H-[1,2,3]triazolo[4,5-h] quinazolin-8-amine |
| II.13 | 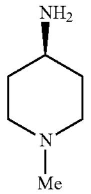 8n | 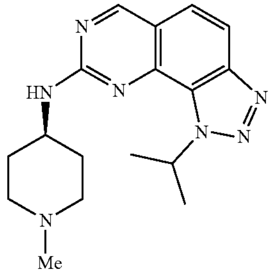 | 1-isopropyl-N-(1-methylpiperidin-4-yl)-1H-[1,2,3]triazolo [4,5-h]quinazolin-8-amine |

-continued

| Example No. | Side chain structure | Example structure | Example name |
| --- | --- | --- | --- |
| II.14 | 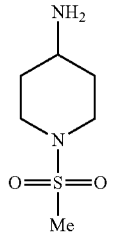 8e | 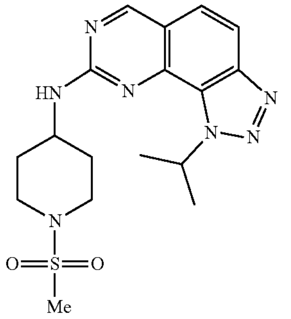 [SMILES: CC(C)n1nnc2ccc3cnc(NC4CCN(S(C)(=O)=O)CC4)nc3c21] | 1-isopropyl-N-(1-(methylsulfonyl)piperidin-4-yl)-1H-[1,2,3] triazolo[4,5-h]quinazolin-8-amine |
| II.15 | 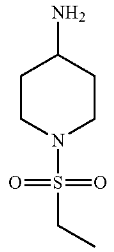 8o | 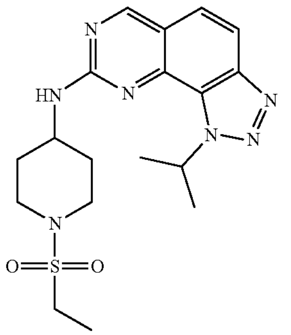 [SMILES: CCS(=O)(=O)N1CCC(Nc2ncc3ccc4nnn(C(C)C)c4c3n2)CC1] | N-(1-(ethylsulfonyl)piperidin-4-yl)-1-isopropyl-1H-[1,2,3] triazolo[4,5-h]quinazolin-8-amine |
| II.16 | 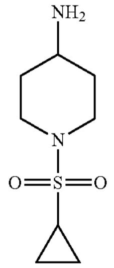 8p | 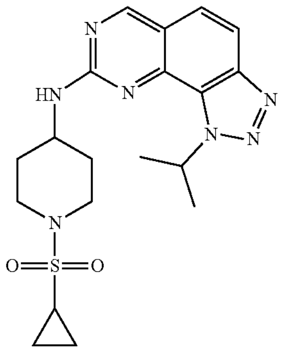 [SMILES: CC(C)n1nnc2ccc3cnc(NC4CCN(S(=O)(=O)C5CC5)CC4)nc3c21] | N-(1-(cyclopropylsulfonyl)piperidin-4-yl)-1-isopropyl-1H-[1,2,3]triazolo[4,5-h]quinazolin-8-amine |
| II.17 | 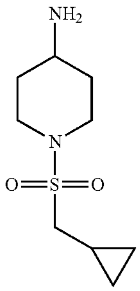 8q | 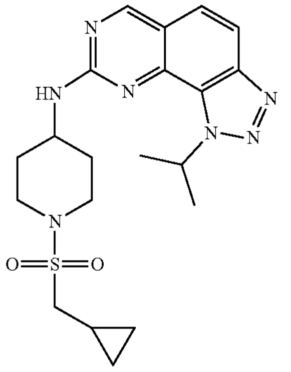 [SMILES: CC(C)n1nnc2ccc3cnc(NC4CCN(S(=O)(=O)CC5CC5)CC4)nc3c21] | N-(1-((cyclopropylmethyl)sulfonyl)piperidin-4-yl)-1-iso-propyl-1H-[1,2,3]triazolo[4,5-h]quinazolin-8-amine |

-continued

| Example No. | Side chain structure | Example structure | Example name |
|---|---|---|---|
| II.18 | 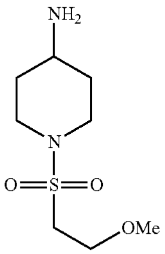 8r | 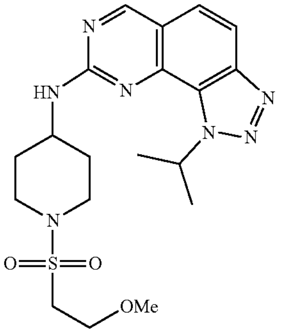 [SMILES: COCCS(=O)(=O)N1CCC(Nc2ncc3ccc4nnn(C(C)C)c4c3n2)CC1] | 1-isopropyl-N-(1-((2-methoxyethyl)sulfonyl)piperidin-4-yl)-1H-[1,2,3]triazolo[4,5-h]quinazolin-8-amine |
| II.19 | 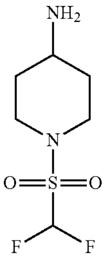 8s | 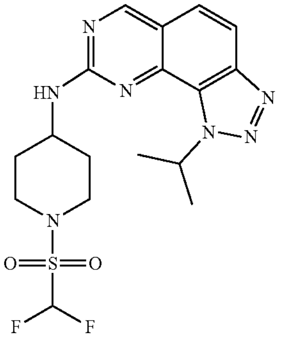 [SMILES: CC(C)n1nnc2ccc3cnc(NC4CCN(S(=O)(=O)C(F)F)CC4)nc3c21] | N-(1-((difluoromethyl)sulfonyl)piperidin-4-yl)-1-isopropyl-1H-[1,2,3]triazolo[4,5-h]quinazolin-8-amine |
| II.20 | 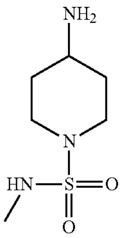 8t | 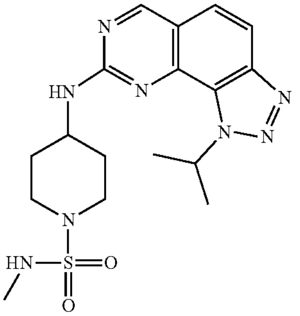 [SMILES: CNS(=O)(=O)N1CCC(Nc2ncc3ccc4nnn(C(C)C)c4c3n2)CC1] | 4-((1-isopropyl-1H-[1,2,3]triazolo[4,5-h]quinazolin-8-yl)amino)-N-methylpiperidin-1-sulfamide |

By referring to the synthesis method of 0.1 in Example I.1, compound II.2 (88.4 mg, 0.216 mmol, 89%) was prepared from 16a (60.0 mg, 0.243 mmol), hydrochloride of (1R,4R)—$N^1$-(tetrahydro-2H-pyran-4-yl)cyclohexane-1,4-diamine 8a (118.1 mg, 0.486 mmol) and potassium carbonate (134.1 mg, 0.972 mmol). $^1$H NMR (400 MHz, chloroform-d, ppm) δ 8.98 (s, 1H), 7.73 (d, J=8.8 Hz, 1H), 7.46 (d, J=8.8 Hz, 1H), 6.12 (p, J=6.7 Hz, 1H), 5.34 (s, 1H), 3.99 (ddd, J=11.9, 4.3, 2.1 Hz, 2H), 3.91 (s, 1H), 3.51-3.37 (m, 2H), 2.83 (tt, J=10.7, 4.0 Hz, 1H), 2.74 (dt, J=9.9, 5.6 Hz, 1H), 2.30 (d, J=10.2 Hz, 2H), 2.03 (dt, J=10.5, 3.2 Hz, 2H), 1.90-1.85 (m, 2H), 1.81 (d, J=6.7 Hz, 6H), 1.45-1.30 (m, 6H).

By referring to the synthesis method of I.2 in Example I.2, hydrochloride of compound II.3 (81.4 mg, 0.199 mmol, two-step yield 82%) was prepared from 16a (60.0 mg, 0.243 mmol) and 8b (144.4 mg, 0.486 mmol). LC-MS (ESI), $C_{22}H_{33}N_8[M+H]^+$: m/z=409.2.

By referring to the synthesis method of I.2 in Example I.2, hydrochloride of compound II.4 (80.0 mg, 0.190 mmol, two-step yield 78%) was prepared from 16a (60.0 mg, 0.243 mmol) and 8g (163.0 mg, 0.486 mmol). LC-MS (ESI), $C_{20}H_{30}N_7O$ $[M+H]^+$: m/z=384.3.

By referring to the synthesis method of I.1 in Example I.1, compound II.5 (74.6 mg, 0.185 mmol, 76%) was prepared from 16a (60.0 mg, 0.243 mmol) and hydrochloride of 8c (144.4 mg, 0.486 mmol). LC-MS (ESI), $C_{21}H_{26}N_9[M+H]^+$: m/z=404.2.

By referring to the synthesis method of I.1 in Example I.1, compound II.6 (71.0 mg, 0.200 mmol, 82%) was prepared from 16a (60.0 mg, 0.243 mmol) and trans-N,N-dimethyl-1,4-cyclohexandiamine 8h (69.0 mg, 0.486 mmol). $^1$H NMR (400 MHz, chloroform-d, ppm) δ 9.00 (s, 1H), 7.74 (d, J=8.8 Hz, 1H), 7.47 (d, J=8.8 Hz, 1H), 6.12 (p, J=6.7 Hz, 1H), 5.38 (s, 1H), 3.89 (s, 1H), 3.37 (s, 1H), 2.47 (s, 6H), 2.36 (d, J=11.8 Hz, 2H), 2.14 (d, J=11.8 Hz, 2H), 1.82 (d, J=6.7 Hz, 6H), 1.49 (q, J=13.8, 12.9 Hz, 2H), 1.41-1.34 (m, 2H).

By referring to the synthesis method of I.1 in Example I.1, compound II.7 (87.0 mg, 0.190 mmol, 78%) was prepared from 16a (60.0 mg, 0.243 mmol) and (1R,4R)-4-(4-cyclopentylpiperazin-1-yl)cyclohexan-1-amine 8i (122.0 mg, 0.486 mmol). 1H NMR (400 MHz, chloroform-d, ppm) δ

8.99 (s, 1H), 7.74 (d, J=9.0 Hz, 1H), 7.49-7.46 (m, 1H), 6.16-6.06 (m, 1H), 5.78 (s, 1H), 4.24 (s, 1H), 3.10 (dd, J=17.8, 10.4 Hz, 8H), 2.61 (s, 1H), 2.09 (d, J=9.1 Hz, 2H), 2.02 (d, J=13.1 Hz, 2H), 1.84 (s, 4H), 1.81 (d, J=6.7 Hz, 7H), 1.79-1.71 (m, 4H), 1.52-1.40 (m, 4H).

By referring to the synthesis method of I.1 in Example I.1, compound II.8 (87.0 mg, 0.180 mmol, 75%) was prepared from 16a (60.0 mg, 0.243 mmol) and (1R,4R)-4-(4-(cyclopentylmethyl)piperazin-1-yl)cyclohexan-1-amine 8j (129.0 mg, 0.486 mmol). 1H NMR (400 MHz, chloroform-d, ppm) δ 9.01 (s, 1H), 7.75 (d, J=8.8 Hz, 1H), 7.48 (d, J=8.8 Hz, 1H), 6.15-6.07 (m, 1H), 5.94 (s, 1H), 4.29 (d, J=7.1 Hz, 1H), 2.97 (d, J=117.3 Hz, 8H), 2.64 (s, 2H), 2.19 (d, J=12.0 Hz, 3H), 1.97 (s, 2H), 1.81 (d, J=6.7 Hz, 12H), 1.65-1.60 (m, 2H), 1.58-1.52 (m, 2H), 1.27-1.21 (m, 2H).

By referring to the synthesis method of I.1 in Example I.1, compound II.9 (88.0 mg, 0.19 mmol, 79%) was prepared from 16a (60.0 mg, 0.243 mmol) and (4-((1R,4R)-4-aminocyclohexyl)piperazin-1-yl)(cyclopropyl)ketone 8k (122.0 mg, 0.486 mmol). LC-MS (ESI), $C_{25}H_{35}N_8O$ $[M+H]^+$: m/z=463.3.

By referring to the synthesis method of I.1 in Example I.1, compound II.10 (100.0 mg, 0.200 mmol, 82%) was prepared from 16a (60.0 mg, 0.243 mmol) and (4-((1R,4R)-4-aminocyclohexyl)piperazin-1-yl)(phenyl)ketone 8l (139.0 mg, 0.486 mmol). LC-MS (ESI), $C_{28}H_{35}N_8O$ $[M+H]^+$: m/z=499.3.

By referring to the synthesis method of I.1 in Example I.1, compound II.11 (80.0 mg, 0.200 mmol, 83%) was prepared from 16a (60.0 mg, 0.243 mmol) and N-(4-aminocyclohexyl)methanesulfonamide 8m (93.0 mg, 0.486 mmol). LC-MS (ESI), $C_{18}H_{26}N_7O_2S$ $[M+H]^+$: m/z=404.3.

By referring to the synthesis method of I.2a in Example I.2, compound II.12a (85.0 mg, 0.210 mmol, 85%) was prepared from 16a (60.0 mg, 0.243 mmol) and 8d (97.0 mg, 0.486 mmol). $^1$H NMR (400 MHz, chloroform-d, ppm) δ 9.00 (d, J=1.2 Hz, 1H), 7.74 (dd, J=8.9, 1.4 Hz, 1H), 7.48 (dd, J=8.8, 1.3 Hz, 1H), 6.10 (hept, J=6.7 Hz, 1H), 5.48 (s, 1H), 4.15-4.06 (m, 3H), 3.00 (t, J=12.5 Hz, 2H), 2.15 (dd, J=12.8, 3.8 Hz, 2H), 1.81 (d, J=6.7 Hz, 6H), 1.55 (td, J=11.9, 4.0 Hz, 2H), 1.48 (d, J=1.2 Hz, 9H).

By referring to the synthesis method of I.2 in Example I.2, compound II.12 (68.0 mg, 0.195 mmol, 93%) was prepared from II.12a (85.0 mg, 0.210 mmol). $^1$H NMR (400 MHz, dimethyl sulfoxide-$d_6$, ppm) δ 9.27 (s, 1H), 9.24 (s, 1H), 8.96 (s, 1H), 7.69 (q, J=8.8 Hz, 2H), 6.05 (s, 1H), 4.12 (s, 1H), 3.42-3.25 (m, 2H), 3.16-3.00 (m, 2H), 2.24-2.09 (m, 2H), 1.84 (ddd, J=14.1, 8.9, 3.6 Hz, 2H), 1.73 (d, J=6.7 Hz, 6H).

By referring to the synthesis method of I.1 in Example I.1, compound II.13 (63 mg, 0.19 mmol, 80%) was prepared from 16a (60.0 mg, 0.243 mmol) and 4-amino-1-methylpiperidine 8n (55.0 mg, 0.486 mmol). LC-MS (ESI), $C_{17}H_{24}N_7$$[M+H]^+$: m/z=326.3.

By referring to the synthesis method of I.1 in Example I.1, compound II.14 (86.0 mg, 0.221 mmol, 91%) was prepared from 16a (60.0 mg, 0.243 mmol) and 8e (86.6 mg, 0.486 mmol). $^1$H NMR (400 MHz, chloroform-d, ppm) δ 9.03 (s, 1H), 7.77 (d, J=8.8 Hz, 1H), 7.49 (d, J=8.8 Hz, 1H), 6.09 (p, J=6.7 Hz, 1H), 5.48 (s, 1H), 4.09 (s, 1H), 3.87-3.75 (m, 2H), 3.07-2.94 (m, 2H), 2.86 (s, 3H), 2.35-2.22 (m, 2H), 1.82 (d, J=6.7 Hz, 8H).

By referring to the synthesis method of I.1 in Example I.1, compound II.15 (73.0 mg, 0.18 mmol, 75%) was prepared from 16a (60.0 mg, 0.243 mmol) and 1-(ethylsulfonyl)piperidin-4-amine 8o (93.0 mg, 0.486 mmol). $^1$H NMR (400 MHz, chloroform-d, ppm) δ 9.03 (s, 1H), 7.78 (d, J=8.8 Hz, 1H), 7.50 (d, J=8.8 Hz, 1H), 6.10 (p, J=6.7 Hz, 1H), 5.53 (s, 1H), 4.16-4.07 (m, 1H), 3.84 (d, J=12.7 Hz, 2H), 3.10 (t, J=10.7 Hz, 2H), 3.03 (q, J=7.4 Hz, 2H), 2.31-2.23 (m, 2H), 1.83 (d, J=6.7 Hz, 6H), 1.77 (d, J=10.4 Hz, 2H), 1.41 (t, J=7.4 Hz, 3H).

By referring to the synthesis method of I.1 in Example I.1, compound II.16 (79.0 mg, 0.190 mmol, 78%) was prepared from 16a (60.0 mg, 0.243 mmol) and 1-(cyclopropylsulfonyl)piperidin-4-amine 8p (99.0 mg, 0.486 mmol). 1H NMR (400 MHz, chloroform-d, ppm) δ 9.03 (s, 1H), 7.77 (d, J=8.8 Hz, 1H), 7.50 (d, J=8.8 Hz, 1H), 6.10 (p, J=6.7 Hz, 1H), 5.51 (s, 1H), 4.16-4.05 (m, 1H), 3.83 (d, J=12.3 Hz, 2H), 3.12 (t, J=10.5 Hz, 2H), 2.37-2.30 (m, 1H), 2.27 (dd, J=13.2, 3.3 Hz, 2H), 1.82 (d, J=6.7 Hz, 8H), 1.22 (dd, J=4.8, 2.1 Hz, 2H), 1.06-1.01 (m, 2H).

By referring to the synthesis method of I.1 in Example I.1, compound II.17 (79.0 mg, 0.180 mmol, 76%) was prepared from 16a (60.0 mg, 0.243 mmol) and 1-((cyclopropylmethyl)sulfonyl)piperidin-4-amine 8q (106 mg, 0.486 mmol). $^1$H NMR (400 MHz, chloroform-d, ppm) δ 9.04 (s, 1H), 7.78 (d, J=8.8 Hz, 1H), 7.50 (d, J=8.8 Hz, 1H), 6.10 (p, J=6.7 Hz, 1H), 5.45 (s, 1H), 4.11 (s, 1H), 3.88 (d, J=12.7 Hz, 2H), 3.11 (t, J=11.6 Hz, 2H), 2.93 (d, J=7.1 Hz, 2H), 2.30-2.23 (m, 2H), 1.83 (d, J=6.7 Hz, 6H), 1.77 (d, J=10.6 Hz, 2H), 1.17 (tt, J=7.7, 3.9 Hz, 1H), 0.75 (q, J=5.6, 5.0 Hz, 2H), 0.41 (q, J=5.0 Hz, 2H).

By referring to the synthesis method of I.1 in Example I.1, compound II.18 (87 mg, 0.20 mmol, 83%) was prepared from 16a (60.0 mg, 0.243 mmol) and 1-((2-methoxyethyl)sulfonyl)piperidin-4-amine 8r (96.0 mg, 0.486 mmol). LC-MS (ESI), $C_{19}H_{27}N_7NaO_3S$ $[M+Na]^+$: m/z=456.2.

By referring to the synthesis method of I.1 in Example I.1, compound II.19 (84.0 mg, 0.197 mmol, 81%) was prepared from 16a (60.0 mg, 0.243 mmol) and 1-((difluoromethyl)sulfonyl)piperidin-4-amine 8s (104.0 mg, 0.486 mmol). $^1$H NMR (400 MHz, chloroform-d, ppm) δ 9.04 (s, 1H), 7.79 (d, J=8.8 Hz, 1H), 7.51 (d, J=8.8 Hz, 1H), 6.40-6.05 (m, 2H), 5.47 (s, 1H), 4.23-4.13 (m, 1H), 4.03 (d, J=13.5 Hz, 2H), 3.39-3.30 (m, 2H), 2.29 (dd, J=13.2, 3.2 Hz, 2H), 1.83 (d, J=6.7 Hz, 6H), 1.80-1.71 (m, 2H).

By referring to the synthesis method of I.1 in Example I.1, compound II.20 (81.0 mg, 0.199 mmol, 82%) was prepared from 16a (60.0 mg, 0.243 mmol) and 4-amino-N-methylpiperidin-1-sulfamide 8t (94.0 mg, 0.486 mmol). LC-MS (ESI), $C_{17}H_{24}N_8NaO_2S$ $[M+Na]^+$: m/z=427.2.

Example II.21 and Example II.22

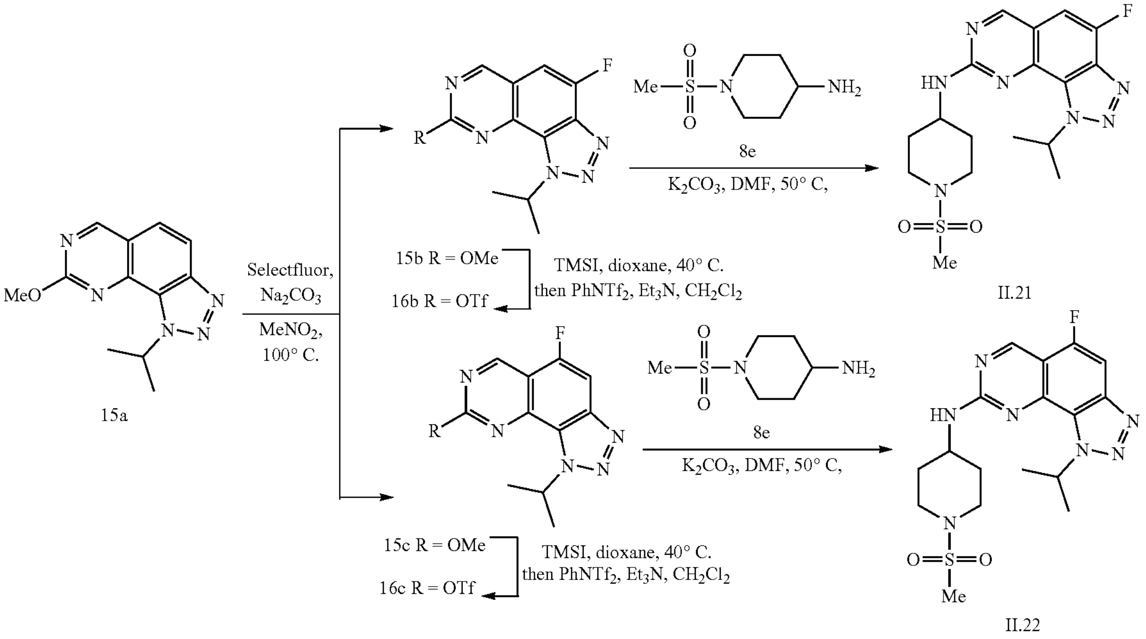

4-fluoro-1-isopropyl-N-(1-(methylsulfonyl)piperidin-4-yl)-1H-[1,2,3]triazolo[4,5-h]quinazolin-8-amine (II.21)

1): 4-fluoro-1-isopropyl-8-methoxy-1H-[1,2,3]triazolo[4,5-h]quinazoline (15b) and 5-fluoro-1-isopropyl-8-methoxy-1H-[1,2,3]triazolo[4,5-h]quinazoline (15c)

By referring to the synthesis method of 6b in Example I.6, compounds 15b (48.0 mg, 0.185 mmol, yield 15%) and 15c (64.0 mg, 0.245 mmol, yield 20%) were prepared from 15a (300.0 mg, 1.230 mmol).

15b: $^1$H NMR (400 MHz, chloroform-d, ppm) δ 9.25 (s, 1H), 7.31 (d, J=9.1 Hz, 1H), 6.15 (p, J=6.8 Hz, 1H), 4.19 (s, 3H), 1.87 (d, J=6.7 Hz, 6H).

15c: $^1$H NMR (400 MHz, chloroform-d, ppm) δ 9.54 (s, 1H), 7.60 (d, J=9.2 Hz, 1H), 6.12-6.04 (m, 1H), 4.21 (d, J=4.1 Hz, 3H), 1.85 (dd, J=6.8, 2.3 Hz, 6H).

2): 4-fluoro-1-isopropyl-1H-[1,2,3]triazolo[4,5-h]quinazolin-8-yl trifluoromethanesulfonate (16b)

Trimethyliodosilane (53.0 μL, 0.370 mmol) was slowly added dropwise into a solution of 15b (48.0 mg, 0.185 mmol) in 1,4-dioxane (2 mL) in an ice-water bath. After the addition was completed, the mixture was heated to 40° C. and reacted for 4 hours. The reaction solution was cooled to 0° C., and saturated aqueous sodium bicarbonate solution was slowly added dropwise into the reaction solution under vigorous stirring until the pH was adjusted to about 8. Saturated sodium thiosulfate aqueous solution (3 mL) was added, and the mixture was extracted with ethyl acetate (10 mL×3). The organic phases were combined, washed with saturated saline solution (15 mL×1), dried (anhydrous sodium sulfate), and filtered. The filtrate was concentrated under reduced pressure. The crude product can be directly used in the next reaction without silica gel column chromatography purification.

Triethylamine (0.1 mL, 0.74 mmol) and N-phenylbis(trifluoromethylsulfonyl)imine (75.0 μL, 0.37 mmol) were sequentially added dropwise to the suspension of the crude product (45 mg) obtained in the previous step in dichloromethane (2 mL) in an ice bath. After the addition was completed, the reaction solution was raised to room temperature and further reacted for 5 hours. The reaction solution was diluted with dichloromethane (10 mL) and saturated sodium bicarbonate aqueous solution (10 mL). The aqueous phase was separated, and extracted with dichloromethane (10 mL×2). The organic phases were combined, washed with saturated saline solution (15 mL), dried (anhydrous sodium sulfate), and filtered. The filtrate was concentrated under reduced pressure. The resulting residue was purified by flash silica gel column chromatography (petroleum ether/ethyl acetate=12:1) to give the titled compound 16b (52.0 mg, 0.136 mmol, yield 75%) as a pale-yellow solid. $^1$H NMR (400 MHz, chloroform-d, ppm) δ 9.47 (s, 1H), 7.49 (d, J=8.8 Hz, 1H), 6.08-6.00 (m, 1H), 1.87 (d, J=6.7 Hz, 6H).

3): 4-fluoro-1-isopropyl-N-(1-(methylsulfonyl)piperidin-4-yl)-1H-[1,2,3]triazolo[4,5-h]quinazolin-8-amine (II.21)

By referring to the synthesis method of I.1 in Example I.1, compound II.21 (32.0 mg, 0.078 mmol, yield 60%) was prepared from 16b (50.0 mg, 0.130 mmol) and 8e (46.0 mg, 0.260 mmol). $^1$H NMR (400 MHz, chloroform-d, ppm) δ 8.96 (s, 1H), 7.13 (d, J=9.3 Hz, 1H), 6.10 (p, J=6.7 Hz, 1H), 5.11 (d, J=7.5 Hz, 1H), 4.11-4.01 (m, 1H), 3.79 (d, J=12.2 Hz, 2H), 3.09-2.97 (m, 2H), 2.86 (s, 3H), 2.26 (dt, J=12.2, 3.8 Hz, 2H), 1.83 (d, J=6.7 Hz, 8H).

5-fluoro-1-isopropyl-N-(1-(methylsulfonyl)piperidin-4-yl)-1H-[1,2,3]triazolo[4,5-h]quinazolin-8-amine (I.22)

1): 5-fluoro-1-isopropyl-1H-[1,2,3]triazolo[4,5-h]quinazolin-8-yl trifluoromethanesulfonate (16c)

By referring to the synthesis method of 16b in Example II.21, compound 16c (66.0 mg, 0.173 mmol, yield 70%) was prepared from 15c (60.0 mg, 0.247 mmol). 1H NMR (400 MHz, chloroform-d, ppm) δ 9.74 (s, 1H), 7.90 (d, J=8.8 Hz, 1H), 5.97 (h, J=6.7 Hz, 1H), 1.85 (d, J=6.7 Hz, 6H).

2): 5-fluoro-1-isopropyl-N-(1-(methylsulfonyl)piperidin-4-yl)-1H-[1,2,3]triazolo[4,5-h]quinazolin-8-amine (I.22)

By referring to the synthesis method of I.1 in Example I.1, compound II.22 (38.0 mg, 0.095 mmol, yield 63%) was prepared from 16c (60.0 mg, 0.158 mmol) and 8e (56.0 mg, 0.316 mmol). $^1$H NMR (400 MHz, chloroform-d, ppm) δ 9.25 (s, 1H), 7.37 (d, J=9.4 Hz, 1H), 6.08-5.96 (m, 1H), 5.82-5.63 (m, 1H), 4.10 (ddd, J=17.5, 13.5, 6.9 Hz, 1H), 3.81 (s, 2H), 3.02 (s, 2H), 2.86 (s, 3H), 2.28 (dd, J=13.2, 3.8 Hz, 2H), 1.81 (d, J=6.7 Hz, 8H).

Example II.23

4-chloro-1-isopropyl-N-(1-(methylsulfonyl)piperidin-4-yl)-1H-[1,2,3]triazolo[4,5-h]quinazolin-8-amine (II.23)

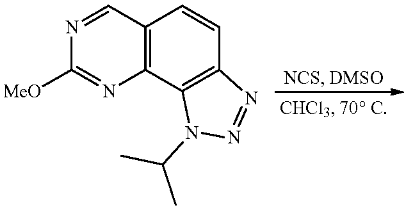

15a

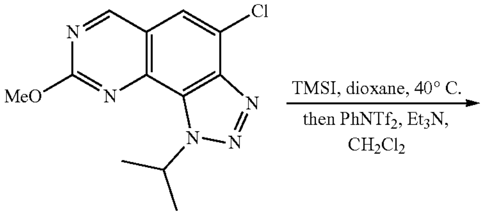

15d

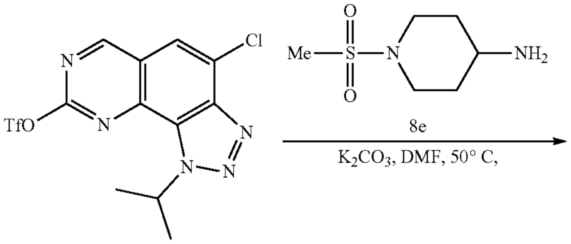

16d

-continued

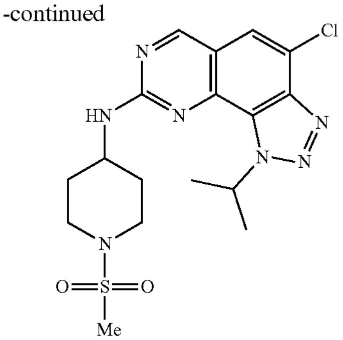

II.23

1): 4-chloro-1-isopropyl-8-methoxy-1H-[1,2,3]triazolo[4,5-h]quinazoline (15d)

By referring to the synthesis method of 6c in Example I.7, compound 15d (68.0 mg, 0.250 mmol, yield 30%) was prepared from 15a (200.0 mg, 0.820 mmol). $^1$H NMR (400 MHz, chloroform-d, ppm) δ 9.25 (s, 1H), 7.70 (s, 1H), 6.16-6.11 (m, 1H), 4.20 (s, 3H), 1.86 (d, J=6.7 Hz, 6H).

2): 4-chloro-1-isopropyl-1H-[1,2,3]triazolo[4,5-h]quinazolin-8-yl trifluoromethanesulfonate (16d)

By referring to the synthesis method of 16b in Example II.21, compound 16d (68.0 mg, 0.170 mmol, yield 70%) was prepared from 15d (68.0 mg, 0.250 mmol). $^1$H NMR (400 MHz, chloroform-d, ppm) δ 9.46 (s, 1H), 7.88 (s, 1H), 6.07-6.00 (m, 1H), 1.86 (d, J=6.7 Hz, 6H).

3): 4-chloro-1-isopropyl-N-(1-(methylsulfonyl)piperidin-4-yl)-1H-[1,2,3]triazolo[4,5-h]quinazolin-8-amine (II.23)

By referring to the synthesis method of I.1 in Example I.1, compound II.23 (46.0 mg, 0.110 mmol, yield 73%) was prepared from 16d (60.0 mg, 0.150 mmol) and 8e (53.0 mg, 0.300 mmol). $^1$H NMR (400 MHz, chloroform-d, ppm) δ 8.97 (s, 1H), 7.52 (s, 1H), 6.08 (p, J=6.7 Hz, 1H), 5.47 (s, 1H), 4.08 (s, 1H), 3.82 (d, J=12.1 Hz, 2H), 3.00 (t, J=11.6 Hz, 2H), 2.86 (s, 3H), 2.28 (dd, J=13.1, 3.8 Hz, 2H), 1.82 (d, J=6.7 Hz, 8H).

Example II.24

4-bromo-1-isopropyl-N-(1-(methylsulfonyl)piperidin-4-yl)-1H-[1,2,3]triazolo[4,5-h]quinazolin-8-amine (II.24)

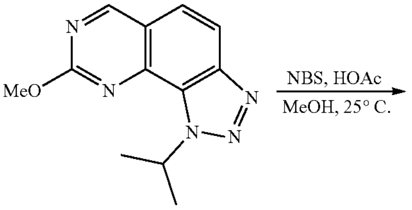

15a

-continued

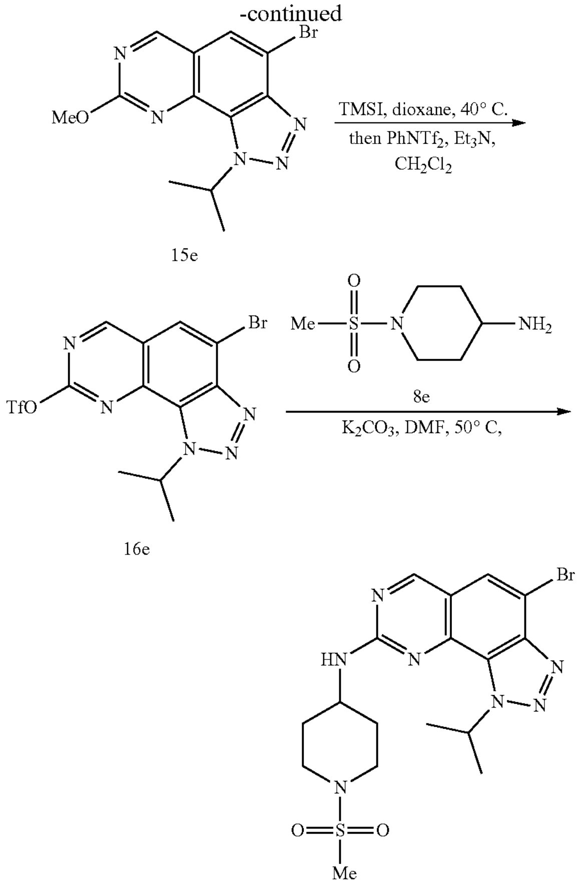

15e

16e

II.24

1): 4-bromo-1-isopropyl-8-methoxy-1H-[1,2,3]triazolo[4,5-h]quinazoline (15e)

By referring to the synthesis method of 6d in Example I.8, compound 15e (336.0 mg, 1.050 mmol, yield 85%) was prepared from 15a (300.0 mg, 1.230 mmol). $^1$H NMR (400 MHz, chloroform-d, ppm) δ 9.25 (s, 1H), 7.89 (s, 1H), 6.13 (h, J=6.7 Hz, 1H), 4.20 (s, 3H), 1.86 (d, J=6.7 Hz, 6H).

2): 4-bromo-1-isopropyl-1H-[1,2,3]triazolo[4,5-h]quinazolin-8-yl trifluoromethanesulfonate (16e)

By referring to the synthesis method of 16b in Example II.21, compound 16e (302.0 mg, 0.690 mmol, yield 75%) was prepared from 15e (300.0 mg, 0.930 mmol). $^1$H NMR (400 MHz, chloroform-d, ppm) δ 9.46 (s, 1H), 8.08 (s, 1H), 6.03 (h, J=6.7 Hz, 1H), 1.86 (d, J=6.7 Hz, 6H).

3): 4-bromo-1-isopropyl-N-(1-(methylsulfonyl)piperidin-4-yl)-1H-[1,2,3]triazolo[4,5-h]quinazolin-8-amine (II.24)

By referring to the synthesis method of I.1 in Example I.1, compound II.24 (154.0 mg, 0.330 mmol, yield 78%) was prepared from 16e (184.0 mg, 0.420 mmol) and 8e (150.0 mg, 0.840 mmol). $^1$H NMR (400 MHz, chloroform-d, ppm) δ 8.96 (s, 1H), 7.70 (s, 1H), 6.07 (p, J=6.8 Hz, 1H), 5.56 (s, 1H), 4.08 (s, 1H), 3.81 (d, J=11.5 Hz, 2H), 3.11-2.92 (m, 2H), 2.86 (s, 3H), 2.31-2.20 (m, 2H), 1.82 (d, J=6.7 Hz, 8H).

Examples II.25-II.31

| Example No. | Example structure | Example name |
|---|---|---|
| II.25 | 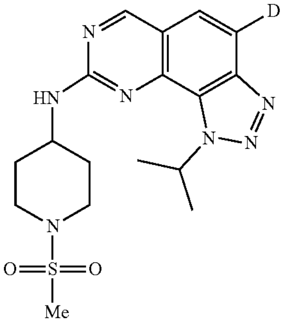 [SMILES: [2H]c1cc2cnc(NC3CCN(S(C)(=O)=O)CC3)nc2c2c1nnn2C(C)C] | 1-isopropyl-N-(1-(methylsulfonyl)piperidin-4-yl)-1H-[1,2,3]triazolo[4,5-h]quinazolin-4-d-8-amine |
| II.26 | 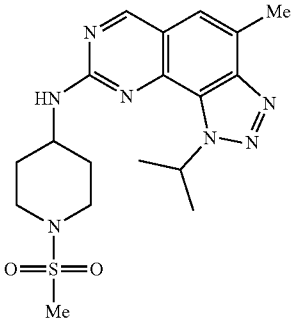 [SMILES: Cc1cc2cnc(NC3CCN(S(C)(=O)=O)CC3)nc2c2c1nnn2C(C)C] | 1-isopropyl-4-methyl-N-(1-(methylsulfonyl)piperidin-4-yl)-1H-[1,2,3]triazolo[4,5-h]quinazolin-8-amine |

-continued

| Example No. | Example structure | Example name |
|---|---|---|
| II.27 | 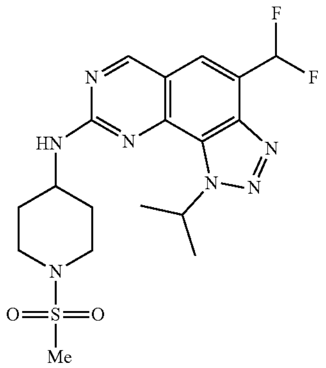 [SMILES: CC(C)n1nnc2c(C(F)F)cc3cnc(NC4CCN(S(C)(=O)=O)CC4)nc3c21] | 4-(difluoromethyl)-1-isopropyl-N-(1-(methylsulfonyl)piperidin-4-yl)-1H-[1,2,3]triazolo[4,5-h]quinazolin-8-amine |
| II.28 | 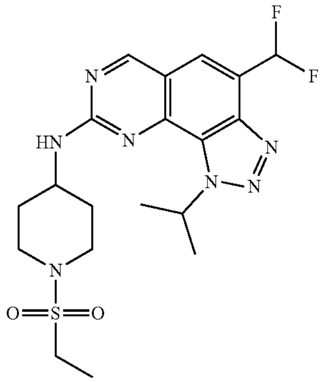 [SMILES: CCS(=O)(=O)N1CCC(Nc2ncc3cc(C(F)F)c4nnn(C(C)C)c4c3n2)CC1] | 4-(difluoromethyl)-N-(1-(ethylsulfonyl)piperidin-4-yl)-1-isopropyl-1H-[1,2,3]triazolo[4,5-h]quinazolin-8-amine |
| II.29 | 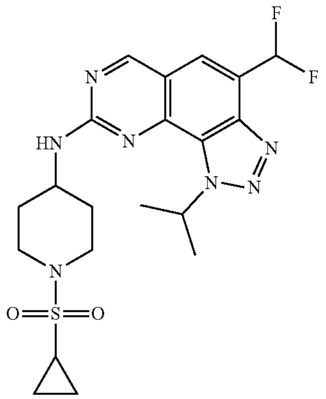 [SMILES: CC(C)n1nnc2c(C(F)F)cc3cnc(NC4CCN(S(=O)(=O)C5CC5)CC4)nc3c21] | N-(1-(cyclopropylsulfonyl)piperidin-4-yl)-4-(difluoromethyl)-1-isopropyl-1H-[1,2,3]triazolo[4,5-h]quinazolin-8-amine |
| II.30 | 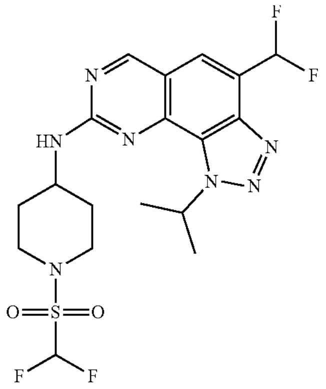 [SMILES: CC(C)n1nnc2c(C(F)F)cc3cnc(NC4CCN(S(=O)(=O)C(F)F)CC4)nc3c21] | 4-(difluoromethyl)-N-(1-((difluoromethyl)sulfonyl)piperidin-4-yl)-1-isopropyl-1H-[1,2,3]triazolo[4,5-h]quinazolin-8-amine |

-continued

| Example No. | Example structure | Example name |
| --- | --- | --- |
| II.31 | 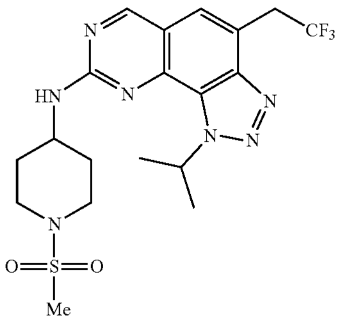 [SMILES: CC(C)n1nnc2c(CC(F)(F)F)cc3cnc(NC4CCN(S(C)(=O)=O)CC4)nc3c21] | 1-isopropyl-N-(1-(methylsulfonyl)piperidin-4-yl)-4-(2,2,2-trifluoroethyl)-1H-[1,2,3]triazolo[4,5-h]quinazolin-8-amine |

By referring to the synthesis method of I.11 in Example I.11, compound II.25 (39.0 mg, 0.100 mmol, yield 75%) was prepared from II.24 (60.0 mg, 0.130 mmol). $^1$H NMR (400 MHz, chloroform-d, ppm) δ 9.03 (s, 1H), 7.50 (s, 1H), 6.11 (q, J=6.7 Hz, 1H), 5.45 (s, 1H), 4.10 (d, J=6.8 Hz, 1H), 3.81 (d, J=12.1 Hz, 2H), 3.01 (t, J=11.2 Hz, 2H), 2.86 (s, 3H), 2.29 (dd, J=13.5, 3.8 Hz, 2H), 1.83 (d, J=6.7 Hz, 8H).

By referring to the synthesis method of I.12 in Example I.12, compound II.26 (41.0 mg, 0.100 mmol, yield 78%) was prepared from II.24 (60.0 mg, 0.130 mmol). $^1$H NMR (400 MHz, chloroform-d, ppm) δ 8.96 (s, 1H), 7.24 (s, 1H), 6.14-6.04 (m, 1H), 5.45 (s, 1H), 4.11-4.03 (m, 1H), 3.79 (dd, J=11.0, 6.2 Hz, 2H), 3.06-2.97 (m, 2H), 2.86 (s, 3H), 2.78 (d, J=1.2 Hz, 3H), 2.29 (dt, J=13.4, 3.8 Hz, 2H), 1.87-1.76 (m, 8H).

By referring to the synthesis method of I.14 in Example I.14, compound II.27 (49.0 mg, 0.110 mmol, yield 73%) was prepared from II.14 (60.0 mg, 0.150 mmol). $^1$H NMR (400 MHz, chloroform-d, ppm) δ 9.08 (s, 1H), 7.77 (d, J=1.8 Hz, 1H), 7.46 (d, J=55.2 Hz, 1H), 6.17-6.03 (m, 1H), 5.63 (s, 1H), 4.17-4.03 (m, 1H), 3.89-3.73 (m, 2H), 3.02 (d, J=12.2 Hz, 2H), 2.86 (s, 3H), 2.28 (dd, J=13.1, 3.8 Hz, 2H), 1.82 (d, J=6.7 Hz, 8H).

By referring to the synthesis method of I.14 in Example I.14, compound II.28 (50.0 mg, 0.110 mmol, yield 75%) was prepared from II.15 (60.0 mg, 0.150 mmol). $^1$H NMR (400 MHz, chloroform-d, ppm) δ 9.08 (s, 1H), 7.77 (d, J=1.9 Hz, 1H), 7.46 (d, J=55.2 Hz, 1H), 6.08 (d, J=7.5 Hz, 1H), 5.65 (s, 1H), 4.12 (s, 1H), 3.85 (d, J=12.5 Hz, 2H), 3.19-2.94 (m, 4H), 2.26 (dd, J=12.9, 4.0 Hz, 2H), 1.82 (d, J=6.7 Hz, 8H), 1.41 (t, J=7.4 Hz, 3H).

By referring to the synthesis method of I.14 in Example I.14, compound II.29 (48.0 mg, 0.102 mmol, yield 71%) was prepared from II.16 (60.0 mg, 0.144 mmol). $^1$H NMR (400 MHz, chloroform-d, ppm) δ 9.08 (s, 1H), 7.77 (d, J=1.8 Hz, 1H), 7.46 (d, J=55.3 Hz, 1H), 6.10 (q, J=6.9 Hz, 1H), 5.66 (s, 1H), 4.11 (s, 1H), 3.84 (q, J=6.6, 5.9 Hz, 2H), 3.11 (t, J=11.5 Hz, 2H), 2.37-2.21 (m, 3H), 1.82 (d, J=6.8 Hz, 8H), 1.21 (td, J=5.1, 1.7 Hz, 2H), 1.06-0.96 (m, 2H).

By referring to the synthesis method of I.14 in Example I.14, compound II.30 (28.0 mg, 0.058 mmol, yield 65%) was prepared from II.19 (40.0 mg, 0.090 mmol). $^1$H NMR (400 MHz, chloroform-d, ppm) δ 9.09 (s, 1H), 7.78 (d, J=1.9 Hz, 1H), 7.46 (d, J=55.3 Hz, 1H), 6.32 (d, J=53.9 Hz, 1H), 6.12-6.00 (m, 1H), 5.67 (s, 1H), 4.20 (d, J=17.4 Hz, 1H), 4.03 (dt, J=13.8, 4.1 Hz, 2H), 3.34 (ddd, J=13.7, 10.9, 2.8 Hz, 2H), 2.28 (dd, J=13.2, 3.8 Hz, 2H), 1.82 (d, J=6.8 Hz, 8H).

By referring to the synthesis method of I.14 in Example I.14, compound II.31 (13.0 mg, 0.030 mmol, yield 30%) was prepared from II.14 (40.0 mg, 0.090 mmol) and Zinc trifluoroethanesulfinate[3] (60.0 mg, 0.180 mmol). LC-MS (ESI), $C_{19}H_{25}F_3N_7O_2S$ $[M+H]^+$: m/z=472.2.

[3]The zinc salt reagent was also prepared with reference to document [2].

Example II.32 and Example II.33

(1R,2R)-1-methyl-2-(8-((1-(methylsulfonyl)piperidin-4-yl)amino)-1H-[1,2,3]triazolo[4,5-h]quinazolin-1-yl)cyclopentan-1-ol (II.32)

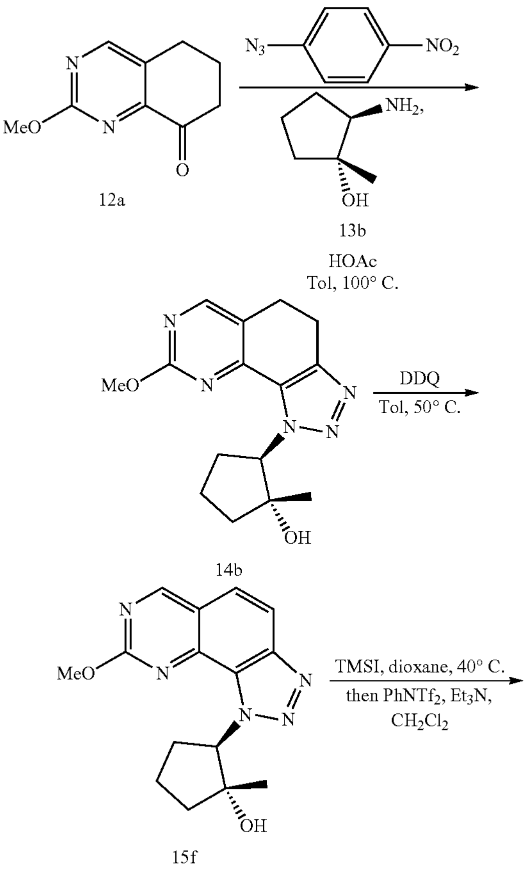

12a 13b 14b 15f

-continued

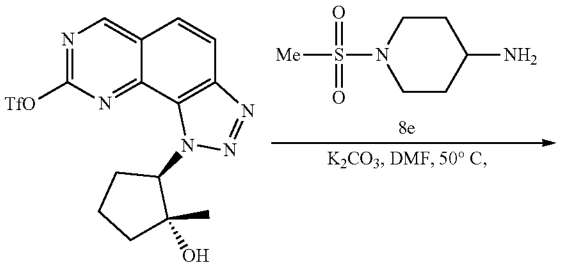

16f

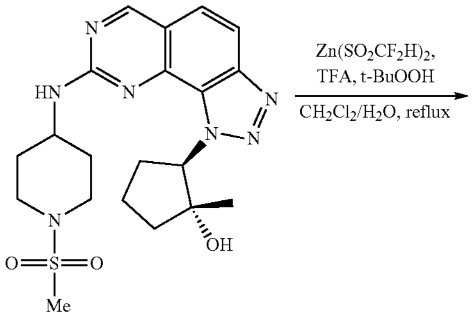

II.32

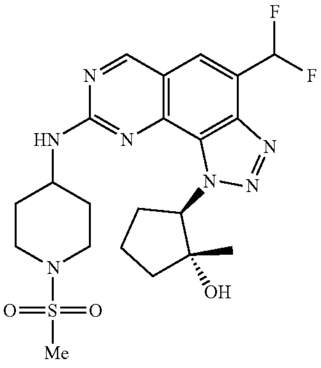

II.33

1): (1R,2R)-2-(8-methoxy-4,5-dihydro-1H-[1,2,3]triazolo[4,5-h]quinazolin-1-yl)-1-methylcyclopentan-1-ol (14b)

By referring to the synthesis method of 14a in Example II.1, compound 14b (100.0 mg, 0.330 mmol, yield 75%) was prepared from 12a (79.0 mg, 0.440 mmol) and (1R,2R)-2-amino-1-methylcyclopentan-1-ol 13b (101.0 mg, 0.880 mmol). LC-MS (ESI), $C_{15}H_{20}N_5O_2$ [M+H]$^+$: m/z=302.3.

2): (1R,2R)-2-(8-methoxy-1H-[1,2,3]triazolo[4,5-h]quinazolin-1-yl)-1-methylcyclopentan-1-ol (15f)

By referring to the synthesis method of 15a in Example II.1, compound 15f (66.0 mg, 0.220 mmol, yield 80%) was prepared from 14b (84.0 mg, 0.280 mmol). LC-MS (ESI), $C_{15}H_{18}N_5O_2$ [M+H]$^+$: m/z=300.1.

3): 1-((1R,2R)-2-hydroxy-2-methylcyclopentyl)-1H-[1,2,3]triazolo[4,5-h]quinazolin-8-yl trifluoromethanesulfonate (16f)

By referring to the synthesis method of 16b in Example II.21, compound 16f (45.0 mg, 0.108 mmol, yield 58%) was prepared from 15f (56.0 mg, 0.186 mmol). LC-MS (ESI), $C_{15}H_{15}F_3N_5O_4S$ [M+H]$^+$: m/z=418.1.

4): (1R,2R)-1-methyl-2-(8-((1-(methylsulfonyl)piperidin-4-yl)amino)-1H-[1,2,3]triazolo[4,5-h]quinazolin-1-yl) cyclopentan-1-ol (II.32)

By referring to the synthesis method of I.1 in Example I.1, compound II.32 (35.0 mg, 0.079 mmol, 78%) was prepared from 16f (42.0 mg, 0.100 mmol). LC-MS (ESI), $C_{20}H_{28}N_7O_3S$ [M+H]$^+$: m/z=446.4.

(1R,2R)-2-(4-(difluoromethyl)-8-((1-(methylsulfonyl)piperidin-4-yl)amino)-1H-[1,2,3]triazolo[4,5-h]quinazolin-1-yl)-1-methylcyclopentan-1-ol (II.33)

By referring to the synthesis method of I.14 in Example I.14, compound II.33 (20.0 mg, 0.042 mmol, yield 63%) was prepared from II.32 (30.0 mg, 0.067 mmol). LC-MS (ESI), $C_{21}H_{28}F_2N_7O_3S$ [M+H]$^+$: m/z=496.2.

Examples II.34-II.36

| Example No. | Side chain structure | Example structure | Example name |
|---|---|---|---|
| II.34 | 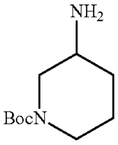 8u | 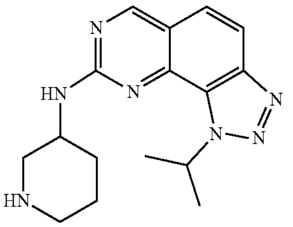 [SMILES: CC(C)n1nnc2ccc3cnc(NC4CCCNC4)nc3c21] | 1-isopropyl-N-(piperidin-3-yl)-1H-[1,2,3]triazolo[4,5-h]quinazolin-8-amine |

-continued

| Example No. | Side chain structure | Example structure | Example name |
| --- | --- | --- | --- |
| II.35 | 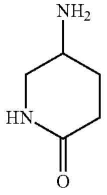 8v | 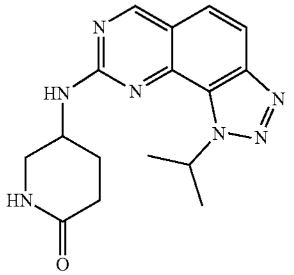 [SMILES: CC(C)n1nnc2ccc3cnc(NC4CCC(=O)NC4)nc3c21] | 5-((1-isopropyl-1H-[1,2,3]triazolo[4,5-h]quinazolin-8-yl)amino)piperidin-2-one |
| II.36 | 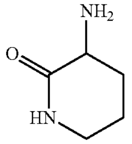 8w | 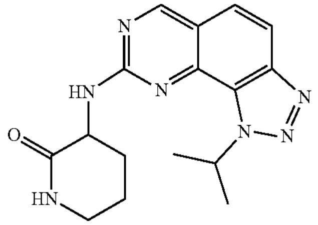 [SMILES: CC(C)n1nnc2ccc3cnc(NC4CCCNC4=O)nc3c21] | 3-((1-isopropyl-1H-[1,2,3]triazolo[4,5-h]quinazolin-8-yl)amino)piperidin-2-one |

By referring to the synthesis method of I.2a in Example I.2, compound II.34a (77.0 mg, 0.187 mmol, yield 77%) was prepared from 16a (60.0 mg, 0.243 mmol) and tert-butyl 3-aminopiperidine-1-carboxylate 8u (97.0 mg, 0.486 mmol). $^1$H NMR (400 MHz, chloroform-d, ppm) δ 9.02 (s, 1H), 7.76 (d, J=8.8 Hz, 1H), 7.49 (d, J=8.8 Hz, 1H), 6.13 (s, 1H), 5.53 (s, 1H), 4.10 (s, 1H), 3.39 (d, J=174.9 Hz, 4H), 2.07 (s, 1H), 1.86 (d, J=5.9 Hz, 3H), 1.79 (d, J=6.3 Hz, 3H), 1.73-1.68 (m, 1H), 1.61 (d, J=7.9 Hz, 1H), 1.42 (s, 9H), 1.25 (s, 1H).

By referring to the synthesis method of I.2 in Example I.2, compound II.34 (52.0 mg, 0.168 mmol, yield 90%) was prepared from II.34a (77.0 mg, 0.187 mmol). $^1$H NMR (400 MHz, dimethyl sulfoxide-$d_6$, ppm) δ 9.58 (s, 1H), 9.25 (s, 1H), 9.03 (s, 1H), 7.78-7.64 (m, 2H), 6.04 (d, J=20.3 Hz, 1H), 4.33 (s, 1H), 3.46 (s, 1H), 3.21 (d, J=12.5 Hz, 1H), 2.89 (s, 2H), 2.08 (s, 1H), 1.91 (d, J=5.9 Hz, 2H), 1.75 (t, J=6.3 Hz, 6H), 1.66-1.58 (m, 1H).

By referring to the synthesis method of I.1 in Example I.1, compound II.35 (62.0 mg, 0.190 mmol, yield 78%) was prepared from 16a (60.0 mg, 0.243 mmol) and 5-aminopiperidin-2-one 8v (55.0 mg, 0.486 mmol). $^1$H NMR (400 MHz, chloroform-d, ppm) δ 9.25 (s, 1H), 7.97 (s, 1H), 7.82-7.61 (m, 2H), 7.52 (s, 1H), 6.05 (s, 1H), 4.24 (s, 1H), 3.55 (d, J=48.1 Hz, 1H), 3.19 (d, J=45.1 Hz, 1H), 2.41 (dt, J=17.5, 5.7 Hz, 1H), 2.35-2.26 (m, 1H), 2.14 (s, 1H), 1.97-1.84 (m, 1H), 1.74 (d, J=6.6 Hz, 6H).

By referring to the synthesis method of I.1 in Example I.1, compound II.36 (63.0 mg, 0.190 mmol, yield 80%) was prepared from 16a (60.0 mg, 0.243 mmol) and 3-aminopiperidin-2-one 8w (55.0 mg, 0.486 mmol). $^1$H NMR (400 MHz, chloroform-d, ppm) δ 9.07 (s, 1H), 7.77 (d, J=8.8 Hz, 1H), 7.51 (d, J=8.9 Hz, 1H), 6.36 (s, 1H), 6.14 (h, J=6.7 Hz, 1H), 5.86 (s, 1H), 4.57 (dt, J=11.2, 5.4 Hz, 1H), 3.47 (ddd, J=7.7, 4.5, 1.9 Hz, 2H), 2.78 (dt, J=13.6, 4.8 Hz, 1H), 2.24-1.93 (m, 3H), 1.82 (dd, J=6.8, 2.4 Hz, 6H).

Example II.37

1-isopropyl-N-(1-(methylsulfonyl)piperidin-4-yl)-4,5-dihydro-1H-[1,2,3]triazolo[4,5-h]quinazolin-8-amine (II.37)

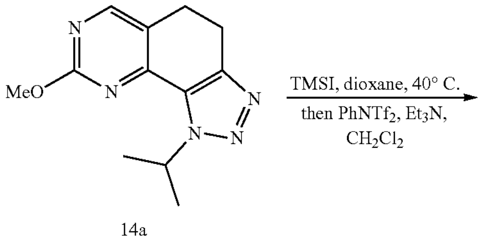

14a

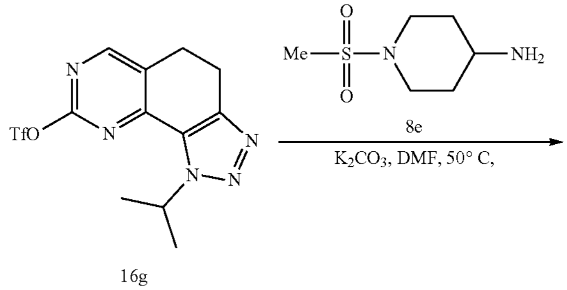

16g

-continued

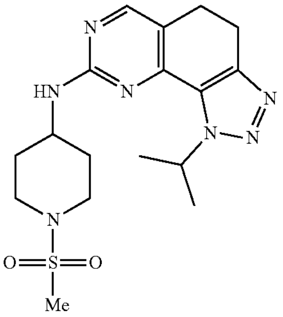

II.37

1): 1-isopropyl-4,5-dihydro-1H-[1,2,3]triazolo[4,5-h]quinazolin-8-yl trifluoromethanesulfonate (16g)

By referring to the synthesis method of 16b in Example II.21, compound 16g (149.0 mg, 0.410 mmol, yield 50%) was prepared from 14a (200.0 mg, 0.820 mmol). $^{1}$H NMR (400 MHz, chloroform-d, ppm) δ 8.56 (s, 1H), 5.67-5.50 (m, 1H), 3.16 (q, J=1.8, 1.1 Hz, 4H), 1.70 (d, J=6.7 Hz, 6H).

2): 1-isopropyl-N-(1-(methylsulfonyl)piperidin-4-yl)-4,5-dihydro-1H-[1,2,3]triazolo[4,5-h]quinazolin-8-amine (II.37)

By referring to the synthesis method of I.1 in Example I.1, compound II.37 (36.0 mg, 0.090 mmol, yield 85%) was prepared from 16g (40.0 mg, 0.11 mmol) and 8e (39 mg, 0.220 mmol). $^{1}$H NMR (400 MHz, chloroform-d, ppm) δ 8.17 (s, 1H), 5.69 (hept, J=6.7 Hz, 1H), 5.01 (d, J=7.5 Hz, 1H), 3.99-3.89 (m, 1H), 3.78 (d, J=12.3 Hz, 2H), 3.03 (td, J=7.4, 6.8, 1.0 Hz, 2H), 2.92 (ddt, J=15.4, 9.1, 5.1 Hz, 4H), 2.83 (s, 3H), 2.19 (dt, J=12.3, 3.6 Hz, 2H), 1.68 (d, J=6.7 Hz, 8H).

Example II.38 and 11.39

| Example No. | Example structure | Example name |
| --- | --- | --- |
| II.38 | 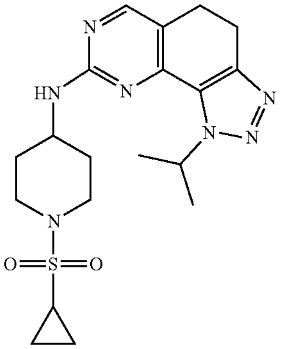 [SMILES: CC(C)n1nnc2c1-c1nc(NC3CCN(S(=O)(=O)C4CC4)CC3)ncc1CC2] | N-(1-(cyclopropylsulfonyl)piperidin-4-yl)-1-isopropyl-4,5-dihydro-1H-[1,2,3]triazolo[4,5-h]quinazolin-8-amine |
| II.39 | 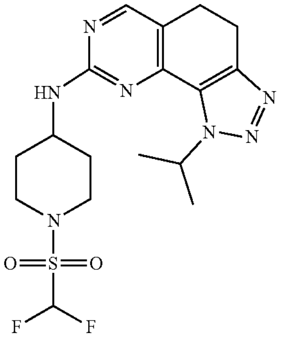 [SMILES: CC(C)n1nnc2c1-c1nc(NC3CCN(S(=O)(=O)C(F)F)CC3)ncc1CC2] | N-(1-((difluoromethyl)sulfonyl)piperidin-4-yl)-1-isopropyl-4,5-dihydro-1H-[1,2,3]triazolo[4,5-h]quinazolin-8-amine |

By referring to the synthesis method of 0.15 in Example I.15, compound II.38 (2.0 mg, 0.07 mmol, yield 70%) was prepared from 16g (40.0 mg, 0.110 mmol) and 8p (45 mg, 0.220 mmol). $^1$H NMR (400 MHz, chloroform-d, ppm) δ 8.17 (s, 1H), 5.69 (hept, J=6.7 Hz, 1H), 5.06 (s, 1H), 3.94 (tdt, J=10.7, 7.8, 4.0 Hz, 1H), 3.79 (dd, J=10.5, 6.1 Hz, 2H), 3.13-2.97 (m, 4H), 2.97-2.84 (m, 2H), 2.29 (tt, J=7.9, 4.8 Hz, 1H), 2.18 (dt, J=13.3, 3.6 Hz, 2H), 1.68 (d, J=6.7 Hz, 8H), 1.22-1.15 (m, 2H), 1.04-0.97 (m, 2H).

By referring to the synthesis method of I.15 in Example I.15, compound II.39 (39.0 mg, 0.090 mmol, yield 83%) was prepared from 16g (40.0 mg, 0.110 mmol) and 8s (47.0 mg, 0.220 mmol). 1H NMR (400 MHz, chloroform-d, ppm) δ 8.18 (s, 1H), 6.16 (d, J=53.9 Hz, 1H), 5.68 (p, J=6.7 Hz, 1H), 5.00 (d, J=7.4 Hz, 1H), 4.06-3.94 (m, 3H), 3.28 (ddd, J=13.8, 11.2, 2.8 Hz, 2H), 3.03 (td, J=7.4, 6.7, 1.0 Hz, 2H), 2.90 (dd, J=8.6, 6.8 Hz, 2H), 2.24-2.15 (m, 2H), 1.68 (d, J=6.7 Hz, 8H).

Biological Example

Assay of Kinase Activity

The inhibitory effect of compounds against the kinase CDK4/cyclin D3 was detected by Caliper Mobility Shift Assay method. The final concentration of the compounds to be tested was set at 10 concentrations starting from 1 uM by 3-fold serial dilution. 5 μL of compounds at 5-fold final concentration and 10 μL of CDK4/cyclin D3 kinase solution at a final concentration of 10 nM was added to a 384-well reaction plate, respectively. The plate was pre-incubated for 10 min at room temperature (with negative control wells containing 10 uL of kinase buffer and 5 uL of 5% DMSO; positive control wells containing 10 μL of kinase solution and 5 uL of 5% DMSO). The reaction was initiated by adding 10 μL of ATP at a final concentration of 250 uM and the corresponding substrate peptide mixture at room temperature for 150 minutes. 30 uL of stop detection solution containing EDTA was added to stop the kinase reaction. Caliper EZ Reader was used to read the conversion rate. Conversion inhibition rate %=(average conversion rate of positive control %−conversion rate of sample %)/(average conversion rate of positive control %−average conversion rate of negative control %). wherein: negative control wells represent the conversion rate readings of wells without enzymatic activity; positive control wells represent conversion readings for wells with no compound inhibition. The log(inhibitor) vs. response—Variable slope of the analysis software GraphPad Prism 5 was used with log concentration value as the X-axis and the percent inhibition rate as the Y-axis to fit the dose-response curve, the $IC_{50}$ value of each compound on the enzyme activity was thus obtained. Calculation formula: Y=Bottom+(Top−Bottom)/(1+10^((Log $IC_{50}$−X)*HillSlope)).

The $IC_{50}$ values and inhibitory activities of compounds of the present disclosure on CDK6/Cyclin D3, CDK2/Cyclin A2, and CDK9/cyclin T1 were tested in a similar manner.

The compounds of the present disclosure were tested in the kinase activity assay. It was found that they had inhibitory activities of <100 nM on CDK2, CDK4, CDK6 and CDK9. The results of the enzyme inhibitory activities of the representative compounds of the present disclosure are shown in the table below.

| Compound No. | CDK2/A2 $IC_{50}$ (nM) | CDK4/D3 $IC_{50}$ (nM) | CDK6/D3 $IC_{50}$ (nM) |
|---|---|---|---|
| I.1 | 42 | 32 | 36 |
| I.2 | 12 | 22 | 26 |
| I.3 | 258 | 26 | 38 |
| I.4 | 249 | 47 | 68 |
| I.5 | 1 | 10 | 24 |
| I.6 | 1 | 5 | 12 |
| I.7 | 8 | 7 | 3 |
| I.8 | 9 | 6 | 3 |
| I.9 | 5 | 6 | 7 |
| I.10 | 49 | 72 | 71 |
| I.11 | 1 | 10 | 24 |
| I.12 | 1 | 5 | 13 |
| I.13 | 1 | 3 | 6 |
| I.14 | 2 | 5 | 8 |
| I.15 | 2 | 10 | 8 |
| II.1 | >500 | >500 | >500 |
| II.2 | 20 | 16 | 22 |
| II.3 | 12 | 22 | 26 |
| II.4 | 20 | 16 | 22 |
| II.5 | 140 | 22 | 34 |
| II.6 | 35 | 10 | 12 |
| II.7 | 465 | 40 | 26 |
| II.8 | >500 | 43 | 37 |
| II.9 | 356 | 26 | 35 |
| II.10 | 336 | 22 | 46 |
| II.11 | 1 | 8 | 15 |
| II.12 | 151 | 51 | 89 |
| II.13 | 110 | 41 | 90 |
| II.14 | 0.2 | 3 | 5 |
| II.15 | 0.3 | 3 | 4 |
| II.16 | 0.2 | 3 | 5 |
| II.17 | 1 | 8 | 15 |
| II.18 | 1 | 3 | 8 |
| II.19 | 0.4 | 3 | 4 |
| II.20 | 0.2 | 4 | 12 |
| II.21 | 0.2 | 2 | 5 |
| II.22 | 0.2 | 3 | 4 |
| II.23 | 0.4 | 3 | 9 |
| II.24 | 1 | 4 | 16 |
| II.25 | 0.2 | 3 | 5 |
| II.26 | 0.4 | 3 | 8 |
| II.27 | 0.2 | 3 | 5 |
| II.28 | 0.2 | 3 | 7 |
| II.29 | 0.2 | 1 | 3 |
| II.30 | 0.3 | 3 | 6 |
| II.31 | 0.2 | 1 | 2 |
| II.32 | 0.2 | 5 | 9 |
| II.33 | 0.3 | 3 | 5 |
| II.34 | 296 | 55 | 35 |
| II.35 | 10 | 50 | 58 |
| II.36 | >500 | 253 | 446 |
| II.37 | 0.5 | 4 | 12 |
| II.38 | 0.3 | 3 | 7 |
| II.39 | 0.5 | 3 | 10 |

The results of the enzyme inhibitory activity of the representative compounds of the present disclosure on CDK9 are shown in the following table.

| Compound No. | CDK9/T1 $IC_{50}$ (nM) |
|---|---|
| I.1 | 25 |
| I.2 | 16 |
| II.2 | 8 |
| II.8 | 11 |

The above content is a further detailed description of the present disclosure in conjunction with specific alternative embodiments, and it cannot be concluded that the specific embodiments of the present disclosure are limited to these descriptions. Those skilled in the art will appreciate that several simple deductions or substitutions may be made without departing from the spirit of the present disclosure, which should be regarded to be within the scope of the present disclosure.

The invention claimed is:

1. A compound, or a pharmaceutically acceptable salt, an enantiomer, a diastereomer, a racemate, a solvate, a hydrate, a polymorph, or an isotope variant thereof, or a mixture thereof, which has a structure of formula (X):

(X)

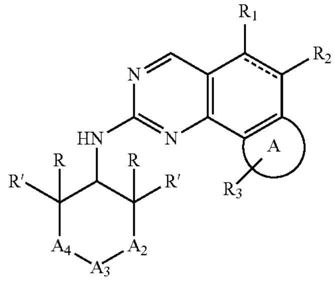

wherein:

⎓ indicates a single bond or a double bond;

ring A is oxazolyl, isoxazolyl, thiazolyl, isothiazolyl, triazolyl, oxadiazolyl, and thiadiazolyl; alternatively selected from:

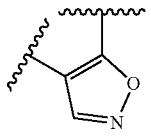

and

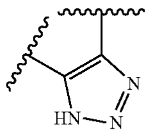

;

$A_2$ is CRR' or NR";

$A_3$ is CRR' or $NR_4$;

$A_4$ is CRR' or NR";

or $A_3$, $A_4$ and substituents thereon are combined to form $C_{6-10}$ aryl or 5- to 10-membered heteroaryl;

R and R' are independently selected from H, D, $—OR_{O1}$, $—NR_{N1}R_{N2}$, $C_{1-6}$ alkyl, $C_{1-6}$ haloalkyl, $—C_{0-6}$ alkylene-$C_{3-7}$ cycloalkyl, $—C_{0-6}$ alkylene-3- to 7-membered heterocyclyl, $—C_{0-6}$ alkylene-$C_{6-10}$ aryl and $—C_{0-6}$ alkylene-5- to 10-membered heteroaryl; or R, R' and the carbon atom attached thereto are combined to form C═O;

$R_1$ is selected from H, D, halogen, —CN, $—OR_a$, $—SR_a$, $—NR_bR_c$, $—C(O)R_a$, $—C(O)OR_a$, $—C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, $—OR_a$, $—SR_a$, $—NR_bR_c$, $—C(O)R_a$, $—C(O)OR_a$, $—C(O)NR_bR_c$, $—C_{0-6}$ alkylene-$OR_5$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, $—C_{0-6}$ alkylene-$C_{3-7}$ cycloalkyl, $—C_{0-6}$ alkylene-3- to 7-membered heterocyclyl, $—C_{0-6}$ alkylene-$C_{6-10}$ aryl and $—C_{0-6}$ alkylene-5- to 10-membered heteroaryl, which may be optionally substituted by 1, 2, 3, 4 or more substituents selected from D, halogen, $—C_{0-6}$ alkylene-$OR_5$, —CN, $—NR_6R_7$, $C_{1-6}$ alkyl and $C_{1-6}$ haloalkyl;

$R_a$ is independently selected from H, $C_{1-6}$ alkyl, $C_{2-6}$ alkenyl, $C_{2-6}$ alkynyl, $C_{1-6}$ haloalkyl, $—C_{0-6}$ alkylene-$C_{3-7}$ cycloalkyl, $—C_{0-6}$ alkylene-3- to 7-membered heterocyclyl, $—C_{0-6}$ alkylene-$C_{6-10}$ aryl and $—C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, $—C_{0-6}$ alkylene-$C_{3-7}$ cycloalkyl, $—C_{0-6}$ alkylene-3- to 7-membered heterocyclyl, $—C_{0-6}$ alkylene-$C_{6-10}$ aryl and $—C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_{O1}$, $R_{N1}$ and $R_{N2}$ are independently selected from H, $C_{1-6}$ alkyl, $C_{1-6}$ haloalkyl, $—C(O)R_d$, $—S(O)_mR_d$, $—C_{1-6}$ alkylene-$OR_5$, $—C_{1-6}$ alkylene-$NR_6R_7$, $—C_{0-6}$ alkylene-$C_{3-7}$ cycloalkyl, $—C_{0-6}$ alkylene-3- to 7-membered heterocyclyl, $—C_{0-6}$ alkylene-$C_{6-10}$ aryl and $—C_{0-6}$ alkylene-5- to 10-membered heteroaryl;

or $R_{N1}$ and $R_{N2}$ are taken together with the nitrogen atom to which they are attached to form 3- to 7-membered heterocyclyl or 5- to 10-membered heteroaryl, which is optionally substituted by 1, 2 or 3 $R_8$ groups;

$R_4$ and R" are independently selected from H, $C_{1-6}$ alkyl, $C_{1-6}$ haloalkyl, $C_{2-6}$ alkenyl, $C_{2-6}$ alkynyl, $—C(O)R_d$, $—S(O)_mR_d$, $—C_{0-6}$ alkylene-$C_{3-7}$ cycloalkyl, $—C_{0-6}$ alkylene-3- to 7-membered heterocyclyl, $—C_{0-6}$ alkylene-$C_{6-10}$ aryl and $—C_{0-6}$ alkylene-5- to 10-membered heteroaryl;

$R_d$ is selected from $C_{1-6}$ alkyl, $C_{1-6}$ haloalkyl, $—C_{0-6}$ alkylene-$OR_5$, $—C_{0-6}$ alkylene-$NR_6R_7$, $—C_{0-6}$ alkylene-$C_{3-7}$ cycloalkyl, $—C_{0-6}$ alkylene-3- to 7-membered heterocyclyl, $—C_{0-6}$ alkylene-$C_{6-10}$ aryl and $—C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl;

$R_8$ is independently selected from H, D, halogen, —CN, -L-$C_{3-7}$ cycloalkyl, -L-3- to 7-membered heterocyclyl, -L-$C_{6-10}$ aryl and -L-5- to 10-membered heteroaryl;

L is selected from a chemical bond, —C(O)—, —C(O)NH—, $—C_{1-6}$ alkylene-, $—C_{2-6}$ alkenylene- and $—C_{2-6}$ alkynylene-; and $R_8$ is further substituted by H, D, halogen, —CN, $C_{1-6}$ alkyl or $C_{1-6}$ haloalkyl.

2. The compound of claim 1 or a pharmaceutically acceptable salt, an enantiomer, a diastereomer, a racemate, a solvate, a hydrate, a polymorph, a or an isotope variant thereof, or a mixture thereof, which has a structure of general formula (I-1) or (II-1):

(I-1)

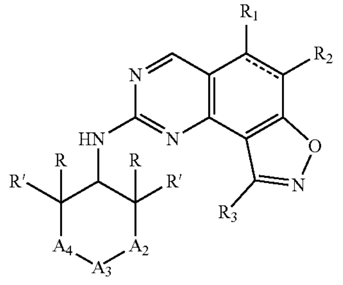

or

-continued (II-1)

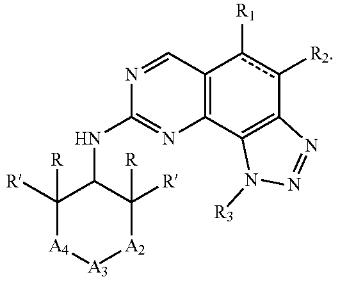

3. The compound of claim 1, or a pharmaceutically acceptable salt, an enantiomer, a diastereomer, a racemate, a solvate, a hydrate, a polymorph, or an isotope variant thereof, or a mixture thereof, which has a structure of general formula (I-2) or (II-2):

(I-2)

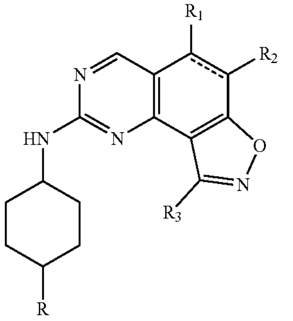

or (II-2)

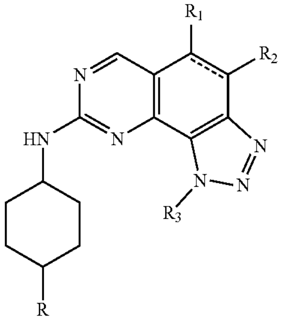

wherein:

$\overline{\overline{\cdots}}$ indicates a single bond or a double bond;

$R_1$ is H, D, halogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;

R is —$NR_{N1}R_{N2}$;

$R_{N1}$ is selected from H, $C_{1-6}$ alkyl and $C_{1-6}$ haloalkyl;

$R_{N2}$ is selected from $C_{1-6}$ alkyl, $C_{1-6}$ haloalkyl, —$S(O)_mR_d$, —$C(O)R_d$, —$C_{1-6}$ alkylene-$OR_5$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

4. The compound of claim 3, or a pharmaceutically acceptable salt, an enantiomer, a diastereomer, a racemate, a solvate, a hydrate, a polymorph, or an isotope variant thereof, or a mixture thereof, wherein:

$\overline{\overline{\cdots}}$ indicates a single bond or a double bond;

$R_1$ is H, D, or halogen;

$R_2$ is selected from H, D, and halogen;

$R_3$ is selected from $C_{1-6}$ alkyl and $C_{1-6}$ haloalkyl;

R is —$NR_{N1}R_{N2}$;

$R_{N1}$ is selected from H, $C_{1-6}$ alkyl and $C_{1-6}$ haloalkyl;

$R_{N2}$ is selected from $C_{1-6}$ alkyl, $C_{1-6}$ haloalkyl, —$S(O)_mR_d$, —$C_{1-6}$ alkylene-$OR_5$, and -3- to 7-membered heterocyclyl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl;

alternatively, wherein:

$\overline{\overline{\cdots}}$ d indicates a single bond or a double bond;

$R_1$ is H;

$R_2$ is H;

$R_3$ is $C_{1-6}$ alkyl;

R is —$NR_{N1}R_{N2}$;

$R_{N1}$ is selected from H and $C_{1-6}$ alkyl, alternatively H and Me;

$R_{N2}$ is selected from $C_{1-6}$ alkyl, —$S(O)_mR_d$, —$C_{0-6}$ alkylene-$OR_5$,

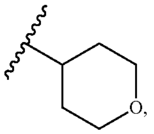 and 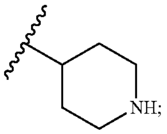

alternatively Me, —$S(O)_2Me$, —$CH_2CH_2$—$OCH_3$,

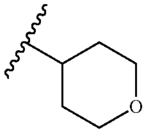 and 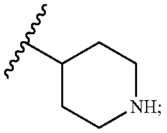

$R_d$ is $C_{1-6}$ alkyl;

m is 2;

$R_5$ is selected from H, $C_{1-6}$ alkyl and $C_{1-6}$ haloalkyl;

alternatively, wherein:

$\overline{\overline{\cdots}}$ indicates a single bond or a double bond;

$R_1$ is H, D, halogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;

R is —$NR_{N1}R_{N2}$;

$R_{N1}$ is H;

$R_{N2}$ is selected from —$S(O)_mR_d$ and —$C(O)R_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl;

alternatively, wherein:

$\overline{\underline{\phantom{xx}}}$ indites a single bond or a double bond;

$R_1$ is H, D, halogen, $C_{1-6}$ alkyl, or $C_{1-6}$ haloalkyl;

$R_2$ is selected from H, D, halogen, $C_{1-6}$ alkyl, and $C_{1-6}$ haloalkyl;

$R_3$ is selected from $C_{1-6}$ alkyl and $C_{1-6}$ haloalkyl;

R is —$NR_{N1}R_{N2}$;

$R_{N1}$ is H;

$R_{N2}$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl;

alternatively wherein:

$\overline{\underline{\phantom{xx}}}$ indicates a single bond or a double bond;

$R_1$ is H, D, or halogen;

$R_2$ is selected from H, D, and halogen;

$R_3$ is selected from $C_{1-6}$ alkyl and $C_{1-6}$ haloalkyl;

R is —$NR_{N1}R_{N2}$;

$R_{N1}$ is H;

$R_{N2}$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl;

alternatively, wherein:

$\overline{\underline{\phantom{xx}}}$ indicates a single bond or a double bond;

$R_1$ is H;

$R_2$ is H;

$R_3$ is $C_{1-6}$ alkyl;

R is —$NR_{N1}R_{N2}$;

$R_{N1}$ is H;

$R_{N2}$ is —$S(O)_mR_d$; alternatively —$S(O)_2Me$;

$R_d$ is $C_{1-6}$ alkyl;

m is 2;

alternatively, wherein the compound has a structure of general formula (I-3), (I-3-1), (I-3-2), (II-3), (II-3-1) or (II-3-2):

(I-3)

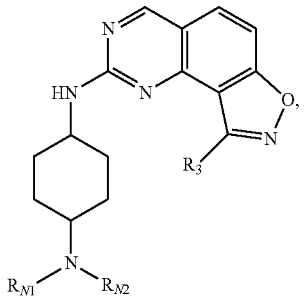

(I-3-1)

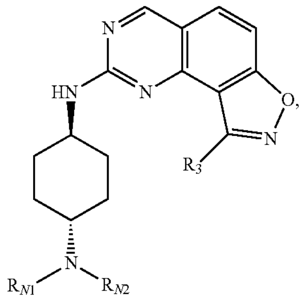

(I-3-2)

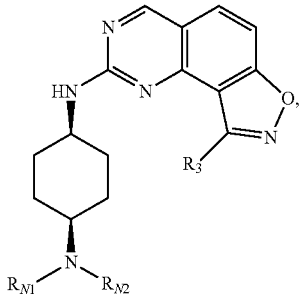

(II-3)

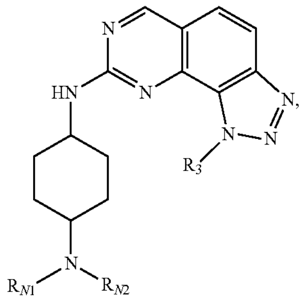

(II-3-1)

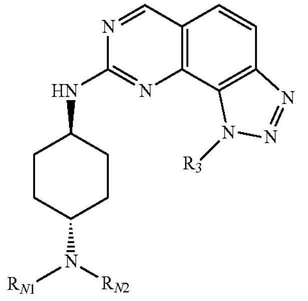

or

-continued (II-3-2)

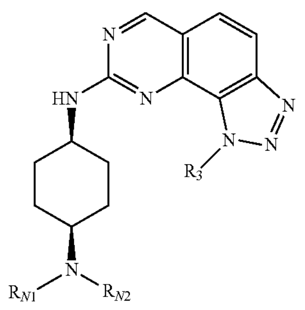

wherein $R_3$, $R_{N1}$ and $R_{N2}$ are as defined in claim 3.

5. The compound of claim 1, or a pharmaceutically acceptable salt, an enantiomer, a diastereomer, a racemate, a solvate, a hydrate, a polymorph, or an isotope variant thereof, or a mixture thereof, which has a structure of general formula (I-1) or (II-1):

(I-1)

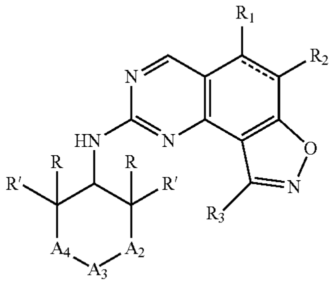

or (II-1)

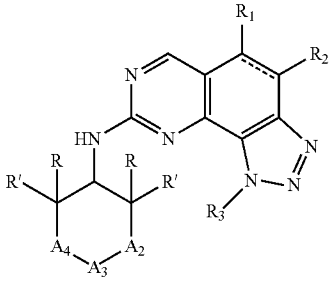

wherein:

⎓ indicates a single bond or a double bond;

$A_2$ is CRR' or NR'';

$A_3$ is CRR' or $NR_4$;

$A_4$ is CRR' or NR'';

or $A_3$, $A_4$ and substituents thereon are combined to form $C_{6-10}$ aryl or 5- to 10-membered heteroaryl;

R and R' are independently selected from H, D, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_1$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_2$ is selected from H, D, halogen, —CN, —$OR_a$, —$SR_a$, —$NR_bR_c$, —C(O)$R_a$, —C(O)$OR_a$, —C(O)$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl; wherein the $C_{3-7}$ cycloalkyl or 3- to 7-membered heterocyclyl is optionally substituted by oxo or thioxo;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_4$ and R'' are independently selected from H, $C_{1-6}$ alkyl, $C_{1-6}$ haloalkyl, $C_{2-6}$ alkenyl, $C_{2-6}$ alkynyl, —C(O)$R_d$, —$S(O)_mR_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

6. The compound of claim 5, or a pharmaceutically acceptable salt, an enantiomer, a diastereomer, a racemate, a solvate, a hydrate, a polymorph, or an isotope variant thereof, or a mixture thereof, wherein:

⎓ indicates a single bond or a double bond;

$A_2$ is CRR' or NR'';

$A_3$ is CRR' or $NR_4$;

$A_4$ is CRR' or NR'';

or $A_3$, $A_4$ and substituents thereon are combined to form $C_{6-10}$ aryl or 5- to 10-membered heteroaryl;

R and R' are independently selected from H, D, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_1$ is selected from H, D, halogen, —CN, —$OR_a$, —$SR_a$ and —$NR_bR_c$;

$R_2$ is selected from H, D, halogen, —CN, —$OR_a$, —$SR_a$ and —$NR_bR_c$;

$R_3$ is selected from $C_{1-6}$ alkyl and $C_{1-6}$ haloalkyl;

$R_a$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_4$ and R" are independently selected from H, $C_{1-6}$ alkyl, $C_{1-6}$ haloalkyl, $C_{2-6}$ alkenyl, $C_{2-6}$ alkynyl, —C(O)$R_d$, —S(O)$_m$$R_d$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, $C_{6-10}$ aryl and 6- to 10-membered heteroaryl;

m is 0, 1 or 2;

$R_5$, $R_6$ and $R_7$ are independently selected from H, $C_{1-6}$ alkyl and $C_{1-6}$ haloalkyl.

7. The compound of claim 1, or a pharmaceutically acceptable salt, an enantiomer, a diastereomer, a racemate, a solvate, a hydrate, a polymorph, or an isotope variant thereof, or a mixture thereof, which has a structure of general formula (I-4), (I-4-1), (I-4-2), (II-4), (II-4-1) or (II-4-2):

(I-4)

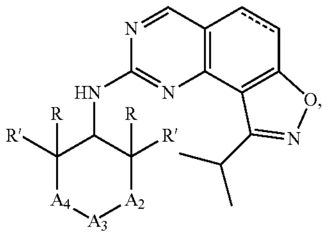

(I-4-1)

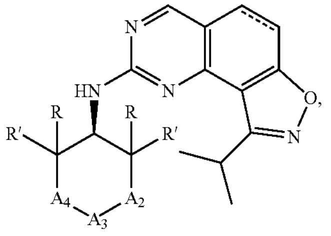

(I-4-2)

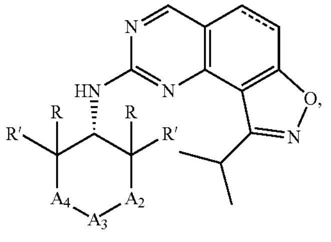

(II-4)

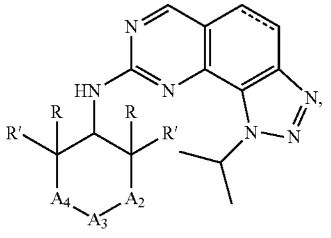

-continued (II-4-1)

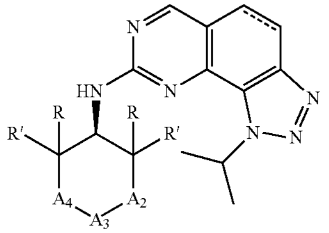

or (II-4-2)

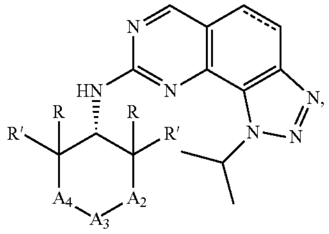

wherein:

⎓ indicates a single bond or a double bond;

$A_2$ is CRR' or NR";

$A_3$ is CRR' or $NR_4$;

$A_4$ is CRR' or NR";

or $A_3$, $A_4$ and substituents thereon are combined to form $C_{6-10}$ aryl;

R and R' are independently selected from H, D, $C_{1-6}$ alkyl, $C_{1-6}$ haloalkyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

$R_4$ and R" are independently selected from H, $C_{1-6}$ alkyl, $C_{1-6}$ haloalkyl, —C(O)$R_d$ and —S(O)$_m$$R_d$; alternatively selected from H, $C_{1-6}$ alkyl, $C_{1-6}$ haloalkyl and —S(O)$_m$$R_d$; alternatively selected from: H, methyl,

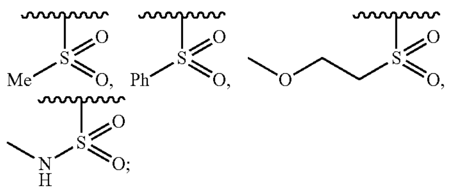

d is selected from $C_{1-6}$ alkyl, $C_{1-6}$ haloalkyl, —$C_{0-6}$ alkylene-$OR_5$, —$C_{0-6}$ alkylene-$NR_6R_7$, $C_{6-10}$ aryl and 6- to 10-membered heteroaryl;

m is 1 or 2;

$R_5$, $R_6$ and $R_7$ are independently selected from H, $C_{1-6}$ alkyl and $C_{1-6}$ haloalkyl.

8. The compound of claim 7, or a pharmaceutically acceptable salt, an enantiomer, a diastereomer, a racemate, a solvate, a hydrate, a polymorph, or an isotope variant thereof, or a mixture thereof, wherein:

⎓ indicates a single bond or a double bond;

$A_2$ is CRR';

$A_3$ is $NR_4$;

$A_4$ is CRR';

R and R' are H or D;

$R_4$ is selected from H, —C(O)$R_d$ and —S(O)$_m$$R_d$; alternatively H and —S(O)$_m$$R_d$;

$R_d$ is selected from $C_{1-6}$ alkyl and $C_{1-6}$ haloalkyl;

m is 1 or 2.

9. The compound of claim 1, or a pharmaceutically acceptable salt, an enantiomer, a diastereomer, a racemate, a solvate, a hydrate, a polymorph, or an isotope variant thereof, or a mixture thereof, which has a structure of general formula (I-5) or (II-5):

(I-5)

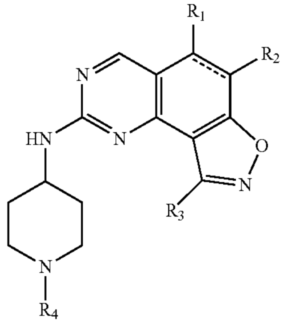

or (II-5)

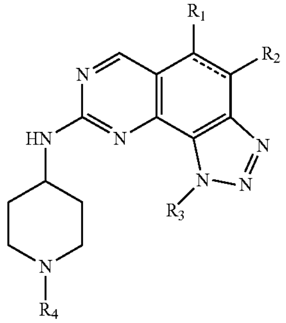

wherein:

$\overline{\underline{\ \ \ }}$ indicates a single bond or a double bond;

$R_1$ is selected from H, D, halogen, —CN, —$OR_a$, —$SR_a$ and —$NR_bR_c$;

$R_2$ is selected from H, D, halogen, —$SR_a$, —$NR_bR_c$, $C_{1-6}$ alkyl, $C_{1-6}$ haloalkyl, —$C_{0-6}$ alkylene-$OR_a$, —$C_{0-6}$ alkylene-CN, $C_{3-7}$ cycloalkyl, 3- to 7-membered heterocyclyl, $C_{6-10}$ aryl and 5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl, —$C_{0-6}$ alkylene-5- to 10-membered heteroaryl, —C(O)$R_d$, or —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 0, 1 or 2;

$R_5$, $R_6$ and $R_7$ are independently selected from H, $C_{1-6}$ alkyl and $C_{1-6}$ haloalkyl.

10. The compound of claim 9, or a pharmaceutically acceptable salt, an enantiomer, a diastereomer, a racemate, a solvate, a hydrate, a polymorph, or an isotope variant thereof, or a mixture thereof, wherein:

$\overline{\underline{\ \ \ }}$ indicates a single bond or a double bond;

$R_1$ is selected from H, D, and halogen;

$R_2$ is selected from H, D, halogen, $C_{1-6}$ alkyl, $C_{1-6}$ haloalkyl, —$C_{0-6}$ alkylene-$OR_a$, —$C_{0-6}$ alkylene-CN, $C_{3-7}$ cycloalkyl, 3- to 7-membered heterocyclyl, $C_{6-10}$ aryl and 5- to 10-membered heteroaryl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3 or 4 substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is H, $C_{1-6}$ alkyl, $C_{1-6}$ haloalkyl, —C(O)$R_d$, or —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl alternatively, wherein:

$\overline{\underline{\ \ \ }}$ indicates a single bond or a double bond;

$R_1$ is H, D, or halogen;

$R_2$ is selected from H, D, halogen, $C_{1-6}$ alkyl, $C_{1-6}$ haloalkyl, —$C_{0-6}$ alkylene-$OR_a$, and —$C_{0-6}$ alkylene-CN;

$R_a$ is H, $C_{1-6}$ alkyl, or $C_{1-6}$ haloalkyl;

$R_3$ is selected from $C_{1-6}$ alkyl and $C_{1-6}$ haloalkyl;

$R_4$ is H, $C_{1-6}$ alkyl, $C_{1-6}$ haloalkyl, or —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl;

alternatively, wherein:

$\overline{\underline{\ \ \ }}$ indicates a single bond or a double bond;

$R_1$ is H, or halogen;

$R_2$ is selected from H, D, halogen, $C_{1-6}$ alkyl, $C_{1-6}$ haloalkyl, and —$C_{1-6}$ alkylene-OH;

$R_3$ is $C_{1-6}$ alkyl;

$R_4$ is H, $C_{1-6}$ alkyl, or —$S(O)_mR_d$; alternatively H, Me,

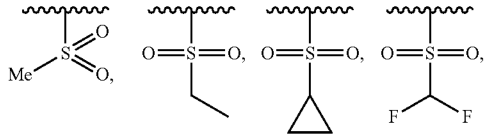

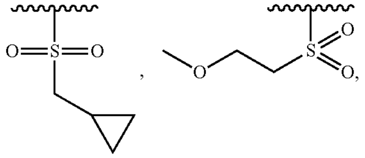

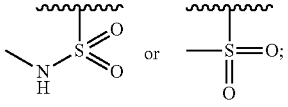

or ;

$R_d$ is $C_{1-6}$ alkyl, $C_{1-6}$ haloalkyl, —$C_{0-6}$ alkylene-$OR_5$, —$NR_6R_7$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl;

alternatively wherein:

⎓ indicates a single bond or a double bond;

$R_1$ is selected from H, D, halogen, —CN, —$SR_a$ and —$NR_bR_c$;

$R_2$ is selected from H, D, halogen, —CN, —$SR_a$, —$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is —$S(O)_mR_d$, or —$C(O)R_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl;

$R_a$ is independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

$R_b$ and $R_c$ are independently selected from H, $C_{1-6}$ alkyl, $C_{2-6}$ alkenyl, $C_{2-6}$ alkynyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or $R_b$ and $R_c$ are taken together with the nitrogen atom to which they are attached to form 3- to 7-membered heterocyclyl or 5- to 6-membered heteroaryl;

alternatively, wherein:

⎓ indicates a single bond or a double bond;

$R_1$ is selected from H, D, and halogen;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_{6-10}$ aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3 or 4 substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl;

alternatively, wherein:

⎓ indicates a single bond or a double bond;

$R_1$ is H, D, or halogen;

$R_2$ is selected from H, D, halogen, $C_{1-6}$ alkyl, and $C_{1-6}$ haloalkyl;

$R_3$ is selected from $C_{1-6}$ alkyl and $C_{1-6}$ haloalkyl;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl;

alternatively, wherein:

⎓ indicates a single bond or a double bond;

$R_1$ is H, or halogen;

$R_2$ is selected from H, D, halogen, $C_{1-6}$ alkyl, and $C_{1-6}$ haloalkyl;

$R_3$ is $C_{1-6}$ alkyl;

$R_4$ is —$S(O)_mR_d$; alternatively

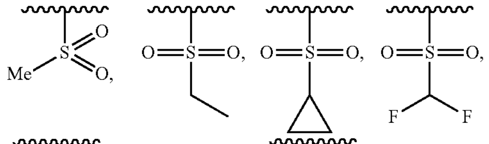

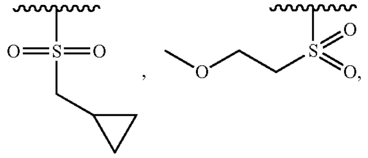

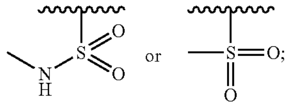

or ;

$R_d$ is $C_{1-6}$ alkyl, $C_{1-6}$ haloalkyl, —$C_{0-6}$ alkylene-$OR_5$, —$NR_6R_7$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl;

alternatively, wherein:

⎓ indicates a single bond or a double bond;

$R_1$ is H, D, or halogen;

$R_2$ is selected from H, D, halogen, $C_{1-6}$ alkyl, and $C_{1-6}$ haloalkyl;

$R_3$ is selected from —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3, 4 or more substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is —$S(O)_mR_d$;

$R_d$ is $C_{1-6}$ alkyl, $C_{1-6}$ haloalkyl, —$C_{0-6}$ alkylene-$OR_5$, —$NR_6R_7$, or —$C_{0-6}$ alkylene-$C_{3-7}$ cycloalkyl;

m is 1 or 2;

$R_5$, $R_6$ and $R_7$ are independently selected from H, $C_{1-6}$ alkyl and $C_{1-6}$ haloalkyl;

alternatively, wherein:

⎓ indicates a single bond or a double bond;

$R_1$ is H, D, or halogen;

$R_2$ is selected from H, D, halogen, $C_{1-6}$ alkyl, and $C_{1-6}$ haloalkyl;

$R_3$ is $C_{3-7}$ cycloalkyl, which may be optionally substituted by 1, 2, 3 or 4 substituents selected from D, halogen, —$C_{0-6}$ alkylene-$OR_5$, —CN, —$NR_6R_7$, $C_{1-6}$ alkyl and $C_{1-6}$ haloalkyl;

$R_4$ is —$S(O)_mR_d$; alternatively

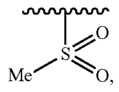 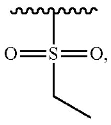 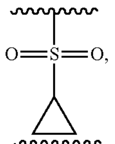 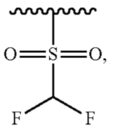

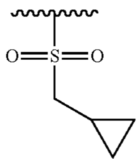 , 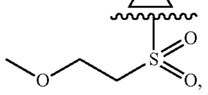

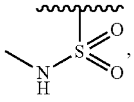 , or 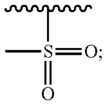

$R_d$ is $C_{1-6}$ alkyl, $C_{1-6}$ haloalkyl, —$C_{0-6}$ alkylene-$OR_5$, —$NR_6R_7$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl;

alternatively, wherein:

⎓ indicates a single bond or a double bond;

$R_1$ is H;

$R_2$ is $C_{1-6}$ haloalkyl;

$R_3$ is cyclopentyl, which may be optionally substituted by 1, 2 or 3 —OH or $C_{1-6}$ alkyl groups, alternatively $R_3$ is

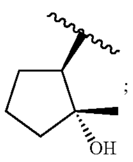 [SMILES: *[C@@H]1CCC[C@@]1(C)O] ;

$R_4$ is —$S(O)_mR_d$; alternatively

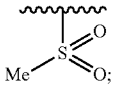

$R_d$ is $C_{1-6}$ alkyl, or $C_{1-6}$ haloalkyl;

m is 2.

11. The compound of claim 1, or a pharmaceutically acceptable salt, an enantiomer, a diastereomer, a racemate, a solvate, a hydrate, a polymorph, or an isotope variant thereof, or a mixture thereof, which has a structure of general formula (I-6) or (II-6):

(I-6)

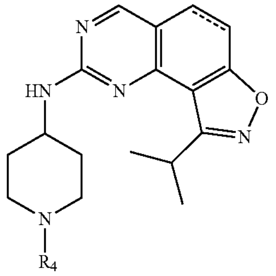

or (II-6)

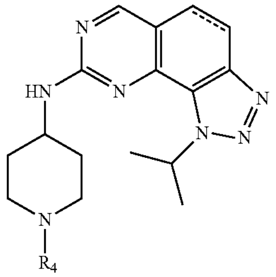

wherein:

⎓ indicates a single bond or a double bond;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl;

m is 1 or 2;

$R_5$, $R_6$ and $R_7$ are independently selected from H, $C_{1-6}$ alkyl and $C_{1-6}$ haloalkyl.

12. The compound of claim 11, or a pharmaceutically acceptable salt, an enantiomer, a diastereomer, a racemate, a solvate, a hydrate, a polymorph, or an isotope variant thereof, or a mixture thereof, wherein:

⎓ indicates a single bond or a double bond;

$R_4$ is —$S(O)_mR_d$;

$R_d$ is selected from $C_{1-6}$ alkyl, $C_{1-6}$ haloalkyl, —$C_{0-6}$ alkylene-$OR_5$, —$C_{0-6}$ alkylene-$NR_6R_7$, —$C_{0-6}$ alkylene-$C_{3-7}$ cycloalkyl, and —$C_{0-6}$ alkylene-3- to 7-membered heterocyclyl;

m is 1 or 2;

$R_5$, $R_6$ and $R_7$ are independently selected from H, $C_{1-6}$ alkyl and $C_{1-6}$ haloalkyl;

alternatively, wherein:

⎓ indicates a single bond or a double bond;

$R_4$ is —$S(O)_mR_d$; alternatively

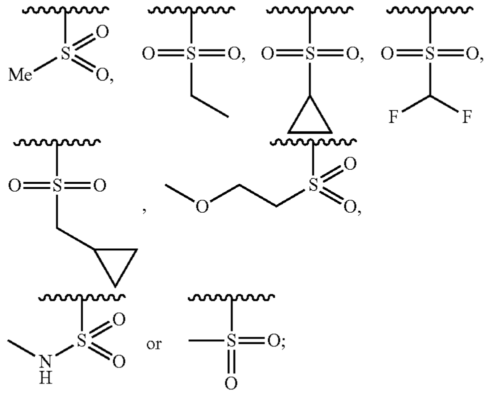

$R_d$ is $C_{1-6}$ alkyl, $C_{1-6}$ haloalkyl, —$C_{0-6}$ alkylene-$OR_5$, —$NR_6R_7$, or —$C_{0-6}$ alkylene-$C_{3-7}$ cycloalkyl;

m is 2;

$R_5$, $R_6$ and $R_7$ are independently selected from H, $C_{1-6}$ alkyl and $C_{1-6}$ haloalkyl.

13. The compound of claim 1, or a pharmaceutically acceptable salt, an enantiomer, a diastereomer, a racemate, a solvate, a hydrate, a polymorph, or an isotope variant thereof, or a mixture thereof, which has a structure of general formula (I-7) or (II-7):

(I-7)

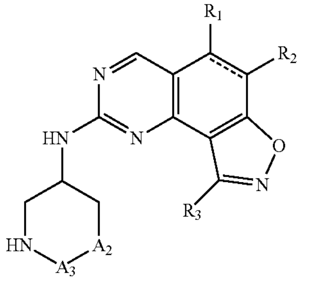

or (II-7)

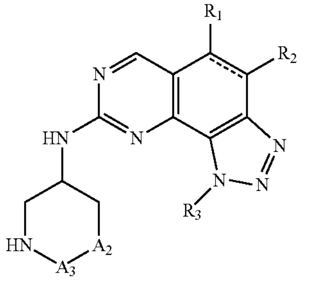

wherein $\overset{----}{—}$ indicates a single bond or a double bond;

$R_1$ is H, D, halogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_2$ is selected from H, D, halogen, $C_{1-6}$ alkyl, $C_{1-6}$ haloalkyl, $C_{3-7}$ cycloalkyl, 3- to 7-membered heterocyclyl, $C_6$-10 aryl and 5- to 10-membered heteroaryl;

$R_3$ is selected from $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl, which may be optionally substituted by 1, 2, 3 or 4 substituents selected from D, halogen, —$C_{0-6}$ alkylene-$OR_5$, —CN, —$NR_6R_7$, $C_{1-6}$ alkyl and $C_{1-6}$ haloalkyl;

$A_2$ is CRR' or NR';

$A_3$ is CRR';

R and R' are independently selected from H, D, halogen, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O.

14. The compound of claim 13, or a pharmaceutically acceptable salt, an enantiomer, a diastereomer, a racemate, a solvate, a hydrate, a polymorph, or an isotope variant thereof, or a mixture thereof, wherein:

$\overset{----}{—}$ indicates a single bond or a double bond;

$R_1$ is H, D, or halogen;

$R_2$ is selected from H, D, and halogen;

$R_3$ is selected from $C_{1-6}$ alkyl and $C_{1-6}$ haloalkyl;

$A_2$ is CRR' or NR';

$A_3$ is CRR';

R and R' are independently selected from H, D, halogen, $C_{1-6}$ alkyl, $C_{1-6}$ haloalkyl, —$C_{0-6}$ alkylene-$C_{3-7}$ cycloalkyl, —$C_{0-6}$ alkylene-3- to 7-membered heterocyclyl, —$C_{0-6}$ alkylene-$C_{6-10}$ aryl and —$C_{0-6}$ alkylene-5- to 10-membered heteroaryl; or R, R' and the carbon atom attached thereto are combined to form C═O;

alternatively, wherein:

$\overset{----}{—}$ indicates a single bond or a double bond;

$R_1$ is H;

$R_2$ is H;

$R_3$ is $C_{1-6}$ alkyl;

$A_2$ is CRR', alternatively —$CH_2$—;

$A_3$ is CRR';

R and R' are independently H; or R, R' and the carbon atom attached thereto are combined to form C═O.

15. A compound, or a pharmaceutically acceptable salt, an enantiomer, a diastereomer, a racemate, a solvate, a hydrate, a polymorph, or an isotope variant thereof, wherein the compound is selected from:

I.1

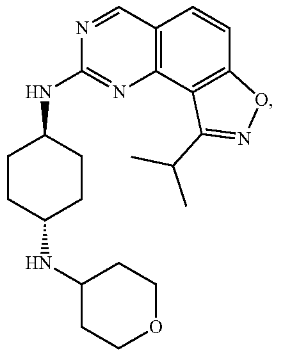

-continued
I.2
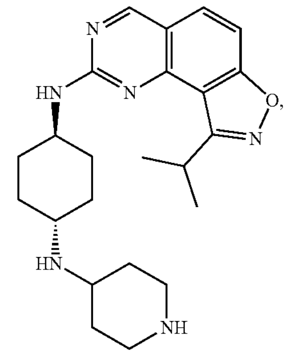
I.3
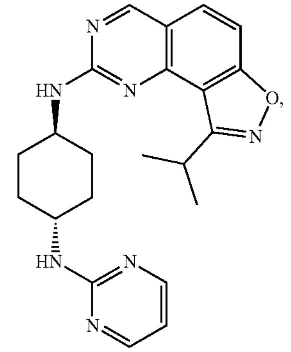
I.4
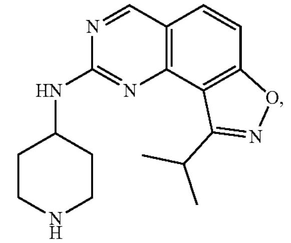
I.5
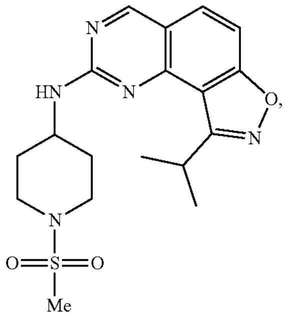
I.6
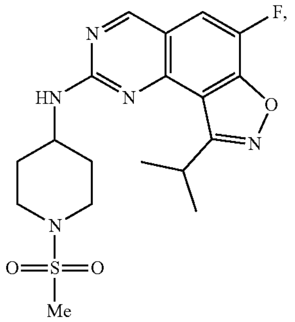
-continued
I.7
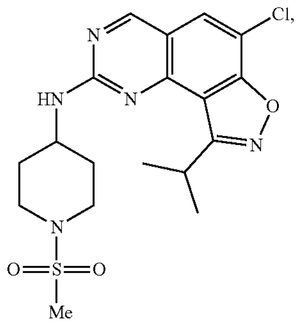
I.8
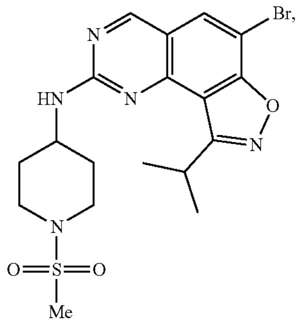
I.9
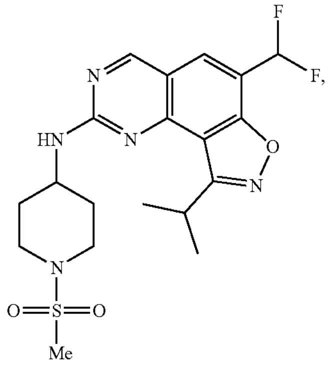
I.10
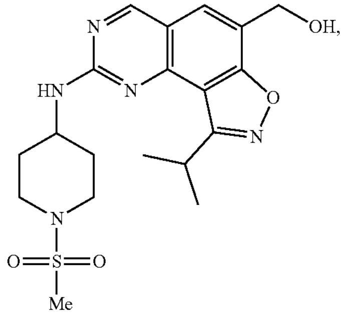

-continued
I.11
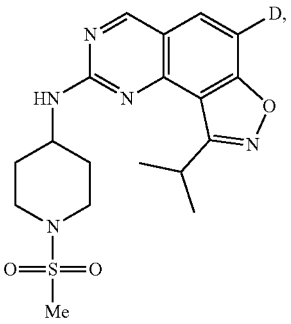
I.12
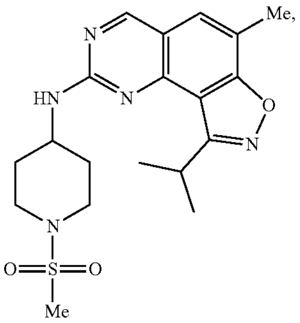
I.13
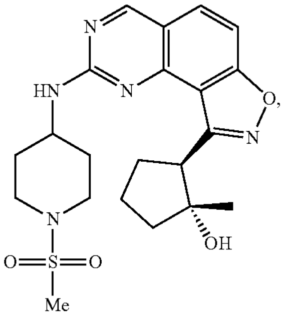
I.14
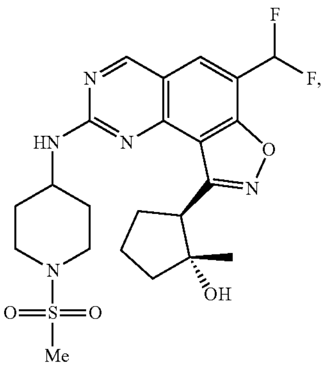
-continued
I.15
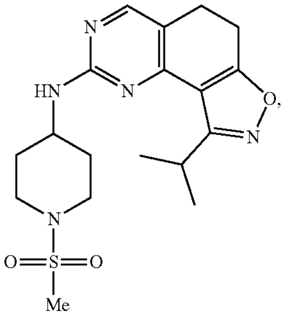
I.16
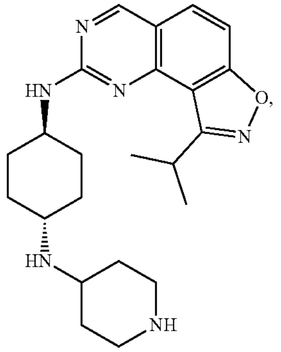
II.1
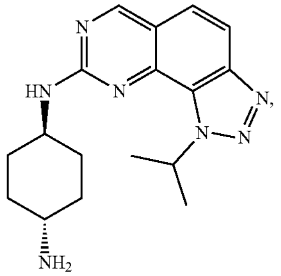
II.2
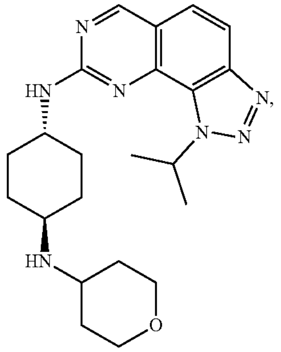

-continued
II.3
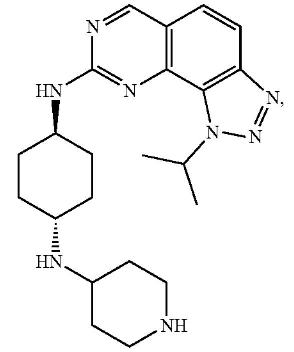
II.4
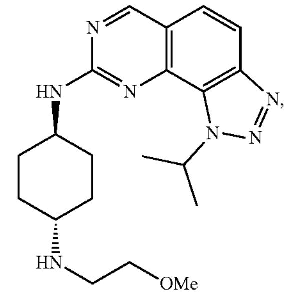
II.5
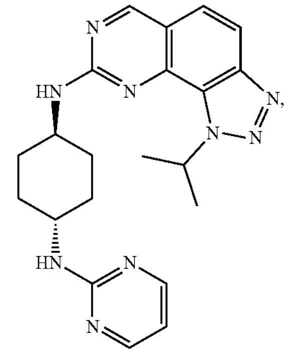
II.6
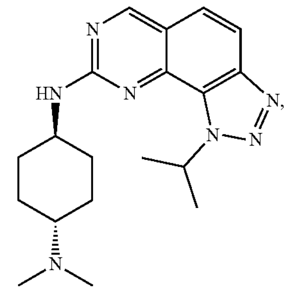
-continued
II.7
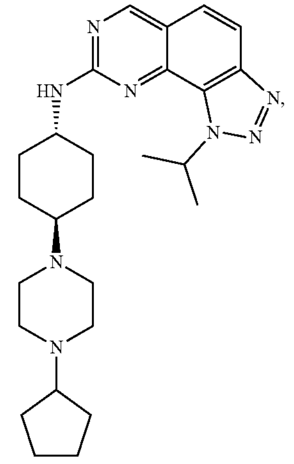
II.8
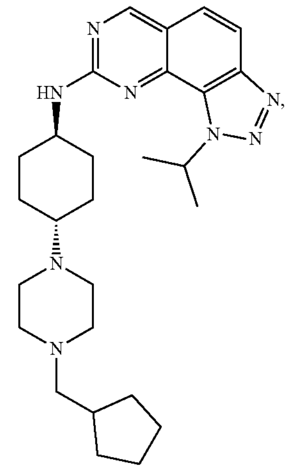
II.9
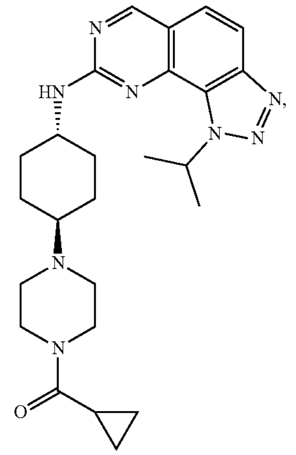

-continued
II.10
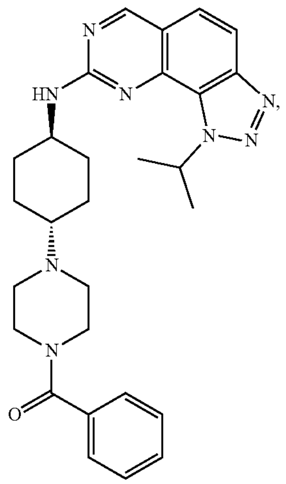
II.11
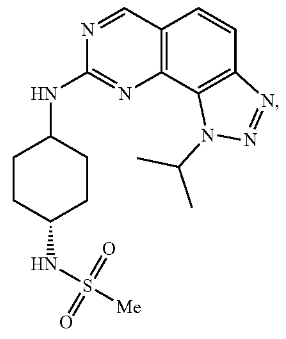
II.12
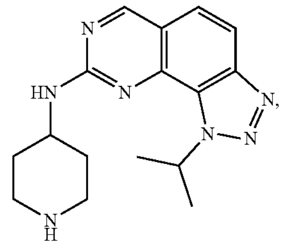
II.13
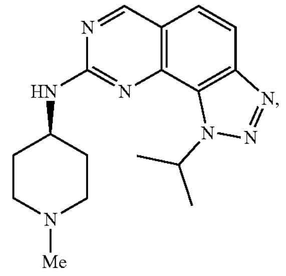
-continued
II.14
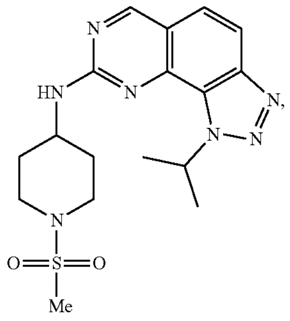
II.15
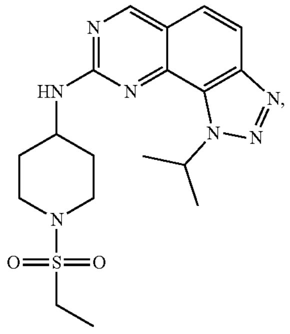
II.16
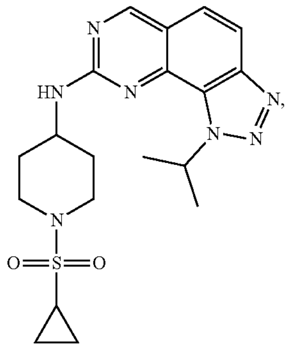
II.17
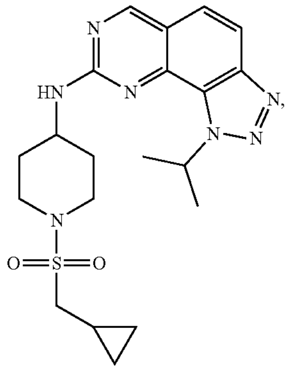

-continued
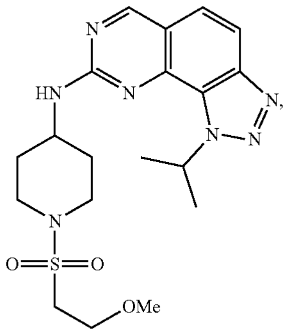
II.18
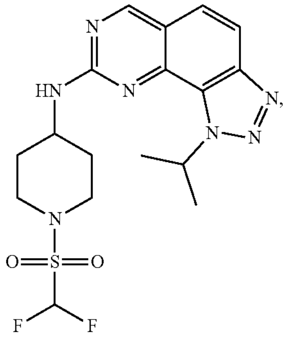
II.19
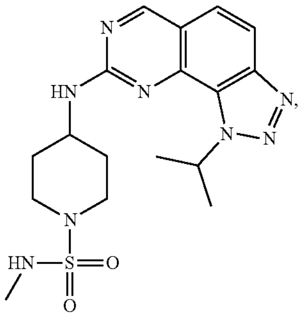
II.20
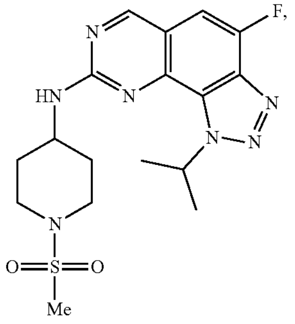
II.21
-continued
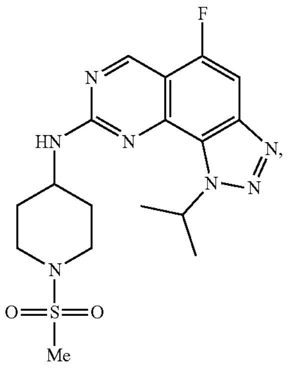
II.22
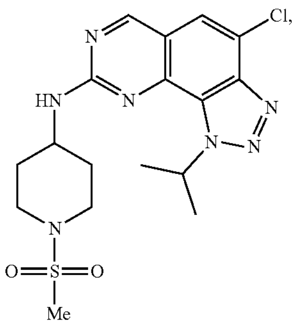
II.23
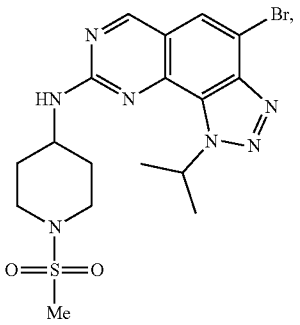
II.24
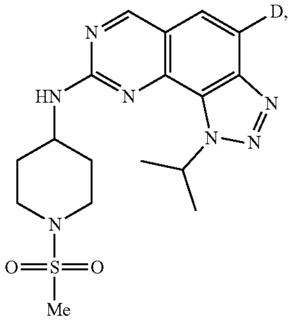
II.25

-continued
II.26
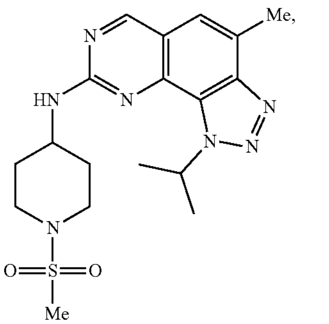
II.27
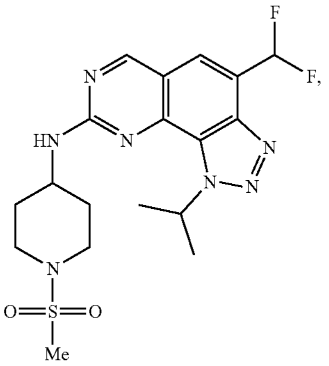
II.28
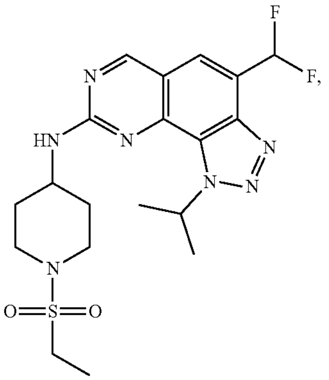
II.29
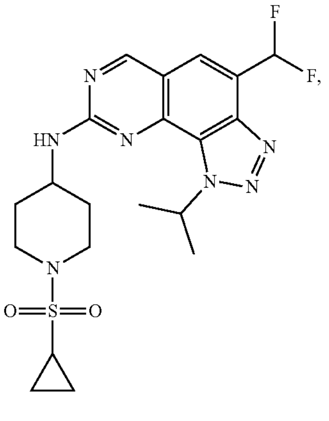
-continued
II.30
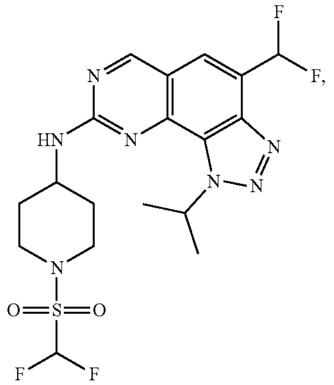
II.31
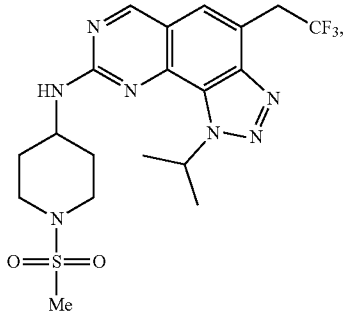
II.32
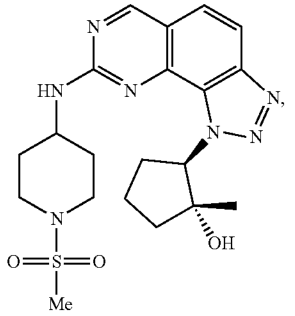
II.33
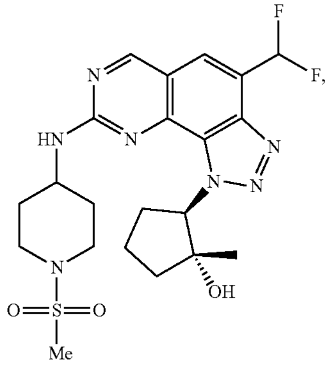
II.34
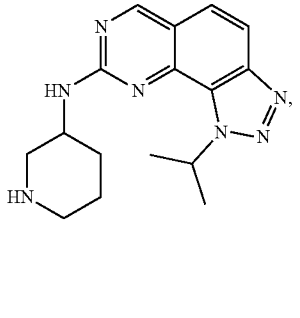

-continued

II.35

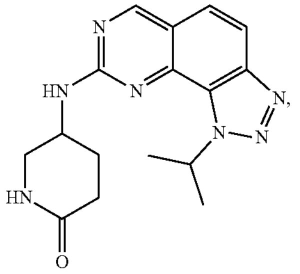

II.36

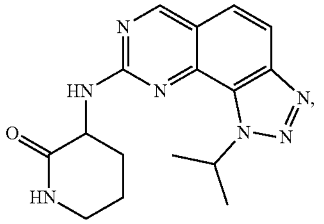

II.37

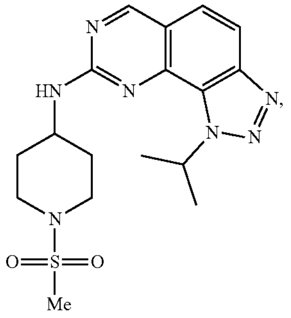

II.38

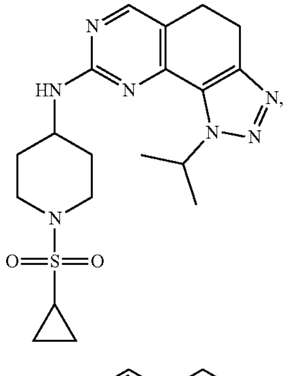

and

II.39

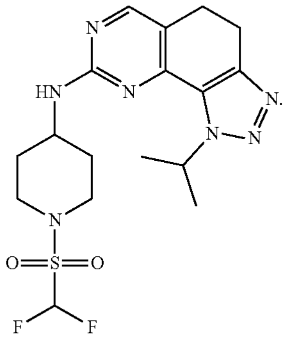

16. A pharmaceutical composition containing the compound of claim 1, or a pharmaceutically acceptable salt, an enantiomer, a diastereomer, a racemate, a solvate, a hydrate, a polymorph, or an isotope variant thereof, and pharmaceutically acceptable excipient(s); optionally, which further contains other therapeutic agent(s).

17. A kit, comprising:

a first container, containing the compound of claim 1, or a pharmaceutically acceptable salt, an enantiomer, a diastereomer, a racemate, a solvate, a hydrate, a polymorph, or an isotope variant thereof; and optionally, a second container, containing other therapeutic agent(s); and optionally, a third container, containing pharmaceutical excipient(s) for diluting or suspending the compound and/or other therapeutic agent(s).

18. A pharmaceutical composition containing the compound of claim 15, or a pharmaceutically acceptable salt, an enantiomer, a diastereomer, a racemate, a solvate, a hydrate, a polymorph, or an isotope variant thereof, and pharmaceutically acceptable excipient(s); optionally, which further contains other therapeutic agent(s).

19. A kit, comprising:

a first container, containing the compound of claim 15, or a pharmaceutically acceptable salt, an enantiomer, a diastereomer, a racemate, a solvate, a hydrate, a polymorph, or an isotope variant thereof; and optionally, a second container, containing other therapeutic agent(s); and optionally, a third container, containing pharmaceutical excipient(s) for diluting or suspending the compound and/or other therapeutic agent(s).

20. A method for treating CDK-mediated diseases in a subject, which comprises administering to the subject the compound of claim 1 or a pharmaceutically acceptable salt, an enantiomer, a diastereomer, a racemate, a solvate, a hydrate, a polymorph, or an isotope variant thereof, wherein the diseases are CDK-mediated diseases, wherein the CDK-mediated diseases are solid tumors, sarcomas and carcinomas.

21. The method of claim 20, wherein the CDK-mediated diseases are fibrosarcoma, myxosarcoma, liposarcoma, chondrosarcoma, osteosarcoma, chordoma, angiosarcoma, endothelial sarcoma, lymphangiosarcoma, lymphangioendothelioma, synovialoma, mesothelioma, ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, hidradenoma, sebaceous carcinoma, papillary carcinoma, papillary adenocarcinoma, cystadenocarcinoma, medullary carcinoma, bronchial carcinoma, renal cell carcinoma, liver cancer, cholangiocarcinoma, choriocarcinoma, seminoma, embryonal cancer, embryonal carcinosarcoma, cervical cancer, uterine cancer, testicular cancer, lung cancer, small cell lung cancer, bladder cancer, epithelial cancer, glioma, astrocytoma, medulloblastoma, craniopharyngioma, ependymoma, pineal tumor, hemangioblastoma, acoustic neuroma, oligodendroglioma, schwannoma, meningioma, melanoma, neuroblastoma and retinoblastoma.

* * * * *